US010495641B2

(12) United States Patent
Nuovo et al.

(10) Patent No.: US 10,495,641 B2
(45) Date of Patent: Dec. 3, 2019

(54) DIAGNOSIS AND TREATMENT OF VIRAL DISEASES

(71) Applicant: ENZO BIOCHEM, INC, New York, NY (US)

(72) Inventors: Gerard Nuovo, Westerville, OH (US); Virginia Nivar, Marion, OH (US)

(73) Assignee: Enzo Biochem, Inc., New York, NY (US)

( * ) Notice: Subject to any disclaimer, the term of this patent is extended or adjusted under 35 U.S.C. 154(b) by 161 days.

(21) Appl. No.: 15/897,217

(22) Filed: Feb. 15, 2018

(65) Prior Publication Data

US 2018/0180615 A1    Jun. 28, 2018

Related U.S. Application Data

(63) Continuation of application No. 15/439,495, filed on Feb. 22, 2017, now Pat. No. 9,933,427, which is a continuation of application No. 14/759,687, filed as application No. PCT/US2014/000675 on Jan. 8, 2014, now Pat. No. 9,617,607, which is a continuation-in-part of application No. 14/080,644, filed on Nov. 14, 2013, now abandoned, which is a continuation-in-part of application No. 13/920,964, filed on Jun. 18, 2013, now abandoned.

(60) Provisional application No. 61/750,104, filed on Jan. 8, 2013.

(51) Int. Cl.
| | | |
|---|---|---|
| C12Q 1/68 | (2018.01) |
| C07H 21/02 | (2006.01) |
| G01N 33/569 | (2006.01) |
| C12Q 1/70 | (2006.01) |
| C07K 16/08 | (2006.01) |
| C07K 16/24 | (2006.01) |
| C12Q 1/6883 | (2018.01) |
| C12Q 1/6886 | (2018.01) |

(52) U.S. Cl.
CPC ..... *G01N 33/56994* (2013.01); *C07K 16/085* (2013.01); *C07K 16/244* (2013.01); *C12Q 1/6883* (2013.01); *C12Q 1/6886* (2013.01); *C12Q 1/705* (2013.01); *C07K 2317/33* (2013.01); *C07K 2317/76* (2013.01); *C12N 2710/16021* (2013.01); *C12Q 2600/158* (2013.01); *G01N 2333/03* (2013.01); *G01N 2800/7052* (2013.01)

(58) Field of Classification Search
None
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes |
| 5,059,595 A | 10/1991 | Le Grazie |
| 5,073,543 A | 12/1991 | Marshall et al. |
| 5,120,548 A | 6/1992 | McClelland |
| 5,354,556 A | 10/1994 | Sparks |
| 5,591,767 A | 1/1997 | Mohr et al. |
| 5,639,476 A | 6/1997 | Oshlack et al. |
| 5,674,533 A | 10/1997 | Santus et al. |
| 5,698,155 A | 12/1997 | Grosswald et al. |
| 5,733,566 A | 3/1998 | Lewis |
| 5,925,733 A | 7/1999 | Rose et al. |
| 6,054,283 A | 4/2000 | Salahuddin et al. |
| 6,264,958 B1 | 7/2001 | Hayward et al. |
| 6,743,605 B1 | 6/2004 | Rabbani et al. |
| 7,514,551 B2 | 4/2009 | Rabbani et al. |
| 7,569,695 B2 | 8/2009 | Xiang et al. |
| 8,153,802 B2 | 4/2012 | Xiang et al. |
| 8,247,179 B2 | 8/2012 | Rabbani et al. |
| 8,389,729 B2 | 3/2013 | Xiang et al. |
| 2002/0137020 A1 | 9/2002 | Chang |
| 2003/0215793 A1 | 11/2003 | Hahn |

(Continued)

FOREIGN PATENT DOCUMENTS

| | | |
|---|---|---|
| WO | WO2008/125366 | 7/2009 |
| WO | WO2010/135690 | 11/2010 |

OTHER PUBLICATIONS

Arvin et al., Human Herpesviruses: Biology, therapy and immunoprophylaxis, Cambridge: Cambridge University Press 2007, Chapter 2 Comparative analysis of the genomes, http://www/ncbi.nlm.nih.gov/books/NBK47439/?report=printable.

(Continued)

*Primary Examiner* — Jehanne S Sitton

(74) *Attorney, Agent, or Firm* — Paul Diamond, Esq.

(57) ABSTRACT

This disclosure relates to methods of diagnosing a viral disease such as idiopathic pulmonary fibrosis, Castleman's disease, a lymphoma, a thymoma or a sarcoma in a patient by identifying one or more virus-specific elements such as a nucleic acid or a viral protein or a patient antibody to a virus-specific element, as well as to kits for diagnosing the viral disease in a patient. The disclosure further relates to methods of monitoring disease progression and/or the efficacy of therapy by measuring the levels of a virus-specific element in a sample from a patient. In addition, the disclosure relates to methods of identifying therapeutic agents that show efficacy in reducing levels of virus-specific agents in vitro. The disclosure further relates to methods of treating idiopathic pulmonary fibrosis, a lymphoproliferative disease and cancer, as well as to methods of preventing viral infection, including Herpesvirus saimiri infection.

12 Claims, 25 Drawing Sheets

Figure 1A:
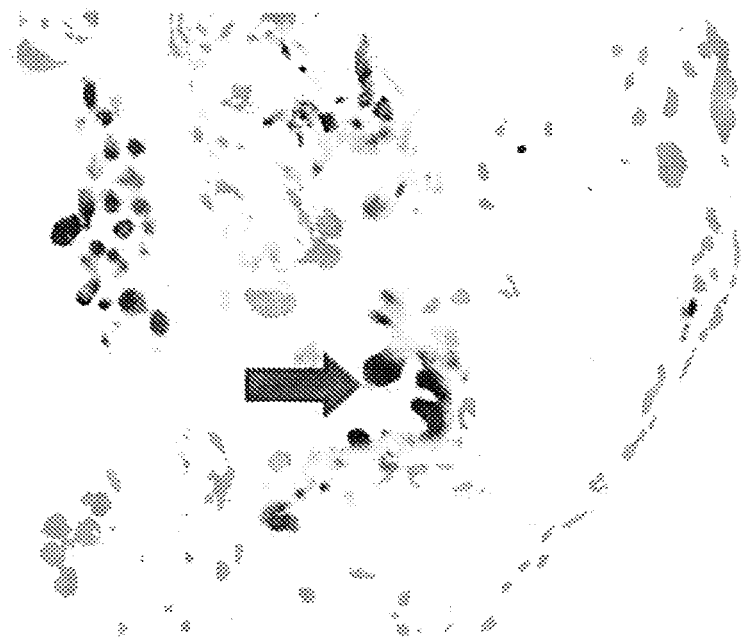

Specification includes a Sequence Listing.

(56) References Cited

U.S. PATENT DOCUMENTS

| | | |
|---|---|---|
| 2010/0273145 A1 | 10/2010 | Pargolizzi et al. |
| 2010/0291024 A1 | 11/2010 | Qin et al. |
| 2011/0265195 A1 | 10/2011 | Chang et al. |
| 2012/0040430 A1 | 2/2012 | Xiang et al. |
| 2012/0269801 A1 | 10/2012 | Qin et al. |
| 2014/0193423 A1 | 7/2014 | Nuovo et al. |
| 2014/0322188 A1 | 10/2014 | Nussenblatt et al. |
| 2014/0370028 A1 | 12/2014 | Nuovo |
| 2016/0177396 A1 | 6/2016 | Rabbani |

OTHER PUBLICATIONS

Ball et al., The use of tailed octamer primers for cycle sequencing, Nucleic Acids Research 1998, 5225-5227, 26(22).

Beaudenon et al., A novel type of human papillomavirus associated with genital neoplasias, Nature 1988, 246-249, 321.

Bergmeyer, Hans Ulrich, Methods of Enzymatio Analysis 1974, Verlag Chemie GmbH Weinheim, Academic Press, Inc., pp. 2059-2072, vol. 4.

Boshart et al. A new type of papillomavirus DNA, Its presence in genital cancer biopsies and in cell lines derived from cervical cancer, The EMBO Journal 1984, 1151-1157, 3(5).

Cazalla et al., Down-regulation of a host microRNA by a herpesvirus-saimiri noncoding RNA. Science 2010, 1563-1566, 328.

Dahlberg et al., Analysis of herpesvirus salmiri structural proteins with monoclonal antibodies, J. Virol. 1985, 279-286, 53(1).

Durst et al., A papillomavirus DNA from a cervical carcinoma and its prevalence in cancer biopsy samples from different geographical regions, Proc. Natl. Acad. Sci. 1983, 3812-3815, 80.

Ehlers et al., Identification of novel rodent herpesviruses, including the first gammaherpesvirus of Mus musculus, Journal of Virology 2007, 8091-8100, 81(15).

Ehlers et al., Novel mammalian herpesviruses and lineages within the gammaherpesvirinae: Cospeciation and interspecies transfer, Journal of Virology 2008, 3509-3516, 82(7).

Eizuru et al., Application of "Hirt Supematent" DNA to the molecular epidemiology of cytomegalovirus infections, Journal of Clinical Microbiology 1964, 1012-1014, 20(5).

Fleckenstein et al., Herpesvirus ateles DNA and its homology with herpesvirus saimiri nucleic acid, Journal of Virology 1978, 361-373, 25(1).

Gissman et al., Molecular cloning and characterization of human papilloma virus DNA derived from a jaryngeal papilloma, Journal of Virology 1982, 393-400, 44(1).

Goodson, J. Max, Chapter 6 Dental Applications, Medical Applications of Controlled Release vol. 2, Langer and Wise, CRC Press 1984, pp. 115-138.

Hirt et al., Selective extraction of polyoma DNA from infected mouse cell cultures, J. Mol. Biol. 1967, 365-369, 26.

De Roda Husman et al., The use of general primers GP5 and GP6 elongated at their 3' ends with adjacent highly conserved sequences improves human papillomavirus detection by PCR, Journal of General Virology 1995, 1057-1062, 76.

Kawase et al., Studies on nucleic acid interactions 1. Stabilities of mini-duplexes (dG2A4XA4G2.dC2T4YT4C2) and self-complementary d(GGGAAXYTTCCC) containing deoxyinosine and other mismatched bases, Nucleic Acids Research 1986, 7727-7736, 14(19).

Kintner and Brandt, Rapid small-scale isolation of herpes simplex virus DNA, Journal of Virological Methods 1994, 189-196, 48.

Knappe et al., Induction of a novel cellular homolog of Interleukin-10, AK155, by transformation of T lymphocytes with herpesvirus saimiri, Journal of Virology 2000, 3881-3887, 74(8).

Lacoste et al., Genetic diversity and molecular evolution of human and non-human primate gammaherpesvirinae, Infection, Genetics and Evolution 2010, 1-13, 10.

Liu and Nichols, PCR amplification using deoxyinosine to replace an entire codon and at ambiguous positions, Biotechniques 1994, 24-26, 16(1).

Loakes, O., The applications of universal DNA base analogues, Nucleic Acid Research 2001, 2437-2447, 29(12).

Loakes and Brown, 5-Nitroindole as an universal base analogue, Nucleic Acids Research 1994, 4039-4043, 22(20).

Lorincz et al., Cloning and characterization of the DNA of a new human papillomavirus from a woman with dysplasia of the uterine cervix, Journal of Virology 1986, 225-229, 58(1).

Malenovska, H., Virus quaniliation by transmission electron microscopy, TCID50, and the role of timing virus harvesting: A case study of three animal viruses, Journal of Virological Methods 2013, 136-140, 191.

Manos et al., Use of polymerase chain reaction amplification for the detection of genital human papillomavirues, Cancer Cells 7, Cold Springs Harbor Laboratory 1989, 209-214.

Muerhoff et al., Amplification and subtraction methods and their application to the discovery of novel human viruses, Journal of Medical Virology 1997, 96-103, 53.

Nichols et al., A universal nucleoside for use at ambiguous sites in DNA primers, Nature 1994, 492-493, 369.

Nuovo et al., Isolation of a novel human papillomavirus (Type 51) from a cervical condyloma, Journal of Virology 1988, 1452-1455, 82(4).

Passonneau et al., Enzymatic analysis. A practical guide. Chapter 5, Enzymatic Cycling, Totowa NJ: Humana Press 1993, pp. 85-110.

Pater et al., Isolation of herpes simplex virus DNA from the "Hirt Supematent", Virology 1976, 481-483, 75.

Pignatti et al., Herpes simplex virus DNA isolation from infected cells with a novel procedure, Virology 1979, 260-264, 93.

Randall et al., Isolation and characterization of monoclonal antibodies to structural and nonstructural herpesvirus saimiri proteins, Journal of Virology 1984, 872-883, 52(3).

Rosenthal et al., Isolation of human cytomegalovirus DNA from infected cells, Intervirology 1983, 113-120, 19.

Churchwell et al., "Improving LC-MS sensitivity through increases in chromatographic performance: Comparisons of UPLC-ES/MS/MS to HPLC-ES/MS/MS," *Journal of Chromatography B*, vol. 825, pp. 134-143 (2005).

Egan et al., "Epatain-Barr virus replication within pulmonary epithelial cells in cryptogenic fibrosing alveolitis," *Thorax*, vol. 50, pp. 1234-1239 (1995).

Griffin, "Metabonomics: NMR spectroscopy and pattern recognition analysis of body fluids and tissues for characterization of xenobiotic toxicity and disease diagnosis," *Current Opinion in Chemical Biology*, vol. 7, pp. 648-664 (2003).

Hall et al., "Sensitive detection of DNA polymorphisms by the serial invasive signal amplification reaction," *PNAS*, vol. 97, No. 15, pp. 8272-8277 (2000).

Malenovska, "Virus quantitation by transmission electron microscopy, TCIDs, and the role of timing virus harvesting: A case study of three animal viruses," *Journal of Virological Methods*, vol. 191, pp. 138-140 (2013).

Alberier et al., "Genome-Wide Histone Acetylation Profiling of *Herpasvirus simiri* in Human T Cells upon Induction with a Histone Deacetylase Inhibitor," *J. Virol.*, vol. 85, No. 11, pp. 5456-5464 (2011).

Nuovo, Gerard, In situ detection of microRNAs in paraffin embedded, formalin fixed tissues and the co-localization of their putative targets, Methods 2010, 307-315, 52.

Nuovo et al., A methodology for the combined in situ analyses of the precursor and mature forms of microRNAs and correlation with their putative targets, Nat Protoc 2009, 107-115, 4(1).

Papiris et al., Steroids in idiopathic pulmonary fibrosis acute exacerbation: defenders or killers?, Am. J. Respir. Crit. Care Med. 2012, 587-588, 185(5).

Pei et al., Sandwich-type immunosensors and immunoassays exploiting nanostructure labels: A review, Analytica Chimica Acta 2013, 1-18, 758.

Queen et al., A humanized antibody that binds to the interleukin 2 receptor, Proc. Natl. Acad Sci. 1989, 10029-10033, 86.

Rafii et al., A review of current and novel therapies for idiopathic pulmonary fibrosis, J. Thorac. Dis. 2013, 48-73, 5(1).

(56) References Cited

OTHER PUBLICATIONS

Raghu et al., An official ATS/ERS/JRS/ALAT statement: idiopathic pulmonary fibrosis: evidence-based guidelines for, diagnosis and management, Am. J. Respir. Crit. Care Med. 2011, 788-824, 183.
Riechmann et al., Reshaping human antibodies for therapy, Nature 1988, 323-327, 332.
Rodda et al., The single radial immunodiffusion assay highlights small antigenic differences among influenza virus hemagglutinins, J. Clin. Microbiol. 1981, 479-482, 14(5).
Schauer et al., GC-MS libraries for the rapid identification of metabolites in complex biological samples, FEBS Letters 2005, 1332-1337, 579(6).
Simmer et al., Persistence of selectable herpesvirus saimiri in various human haematopoietic and epithelial cell lines, J. Gen. Vir. 1991, 1953-1958, 72.
Smith et al., Measurement of protein using bicinchoninic acid, Anal. Biochem. 1985, 76-85, 150.
Soga et al., Quantitative metabolome analysis using capillary electrophoresis mass spectrometry, J. Proteome Res. 2003, 486-494, 2(5).
Stewart et al., The detection of Epstein-Barr virus DNA in lung tissue from patients with idiopathic pulmonary fibrosis, Am. J. Respir. Care Med. 1999, 1336-1341, 159.
Stijn et al., Multiplex protein profiling of bronchoalveolar lavage in idiopathic pulmonary fibrosis and hypersensitivity pneumonitis, Annals Thoracic Med. 2013, 38-44, 8(1).
Stoffel et al., Rapid determination of baculovirus titer by a dual-channel virus counter, American Biotechnology Laboratory 2005, 24-25, 22.
Storhoff et al., Homogenous detection of unamplified genomic DNA sequences based on calorimetric scatter of gold nanoparticle probes, Nat. Biotechnol. 2004, 883-887, 22(7).
Tang et al., Herpesvirus DNA is consistently detected in lungs of patients with idiopathic pulmonary fibrosis, J. Clin. Microbiol. 2003, 2633-2640, 41(6).
Telenius et al., Degenerate oligonucleotide-primed PCR: General amplification of target DNA by a single degenerate primer, Genomics 1992, 718-725, 13.
Terry et al., Detection of high-risk HPV types by the hybrid capture 2 test, J. Med. Virol. 2001, 155-162, 65.
Todd and Gomez, Enzyme kinetics determined using calorimetry: A general assay for enzyme activity?, Analytical Biochemistry 2001, 179-187, 296.
Vandevanter et al., Detection and analysis of diverse herpesviral species by consensus primer PCR, J. Clin. Microbiol. 1996, 1868-1871, 34(7).
Wilhelm and Pingoud, Real-time polymerase chain reaction, ChemBioChem 2003, 1120-1128, 4.
Woo et al., Nanostructure-initiator mass spectrometry: a protocol for preparing and applying NIMS surfaces for high-sensitivity mass analysis, Nature Protocols 2008, 1341-1349, 3(8).
Wootton et al., Viral infection in acute exacerbation of idiopathic pulmonary fibrosis, Am. J. Respir. Crit. Care Med. 2011, 1698-1702, 183.
Wu et al., Prospects of a novel vaccination strategy for human gamma-herpesviruses, Immunol. Res. 2010, 122-146, 48.
Yonemaru et al., Elevation of antibodies to cytomegalovirus and other herpes viruses in pulmonary fibrosis, Eur. Respir. J 1997, 2040-2045, 10.
Zamo et al., HHV-8 and EBV are not commonly found in idiopathic pulmonary fibrosis, Sarcoidosis Vasculitis and Diffuse Lung Diseases 2005, 123-128, 22.
Zhang and Guo, Multiple labeling of antibodies with Dye/DNA conjugate for sensitivity improvement in fluorescence immunoassay, Bioconjugate Chem. 2007, 1668-1672, 18.
Ablashi et al., Detection of antibodies to herpesvirus saimiri late antigens in human sera, Intervirology 1988, 217-226, 29.
Adamali and Maher, Current and novel drug therapies for idiopathic pulmonary fibrosis, Drug Design, Development and Therapy 2012, 261-272, 6.
Albrecht et al., Primary structure of the herpesvirus saimiri genome, J. Virology 1992, 5047-5058, 66(8).
Arya et al., Basic principles of real-time quantitative PCR. Expert Rev. Mol. Diagn. 2005, 209-219, 5(2).
Bankier et al., Terminal repetitive sequences in herpesvirus saimiri virion DNA, Journal of Virology 1985, 133-139, 55(1).
Beckonert et al., Metabolic profiling, metabolomic and metabonomic procedures for NMR spectroscopy of urine, plasma, serum and tissue extracts, Nature Protocols 2007, 2692-2703, 2(11).
Biesinger et al., Stable growth transformation of human T lymphocytes by herpesvirus saimiri, Proc. Natl. Acad. Sci. 1992, 3116-3119, 89.
Burke, R.L., Contemporary approaches to vaccination against herpes simplex virus, Curr. Topics Microbiol. Immunol. 1992, 137-158, 179.
Chmielewicz et al., Detection and multigenic characterization of a novel gammaherpesvirus in goats, Virus Research 2001, 87-94, 75.
Churchwell et al., Improving LC-MS sensitivity through increases in chromatographic performance: Comparisons of UPLC-ES/MS/MS to HPLC-ES/MS/MS, Journal of Chromatography B 2005, 134-143, 825.
Collins et al., The terminal repeats and latency-associated nuclear antigen of herpesvirus saimiri are essential for episomal persistence of the viral genome, The Journal of General Virology 2002, 2269-2278, 83.
Coquillard et al., Quantification of intracellular HPV E6/E7 mRNA expression increases the specificity and positive predictive value of cervical cancer screening compared to HPV DNA, Gynecologic Oncology 2011, 89-93, 120.
Corchero et al., Comparision of serologic assays for detection of antibodies against human herpesvirus 8, Clinical and Diagnostic Laboratory Immunology 2001, 913-921, 8(5).
Cottin, Vincent, Changing the idiopathic pulmonary fibrosis treatment approach and improving patient outcomes, Eur Respir Rev 161-167, 21(124).
Dean et al., Comprehensive human genome amplification using multiple displacement amplification, Proc. Natl. Acad. Sci. 2002, 5261-5266, 99(8).
Dunbar et al., Ouantitative, multiplexed detection of bacterial pathogens: DNA and protein application of the Luminex LabMAP system, Journal of Microbiological Methods 2003, 245-252, 53.
Dworniczak et al., Human cytomegalovirus DNA level in patients with idiopathic pulmonary fibrosis, J. Physiol. Pharmacol., 2004, 67-75, 55(Suppl. 3).
Eberwine et al., Analysis of gene expression in single live neurons, Proc. Natl. Acad. Sci. 1992, 3010-3014, 89.
Ebina et al., Gradual increase of high mobility group protein B1 in the lungs after the onset of acute exacerbation of a idiopathic pulmonary fibrosis, Pulmonary Medicine 2011, Article ID 916486, 9 pgs.
Egan et al., Detection of human cytomegalovirus antigenaemia: a rapid diagnostic technique for predicting cytomegalovirus infection/pneumonitis in lung and heart transplant recipients, Thorax 1995, 9-13, 50.
Egan et al., Ganciciovir antiviral therapy in advanced idiopathic pulmonary fibrosis: An open pilot study, Pulmonary Medicine 2011, Article ID 240805, 5 pgs.
Ensser et al., The genome of herpesvirus saimiri C488 which is capable of transforming human T cells, Virology 2003, 471-487, 314.
Estep et al., Simian herpesviruses and their risk to humans, Vaccine 2010, B78-B84, 285.
Fickenscher and Fleckenstein, Herpesvirus saimiri, Phil., Trans. R. Soc. Lond. B 2001, 545-567, 356.
Frieden and Orum, Locked nucleic acid holds promise in the treatment of cancer, Curr. Pharm. Design, 2008, 1138-1142, 14.
Gardella et al., Detection of circular and linear herpesvirus DNA molecules in mammalian cells by gel electrophoresis, Journal of Virology 1984, 248-254, 50(1).
Gika et al., Within-day reproducibility of an HPLC-MS-based method for metabonomic analysis: application to human urine, J. Proteome Res. 2007, 3291-3303, 6(8).

(56) References Cited

OTHER PUBLICATIONS

Gill and Ghaemi et al., Nucleic acid isothermal amplification technologies—a review, Nucleosides, Nucleotides, and Nucleic acids 2008, 224-243, 27.
Grffin, Julian, Metabonomics: NMR spectroscopy and pattern recognition analysis of body fluids and tissues for characterization of xenobiotic toxicity and disease diagnosis, Curr Opin Chem Biol 2003, 648-654, 7.
Hall et al., Analysis of gene expression in a human cell line stably transduced with herpesvirus saimiri, J. Virol. 2000, 7331-7337, 74(16).
Hofstadler et al., Tiger: the universal biosensor, Intl J. Mass Spectrometry 2005, 23-41, 242.
Holliger and Hudson, Engineered antibody fragments and the rise of single domains, Nature Biotechnology 2005, 1126-1136, 23(9).
Hoogenboom, Hennie, Selecting and screening recombinant antibody libraries, Nature Biotechnology 2005, 1105-1116, 23(9).
Johnston et al., HSV-2: In pursuit of a vaccine, J. Clin Invest. 2011, 4600-4609, 121(12).
Karem et al., Protective immunity against herpes simplex virus (HSV) type 1 following oral administration of recombinant *Salmonella typhimurium* vaccine strains expressing HSV antigens, J Gen. Virol. 1997, 427-434, 78.
Kaschka-Dierich et al., Structure of nonintegrated, circular herpesvirus saimiri and herpesvirus ateles genomes in tumor cell lines and in vitro-transformed cells, J. Virol. 1982, 295-310, 44(1).
King et al., Effect of interferon gamma-1b on survival in patients with idiopathic pulmonary fibrosis (INSPIRE): a multicentre, randomised, placebo-controlled trial, The Lancet 2009, 222-228, 374(9885).
Koelle and Corey, Recent progress in herpes simplex virus immunobiology and vaccine research, Clin. Microbiol. Revs. 2003, 98-113, 16(1).
Kutok and Wang, Spectrum of Epstein-Barr virus-associated diseases, Annu. Rev. Pathol. Mech. Dis. 2006, 375-404, 1.
Langer, Robert, New methods of drug delivery, Science, 1990, 1527-1533, 249(4976).
Langer-Safer et al., Immunological method for mapping genes on *Drosophila* polytene chromosomes, Proc. Natl. Acad. Sci. 1982, 4381-4385, 79.
Lizardi et al., Mutation detection and single-molecule counting using isothermal rolling-circle amplification, Nature Genetics 1998, 225-232, 19.
Magro et al., The role of microvascular injury in the evolution of idiopathic pulmonary fibrosis, Am. J. Clin. Pathol. 2003, 556-567, 119.
Medveczky et al., Classification of herpesvirus saimiri into three groups based on extreme variation in a DNA region required for oncogenicity, J. Virology 1984, 938-944, 52(3).
Nicholas et al., Novel organizational features, captured cellular genes, and strain varibility within the genome of KSHV/HHVB, Monogr. Natl. Cancer Inst. 1998: 79-88, 23.
Nishimura et al., Recombinant human-mouse chimeric monoclonal antibody specific for common acute lymphocytic leukemia antigen, Cancer Res. 1987, 999-1005, 47.
Noble et al., Pulmonary fibrosis: patterns and perpetrators, J. Clin. Invest. 2012, 2756-2762, 122(8).
Northen et al., Clathrate nanostructure for mass spectrometry, Nature 2007, 1033-1036, 449.
Notomi et al., Loop-mediated isothermal amplification of DNA, Nucl. Acids Res. 2000, e63 (7 pgs), 28(12).
Nuovo et al., The distribution of immunomodulatory cells in the lungs of patients with idiopathic pulmonary fibrosis, Mod. Pathol. 2012, 416-433, 25.
Ablashi et al., "Detection of antibodies to Herpervirus saimiri late antigens in human sera," *Intervirology*, vol. 29, No. 4, pp. 217-226 (1988).
Albrecht et al., "Primary structure of the herpesvirus saimiri genome," *J. Virol.*, vol. 66, No. 8, pp. 5047-5058 (1992), NCBI GenBank Dep: Saimiriine herpesvirus 2, complete genome. NC_001350. GenBank Dep. Aug. 1, 2000.
Albrecht et al., "Primary structure of the perhesvirus saimiri genome," *J. Virol.*, vol. 66, No. 8, pp. 5047-5058 (1992).
Chang et al., "Identification of herpesvirus-like DNA sequences in AIDS-associated Kaposi's sarcoma," *Science*, vol. 266, pp. 1865-1869 (1994).
Chen, *Modern Pathology*, vol. 19, pp. 726-737 (2006).
Dolan et al., The genome of Epstein-Barr Virus type 2 strain AG876, *Virology*, vol. 350, No. 1, pp. 164-170 (2006), Epub Feb. 21, 2006, NCBI GenBank Dep: Human Herpesvirus 4, complete genome. NC_009334. GenBank Dep. Apr. 3, 2007.
GenBank, Accession NC_001350 GI: 9625955, Apr. 30, 2000.
Nuovo et al., "A methodology for the combined in situ analyses of the precursor and mature forms of mircoRNAs and correlation with their putative targets," *Nature Protocols*, vol. 4, No. 1, pp. 107-115 (2009).
Nuovo et al., "In situ detection of micro RNAs in paraffin embedded, formalin fixed tissues and the co-localization of their putative targets," *Methods*, vol. 52, pp. 307-315 (2010).
Pierce et al., "Therapeutic Targeting of CC Ligand 21 or CC Chemokine Receptor 7 Abrogates Pulmonary Fibrosis Induced by the Adoptive Transfer of Human Pulmonary Fibroblasts to Immunodeficient Mice," *The American Journal or Pathology*, vol. 170, No. 4, pp. 1152-1164 (2007).
Rezaee et al., "Kaposi's sarcoma-associated herpesvirus immune modulation: an overview", *J. Gen. Virol.* vol. 87, Pt. 7, pp. 1781-1804 (2006); NCBI Gen Bank Dep: Human Herpesvirus 8, complete genome. NC_009333 Gen Bank Dep. Apr. 3, 2007.
Rogers, *Comprative Medicine Biol.*, vol. 65, No. 3, pp. 232-240 (2015).
Smith et al., "In vivo episomal maintenance of a herpesvirus saimiri-based gene delivery vector," *Gene Ther.*, vol. 8, No. 23, pp. 1762-1769 (2001).
Tischer et al., "Osterrieder N. Herpesviruses—a zoonotic threat?", *Vet. Microbiol.*, vol. 140, pp. 266-270 (2010). Doi: 10.1016/j.vetmic. 2009.06.020. Epub Jun. 21, 2009.
Trujillo et al., "TLR9 Differentiates Rapidly from Slowly Progressing Forms of Idiopathic Pulmonary Fibrosis," *Science Trnaslational Medicine*, vol. 2, Issue 57, No. 57ra82, 11 pages (2010).
Watts et al., "RhoA signaling modulates cyclin D1 expression in human lung fibroblasts; implications for idiopathic pulmonary fibrosis," *Respir Res.*, vol. 7, No. 88, pp. 1-14 (2006).
Whitehouse, A., Assessment of infectivity using a Herpesvirus saimiri (HVS) recombinant that expresses HVS-GFP, *Cold Spring Harb Protoc.*, vol. 12, pp. 1520-1523 (2011).
Wiener et al., "Population-Based Risk for Complications After Transthoracic Needle Lung Biopsy of a Pulmonary Module: An analysis of Discharge Records," *Ann Intern Med*, vol. 155, No. 3, pp. 137-144 (2011)—Abstract Only.
Yao et al., "Herpesvirus saimiri encodes a new cytokine, IL-17, which binds to a novel cytokine receptor," *J. Immunol.*, vol. 187, No. 9, pp. 4392-4402 (2011).

MTFRMTSLV-LLLLLSIDCIVKSEITSAQTPRC-LAANNSFPRSVMVTLS   48
||...||||  ||||||:..||....:.|.|  ..:.:.||||:|||.|:
MTPGKTSLVSLLLLLSLEAIVKAGITIPKNPGCPNSEDKNFPRTVMVNLN   50

I--RNWNTSSKRASDYYNRSTSPWTLHRNEDQDRYPSVIWEAKCRYLGCV   96
|  ||.||:.|:|||||||||.||||||..:|||||||||||||:|||:
IHNRNTNTNPKRSSDYYNRSTSPWNLHRNEDPERYPSVIWEAKCRHLGCI   100

NADGNVDYHMNSVPIQQRILVVRKGHQPCPNSFRLEKMLVTVGCTCVTPI   146
||||||||||||||||||:|..:....||||||||||:||:||||||||
NADGNVDYHMNSVPIQQEILVLRREPPHCPNSFRLEKILVSVGCTCVTPI   150

VHNVD   151 (SEQ ID NO: 1)
|| : |.
VHHVA   155 (SEQ ID NO: 2)

FIG. 4A

```
Query  595  AGCTCTTAGTCTACATTGTGAACAATAGGAGTAACGCATGTGCAACCTACAGTCACTAGC
            ||||||||| |  |||| ||| ||||||  || || || || ||||| || ||| ||| ||
Sbjct  526  AGCTCTTAGGCCACATGGTGGACAATCGGGGTGACACAGGTGCAGCCCACGGACACCAGT Query  655  ATCTTCTCTAGCCGAAATGAATTAGGGCAAGGGTTATGCCCTTTGCGCACTACTAGAATC
            |||||||| ||||| ||  || ||  |||||    | | |||||| || || || ||| |||
Sbjct  466  ATCTTCTCCAGCCGGAAGGAGTTGGGGCAGTGTGGAGGCTCCCTGCGCAGGACCAGGATC Query  715  TCTTGTTGGATAGGGACTGAGTTCATGTGGTAGTCTACATTCCCATCAGCATTAACACAT
            ||||| ||||| |||||| |||| ||||||||||||  |||  ||||||||||| | ||
Sbjct  406  TCTTGCTGGATGGGGACAGAGTTCATGTGGTAGTCCACGTTCCCATCAGCGTTGATGCAG Query  775  CCTAAGTAGCGACACTTTGCTTCCCAAATCACAGAAGGATATCTATCTTGATCTTCATTG
            || |||| ||| |||||||||| |||||||||||| |||||||||||||||  | || ||||||
Sbjct  346  CCCAAGTGGCGGCACTTTGCCTCCCAGATCACAGAGGGATATCTCTCAGGGTCCTCATTG Query  835  CGATAGAGAGTCCAAGGAGACGTAGATCTATTGTAGTAGTCTGAAGCCCTT-----TTA
            || | ||||| ||||||| || || |||| ||||||| |||||  | |||  |||
Sbjct  286  CGGTGGAGATTCCAAGGTGAGGTGGATCGGTTGTAGTAATCTGAGGACCTTTTGGGATTG Query  889  GAACTAGTATTCCAGTTACGGATGCTCAAAGTAACCATCACAGACCGTGGGAAGCTATTG
            |  | |||||||| ||||| ||||| |||||| ||||||||||||  | |||||| | |||
Sbjct  226  GTATTGGTATTCCGGTTATGGATGTTCAGGTTGACCATCACAGTCCGGGGGAAGTTCTTG Query  949  ---TTAGCAGCTAAGCATCTTGGGGTTTGTGCGCTGGTTATTTCTGACTTTACTATACAA
               | ||  ||||||| |||  || || ||||  | || |||  ||| |||||
Sbjct  166  TCCTCAGAATTTGGGCATCCTGGATTTCGTGGGATTGTGATTCCTGCCTTCACTATGGCC Query  1006 TCTATGCTCAGCAGC---AGAAGTAACACAAGTGAAGTCTTTCTAAATGTCATAATTACT
            ||  ||||||||||||   ||  ||| ||||  | |||||||| |  ||||| || |
Sbjct  106  TCCAGGCTCAGCAGCAGTAGCAGTGACACCAATGAGGTCTTCCCAGGAGTCATCGTTGTT Query  1063 TCTT 1066  (SEQ ID NO: 3)
            ||||
Sbjct  46   TCTT 43    (SEQ ID NO: 4)
```

FIG. 4B

SEQUENCE LISTING

<160> NUMBER OF SEQ ID NOS: 14

<210> SEQ ID NO 1
<211> LENGTH: 151
<212> TYPE: PRT
<213> ORGANISM: Homo sapiens

<400> SEQUENCE: 1

Met Thr Phe Arg Met Thr Ser Leu Val Leu Leu Leu Leu Ser Ile
1               5                   10                  15

Asp Cys Ile Val Lys Ser Glu Ile Thr Ser Ala Gln Thr Pro Arg Cys
            20                  25                  30

```
Leu Ala Ala Asn Asn Ser Phe Pro Arg Ser Val Met Val Thr Leu Ser
            35                  40                  45

Ile Arg Asn Trp Asn Thr Ser Ser Lys Arg Ala Ser Asp Tyr Tyr Asn
 50                  55                  60

Arg Ser Thr Ser Pro Trp Thr Leu His Arg Asn Glu Asp Gln Asp Arg
 65                  70                  75                  80

Tyr Pro Ser Val Ile Trp Glu Ala Lys Cys Arg Tyr Leu Gly Cys Val
                 85                  90                  95

Asn Ala Asp Gly Asn Val Asp Tyr His Met Asn Ser Val Pro Ile Gln
            100                 105                 110

Gln Glu Ile Leu Val Val Arg Lys Gly His Gln Pro Cys Pro Asn Ser
            115                 120                 125

Phe Arg Leu Glu Lys Met Leu Val Thr Val Gly Cys Thr Cys Val Thr
            130                 135                 140

Pro Ile Val His Asn Val Asp
145                 150

<210> SEQ ID NO 2
<211> LENGTH: 155
<212> TYPE: PRT
<213> ORGANISM: Herpesvirus saimiri

<400> SEQUENCE: 2

Met Thr Pro Gly Lys Thr Ser Leu Val Ser Leu Leu Leu Leu Leu Ser
  1               5                  10                  15

Leu Glu Ala Ile Val Lys Ala Gly Ile Thr Ile Pro Arg Asn Pro Gly
             20                  25                  30

Cys Pro Asn Ser Glu Asp Lys Asn Phe Pro Arg Thr Val Met Val Asn
             35                  40                  45

Leu Asn Ile His Asn Arg Asn Thr Asn Thr Asn Pro Lys Arg Ser Ser
 50                  55                  60

Asp Tyr Tyr Asn Arg Ser Thr Ser Pro Trp Asn Leu His Arg Asn Glu
 65                  70                  75                  80

Asp Pro Glu Arg Tyr Pro Ser Val Ile Trp Glu Ala Lys Cys Arg His
                 85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
            115                 120                 125

Cys Pro Asn Ser Phe Arg Leu Glu Lys Ile Leu Val Ser Val Gly Cys
            130                 135                 140

Thr Cys Val Thr Pro Ile Val His His Val Ala
145                 150                 155

<210> SEQ ID NO 3
<211> LENGTH: 472
<212> TYPE: DNA
<213> ORGANISM: Homo sapiens

<400> SEQUENCE: 3
agctcttagt ctacattgtg aacaatagga gtaacgcatg tgcaacctac agtcactagc     60
atcttctcta gccgaaatga attagggcaa gggttatgcc ctttgcgcac tactagaatc    120
tcttgttgga tagggactga gttcatgtgg tagtctacat tcccatcagc attaacacat    180
cctaagtagc gacactttgc ttcccaaatc acagaaggat atctatcttg atcttcattg    240
cgatagagag tccaaggaga cgtagatcta ttgtagtagt ctgaagccct tttagaacta    300
```

```
gtattccagt tacggatgct caaagtaacc atcacagacc gtgggaagct attgttagca      360
gctaagcatc ttggggtttg tgcgctggtt atttctgact ttactataca atctatgctc      420
agcagcagaa gtaacacaag tgaagtcttt ctaaatgtca taattacttc tt              472

<210> SEQ ID NO 4
<211> LENGTH: 484
<212> TYPE: DNA
<213> ORGANISM: Herpesvirus saimiri

<400> SEQUENCE: 4
agctcttagg ccacatggtg gacaatcggg gtgacacagg tgcagcccac ggacaccagt       60
atcttctcca gccggaagga gttggggcag tgtggaggct ccctgcgcag gaccaggatc      120
tcttgctgga tggggacaga gttcatgtgg tagtccacgt tcccatcagc gttgatgcag      180
cccaagtggc ggcactttgc ctcccagatc acagagggat atctctcagg gtcctcattg      240
cggtggagat tccaaggtga ggtggatcgg ttgtagtaat ctgaggacct tttgggattg      300
gtattggtat tccggttatg gatgttcagg ttgaccatca cagtccgggg gaagttcttg      360
tcctcagaat ttgggcatcc tggatttcgt gggattgtga ttcctgcctt cactatggcc      420
tccaggctca gcagcagtag cagtgacacc aatgaggtct cccaggagt catcgttgtt        480 tctt                                                                   484

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
ctctaagcac aggggcacag                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
ctacgcagaa gtcggaagcc                                                   20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
gccgcctcag aattttagca                                                   20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 8
ctctgcgtga agcacagtgc                                                    20

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
tatttacacc cagtacctac aaaaatt                                            27

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
taaataaata tgtagtgt                                                      18

<210> SEQ ID NO 11
<211> LENGTH: 1838
<212> TYPE: DNA
<213> ORGANISM: Herpesvirus saimiri

<400> SEQUENCE: 11
gaattccaaa cagacataat acctaatgga acagtgttga aactacttgg aagaacacta        60
gagggtgcga gcgtatgtgt taacgtgttt ggacaaagaa attactttta tgttaaagtt       120
ccggaaggtg gcaacataac ctatcttatg aaacaagctt tgaatgaaaa atttagccca       180
tcttgtgcat accaaactga agcagtaaaa aagaagatac tatctagata tgatccaaaa       240
gaacatgatg ttttttaaagt gacagtgtct tcttctcttt ctgtttataa aatatcagat       300
tctttagtgt ctaatggttg tgaagttttt gaaacaaatg tagatgctat aagaagattt       360
gtaattgata caacttctc tacatttggt tggtacacat gtaagtctgc atgtcctcga        420
atcacaaata gagactctca tactgacatt gagtttgact gcgggtacta tgacttggaa       480
tttcatgcag atagaacaga atggccacct tacaacataa tgtcttttga tatagaatgt       540
ataggagaaa aaggatttcc gtgtgcaaaa aatgaagaag atttaataat tcagatttca       600
tgtgtgtttt ggcacgctgg gacgcttgat gcaactagaa atatgctatt atctttaggg       660
acgtgctcag ctgttgaaaa tactgaagtt tatgagtttc ccagtgaaat agacatgctg       720
catgggtttt tttcattaat tagagacttt aatgttgaaa taattactgg ttataatatt       780
tctaactttg acttacccta tctaattgat agagctactc aaatttataa tataaagcta       840
tctgattatt caagagttaa aacagggtct attttttcaag ttcatacgcc aaaagataca       900 ggaaagggt tcatgagatc tgtctctaaa ataaaaattt caggaattat agcaattgac       960
atgtacattg tgtgcaaaga caaactcagt ctgtctaatt acaagcttga tactgttgct      1020
aatcactgca ttagtgcaaa aaaagaagat gtgtcttaca agatatcat gcctcttttt      1080 atgtctggac ctgaaggcag agctaagata ggactatact gtgtaataga ttctgttctt      1140
gtgatgaaac ttttgaaatt ttttatgatt catgttgaaa tttctgagat agcgaaactg      1200

```
gctaaaatcc ccacgagaag agttcttaca gatgggcaac aaataagagt tttttcttgt      1260
ctgcttgcag cagctcgtgc agaaaactat atactgcctg tgtcaaatga tgtcaatgcg      1320
gatgggtttc agggagctac cgtcataaac ccaattcctg gattttataa caatgctgta      1380
ttagtagtag actttgctag cctgtatcct agtatcatac aagctcataa tctatgctac      1440
tccactctta taccccacca tgctttacac aactaccctc acttaaaatc tagtgactat      1500
gagactttta tgctcagttc tggacctata cactttgtga aaaaacacat tcagacatct      1560
cttctatcta ggcttttaac tgtgtggctt tctaagcgaa aggctattag caaaagctt      1620 gctgaatgtg aagacctaga cactaaaact attctagata acagcaact cgctattaag      1680 gtaacctgta atgctgtgta tgggtttaca ggagttgcgt caggcttgct gccatgcata      1740
agcattgcag agaccgttac tctccaaggc cggacgatgc tagaaaaatc aaaaatattt      1800
atagaagcaa tgacacctga tacacttcaa gaggatcc                             1838

<210> SEQ ID NO 12
<211> LENGTH: 1395
<212> TYPE: DNA
<213> ORGANISM: Herpesvirus saimiri

<400> SEQUENCE: 12
gaattcggtc cggagcggtc tctacagacg ccccagactc tcagctgtcc cccggtgccg        60
gcgcggcgcc gctgccccccc gcggctgggg agctagggcc gctcaaagcg ggtcccctcc       120
cccggccgcc tggggatctg ctaggcagct gctctgcagc ccagcctagg gggcttcagc       180
ggggcatagc tccacagcgc aagggtcccc gggcttcaca ctcggtgggc aggcaaggga       240
cccttcccgc tgacggctgc aaactctggc tagccggggg aactctgtgc tggagagata       300
ggggcgcgca agcccccatc acagggctcc ggctggcagg gctcgccctc agggctgcac       360
agcagtctag cctaggggc ttcagccagg gctagctcca aaaccctcag gtccccagac       420
ttcaaacttg gtgggcacgt agaggaccct tcccgctgac tctccacgcc gcctcagaat       480
tttagcaccc ggcgctgcgg agccgggagc cagcaagccc cccgctgggg tctcggctgc       540
tgctgctcgg gggcctgggg ctgggaggc ggctgcaggg gctgcatgca ctgtgcttca       600
cgcagaggtc ggggggggagc ccagctacgc gccccccacg ctgcagggcg ctgcgctggg       660
ctctggggct ggggggggctt gaacagttgt gggaccctta tctagcagc gcctcggcct       720 agccagggct ctggggactg gctctaagca caggggcaca gcgccccgg gcctgcggtg       780 gcctggggac acaacaggag ctctggaatc tcagcccaga ggggtgcggg gctgctcaat       840
cccttccccc tccctccgca gccgctcgct gctcgccctg ccccccgagc tcgctctagc       900
cacgcccagg acatttttcc agctgcccag cgcccactgc ttggggcccc cttccccct       960 ctttgcctac caagttatcc cccgggggga aaatcagtgg gggctgcata gagctctccg      1020
caggcggccg ctcgctcccc gggcgtccgc agcctctcgg ggggcctctg gggcgcccgg      1080
cgggagcccc cgtgcggggc tccggtccct ctagtgcaca agcagactct agcccccctcc      1140 cccagtacac agagcccagc agcccccggc cgcggcgccc gtgcagcgcc cggcagcttg      1200 cttcggttt tctcgccccga ccccccgct gggctgctgg gggcagagcc gcggggccgc      1260
aggcgggtgc cctagagtct caagcatctt ctgactccga gtggagggga tctgtcccgc      1320
tacgggctcg ccctgggccg gggtctgcag agaccgctcg cggcggccat tttgtgtgcc      1380
acgcatggcg gtacc                                                      1395
```

<210> SEQ ID NO 13
<211> LENGTH: 865
<212> TYPE: DNA
<213> ORGANISM: Herpesvirus saimiri

<400> SEQUENCE: 13

```
ggtaccaaac caacaagcca gaacttagat taaactttt tatttaaaag aaaaagataa      60
tcaagttttt ggttttagc gaaatgttac ttttcaaaat taagatagct cttagtctac     120
attgtgaaca ataggagtaa cgcatgtgca acctacagtc actagcatct tctctagccg    180
aaatgaatta gggcaagggt tatgcccttt gcgcactact agaatctctt gttggatagg    240
gactgagttc atgtggtagt ctacattccc atcagcatta acacatccta agtagcgaca    300
ctttgcttcc caaatcacag aaggatatct atcttgatct tcattgcgat agagagtcca    360
aggagacgta gatctattgt agtagtctga agcccttta gaactagtat tccagttacg     420
gatgctcaaa gtaaccatca cagaccgtgg gaagctattg ttagcagcta agcatcttgg    480
ggtttgtgcg ctggttattt ctgacttac tatacaatct atgctcagca gcagaagtaa     540
cacaagtgaa gtctttctaa atgtcataat tacttcttta aattatctat acatgtataa    600
acagataggc ttgctatggt ttacactaaa tgaatgtttg tttatatact ttagagtctt    660
ttatattgat acaaacttct tgctgccata ttttgctagt aaaatacagg acaccaata     720
ctatacagaa acatttttat ttaagatttg catttcagac actaagttat agcaaacaag    780
taatattgca atacacaaag catttatttt agtatgataa acacattcca acagtaattt    840
atggagatga actagtcttt ctaga                                          865
```

<210> SEQ ID NO 14
<211> LENGTH: 1244
<212> TYPE: DNA
<213> ORGANISM: Herpesvirus saimiri

<400> SEQUENCE: 14

```
tctagagggc ttgaacagtt gtgggaccct tactctagca gcgcctcggc ctagccaggg      60
ctctggggac tggctctaag cacaggggca cagcgccccc gggcctgcgg tggcctgggg    120
acacaacagg agctctggaa tctcagccca gaggggtgcg gggcggtcgc gagggtctag    180
cgcctcgaaa ccggctcgga gcacaagcag actctagccc cctcccctag tacacagagc    240
ccagcaggca gctacagccg ctcaacgcga gtccctcccc ttgctcaagc tctttagtac    300
acttttgtc ttttatacaa tagttttatt actgcatagt ataagacatt tactgcagca    360
ctatgtgatt cactttgatt cttttacatt ttttaaaca taattactag cattaaacca    420
attatgatta atagcaaaac aataataact agcagcaata ggatagttac agaacagtct    480
gtgcatttgt caccttcttg ctcgtgttca ctgtgcaggc ttccgacttc tgcgtagaca    540
tgttcttcac ttcctgctcc tccgcagcca ctgacacgta ctgctgataa gcctactggg    600
gtgcttaaat gtgatgagct ccgtgagcca gatggtgttg gtaagcctac tgctcccgat    660
agtgctgttg gtcttcctgg gcatccgctt tcttgcactg ggtggccaag caagcagtag    720
ggattataag gcccaagggg ccctgcattt aaaagcgtta caggtaagta tggtgtaggt    780
ccatcatctc catcacttct ttcatcagta ttgtgtggag gatctccgtt gctttcatcg    840
ttttcttgtg ggtctccttc acctagacct cttgccattt tcttacacgt ctaagcttca    900
gtttgtttag ctgattcttg tagtgttgtc tgtcttgcta attcttatat agtagcttgt    960
tacttcttgg aaagtccagc aagatggtgt cctgtttaac agcttgacca catgttttac   1020
```

```
aggacttaaa aatttaaatt ttaacctttt gacaaagagc aaaaatgaat aaaaagctac    1080
agctgtatga ctcttatctt ttaacatagt agcaatgcac ttacgtgtta acttatttta    1140
ttataagttg atgcttgcta ttgtagtgct tatagcagct tttatatcag cttttagtag    1200
ttattgctag ctttatctag ctttgctctc aatgagctgg atcc                     1244
```

DIAGNOSIS AND TREATMENT OF VIRAL DISEASES

1. CROSS REFERENCE TO RELATED APPLICATIONS

This application is a continuation of U.S. patent application Ser. No. 15/439,495, filed on Feb. 22, 2017, which is a continuation of U.S. patent application Ser. No. 14/759,687, now U.S. Pat. No. 9,617,607, issued Apr. 11, 2017, which is a National Stage Entry of PCT/US14/10675, filed Jan. 8, 2014, which is a continuation-in-part of U.S. patent application Ser. No. 14/080,644, filed Nov. 14, 2013, now abandoned, which is a continuation-in-part of U.S. patent application Ser. No. 13/920,964, filed Jun. 18, 2013, now abandoned, which claims the benefit under 35 U.S.C. § 119(e) of U.S. Provisional Application No. 61/750,104, filed Jan. 8, 2013, the contents of all of which are incorporated herein in their entirety by reference thereto.

2. REFERENCE TO SEQUENCE LISTING, TABLE OR COMPUTER PROGRAM

The instant application contains a Sequence Listing which has been submitted electronically in ASCII format and is hereby incorporated by reference in its entirety. Said ASCII copy, created on Nov. 29, 2013, is named ENZ-109 (CIP)_SL.txt and is 13,246 bytes in size.

Herpesviruses are a family of very large double stranded DNA viruses ranging from 125 KB to 240 KB in length. See, e.g., Davison A J. Comparative analysis of the genomes. In: Arvin et al., editors. Human Herpesviruses: Biology, Therapy, and Immunoprophylaxis. (Cambridge: Cambridge University Press; 2007) Chapter 2. Available from: http://www.ncbi.nlm.nih.gov/books/NBK47439. Phylogenetically the Herpesvirus family is divided into three groups: α, β and γ. Although initially grouped on the basis of different cell tropisms and biological properties, further studies have shown that nucleic acid sequence divergence also separates these groups of Herpesviruses. α-Herpesviruses that are known to infect humans are Herpes simplex 1 (HSV1), Herpes simplex 2 (HSV2) and Herpes zoster (VSV), the causative agent of both chicken pox and shingles. A representative human pathogen of the β-Herpesviruses is human Cytomegalovirus (CMV). The third group, the γ-Herpesviruses, are divided into two subgroups, Lymphocryptovirus and Rhadinovirus. An example of the former is Epstein Barr Virus (EBV), which causes mononucleosis and certain lymphomas, and examples of the latter are Herpesvirus saimiri (HVS), a monkey virus, MHV68 (a mouse virus) and human Herpesvirus 8 (HHV8, KSHV), which is associated with the development of Kaposi's sarcoma. Herpesvirus infections are associated with a "latent" period in which the virus is dormant for long periods between activations. Certain cell types, such as neurons, B-cells and T-cells are associated with the latent virus. The HVS virus is endemic but non-pathogenic in squirrel monkeys. HVS infection of other monkey species induces lymphomas, and in vitro infection of human T-cells can lead to cellular transformation. See Biesinger et al. (1992) Proc. Nat Acad. Sci (USA) 89; 3116-3119. HVS itself has been further subdivided into three groups: A, B and C, but the differences are based strictly on a small region in the left end of the viral genome responsible for transformation (Medveczky et al., 1984 J. Virol. 52; 938-944) while strong conservatism is seen within the sequences of the rest of the genomes of each group. See Ensser et al. (2003) Virology 314:471-487. Although HVS infection in humans was known (Ablashi et al. (1988) Intervirology 29(4):217-226), until the present disclosure, there was no evidence that HVS could induce disease in humans. See Estep et al. (2010) Vaccine 285; 878-884.

Idiopathic pulmonary fibrosis ("IPF") is a specific form of chronic, progressive fibrosing interstitial pneumonia of unknown cause that typically presents in adults over 50 years of age. The characteristic histology of IPF includes sub-pleural fibrosis with many alveolar-based sites of fibroblast proliferation and dense scarring, alternating with areas of normal lung tissue. Scattered interstitial inflammation occurs with lymphocyte, plasma cell, and macrophage and/or dendritic cell infiltration. Honeycombing—lung fibrosis characterized by multiple cystic spaces located at the bases of the lungs—occurs in all patients and increases with advanced disease. The result is deteriorating respiratory function and death from respiratory failure. For recent reviews on this disease see Raghu et al. (2011) Am. J. Respir. Crit. Care Med. 183:788-824 and Noble et al. (2012) J. Clin. Invest. 122; 2756-2762.

Symptoms and signs of IPF typically develop over 6 months to several years and include shortness of breath upon physical exertion (dyspnea), non-productive cough, bibasilar inspiratory (Velcro) crackles on chest examination, and in some patients, clubbing of the fingers. However, IPF may be misdiagnosed because its symptoms are similar to those of more common diseases, such as bronchitis, asthma and heart failure. Currently, diagnosis of IPF requires at least high-resolution computed tomography (HRTC), and may also include pulmonary function tests and/or surgical lung biopsy. See Raghu (2011).

Most patients have moderate to advanced clinical disease at the time of diagnosis. Normal partial pressure of oxygen in arterial blood and fewer fibroblastic foci on biopsy at presentation predict a better prognosis, while advanced age, poor pulmonary function at presentation and severe dyspnea predict a worse prognosis. Although some patients demonstrate a gradual progression of the disease and others have an accelerated decline, the clinical course eventually leads to death, with the median survival being less than 3 years from diagnosis.

Over the years, efforts have been made to identify treatments to reverse or halt the progression of IPF. For example, the similarity of IPF to autoimmune diseases has led to attempts to treat IPF using immunomodulatory compounds, e.g., corticosteroids, etanercept and the like, which were not proven to be effective and, indeed, may worsen the symptomatology. See Papiris et al. (2012) Am. J. Respiratory and Crit Care Med 185(5):587-588. Other pharmacological therapies that proved to be ineffective have included, e.g., anticoagulants, phosphodiesterase inhibitors, and mucolytic agents. See, e.g., Adamli et al. (2012) Drug Design, Development and Therapy 6; 261-272; Cottin (2012) Eur Respir. Rev 21; 124, 161-167; Rafii et al., (2013) J Thoracic Dis. 5; 48-73.

The efforts to develop therapies for IPF have been largely unsuccessful, in part because the cause of the disease was not known. Accordingly, therapies have been aimed at treatment of certain complications and comorbid conditions (e.g., pulmonary hypertension and/or asymptomatic gastroesophageal reflux), supportive therapies such as oxygen therapy for hypoxemia, pulmonary rehabilitation and antibiotics for pneumonia, and therapies directed to easing the debilitating fibrotic manifestations of IPF. The drastic nature of the disease is reflected by the fact that in some cases, lung transplantation for otherwise healthy IPF patients is recommended.

Attempts to elucidate the underlying cause of IPF have led to the search for markers, e.g., differences in protein and/or mRNA expression that might distinguish patients with IPF from normal subjects and/or patients with other pulmonary diseases. Certain protein profiling studies of patients with IPF compared to normal controls have shown a lack of significant differences between patients and controls in expression of inflammatory markers, e.g., IL-17A, IL-23, RANTES. See Stin et al. (2013) Ann Thoracic Med. 8; 38-45; Ebina et al. (2011) Pulmonary Medicine Article ID 916486. Another study of in situ expression of cytokines surprisingly showed high levels of expression of IL-17 in actively growing lung epithelial cells in IPF patients, which type of cell was not previously associated with IL-17 expression. See Nuovo et al. (2012) Mod. Pathol. 25; 416-433.

Viruses have also been investigated as potential causative agents of IPF. A number of different Herpesvirus types have been identified as being present in the lungs of IPF patients, and antibodies to Herpesviruses have been found in IPF patients. These Herpesviruses include Herpes simplex 1 (HSV1), cytomegalovirus (CMV) (antibodies), human herpes virus 8 (HHV8) and Epstein Barr Virus (EBV), which appeared to be strongly associated with IPF. See, e.g., Yonemaru et al. (1997) Eur Resp J 10:2040-45; Magro et al. (2003) Am J Clin Pathol. 119:556-567; Egan et al. (1995) Thorax 50:510-513; Stewart et al. (1999) Am J. Resp. Crit. Care Med. 159:1336-41; Tang et al., 2003 J. Clin. Microbiol. 41; 2633-2640. A further problem with assigning EBV as a causative factor is that by the age of 10, 95% of the population has been infected by EBV. See Kutok et al. (2006) Annu. Rev. Pathol. 375-404. As such, even if there were a connection between EBV and IPF, detection of EBV in a clinical sample has little predictive or diagnostic value. Thus, it has been difficult to establish a consistent correlation between the presence of a particular Herpesvirus type and IPF in humans. See, e.g., Zamo et al. (2004) Sarcoidosis vasculitis and Diffuse Lung Diseases 22; 123-128 (failure to detect EBV in IPF patients); Woolton et al. (2011) Am J. Resp. Crit. Care Med. 183:1698-1702 (finding HSV in only 1/43 samples and EBV in 2/43 samples from IPF patients); Dworniczak et al. (2004) J. Physiol. Pharmacol., 55 (Suppl. 3) 67-75 (finding similar incidence of CMV in a comparison of 16 IPF and 16 normal patients).

Nevertheless, the identification of Herpesviruses in clinical specimens has spurred the investigation of the use of traditional antiviral reagents to slow or stop the progress of IPF. Administration of valacyclovir to two patients with IPF showed mixed results. See Tang et al. (2003) J. Clin. Microbiol. 41; 2633-2640. Administration of ganciclovir to a group of IPF patients with advanced disease also showed mixed results, with 8 patients showing some improvement and 6 patients suffering further deterioration. See Egan et al. (2011) Pulmonary Medicine 2011. Lastly, a randomized multicenter clinical trial of interferon-γ showed no increase in longevity as a result of treatment. See King et al. (2009) Lancet 374(9685):222-228. Accordingly, these results do not provide support for the use of traditional antiviral reagents for treatment of IPF.

As previously described in U.S. patent application Ser. No. 13/920,964, filed Jun. 18, 1013, it has been discovered that Herpesvirus saimiri, a herpesvirus that is endemic and nonpathogenic in squirrel monkeys, and which was previously unknown to be associated with any human disease, causes or is associated with IPF. Specifically, the inventors discovered that 22 out of 22 lung tissue samples from IPF patients showed the presence of Herpesvirus saimiri DNA, while 25 out of 25 non-IPF samples had a complete absence of the virus DNA. This discovery and the fact that herpesviruses are known to cause human disease have led to the search for an association between HVS infection and other human diseases.

There remains a need for effective therapeutic regimens to stop progression or even reverse the course of diseases such as IPF that are associated with HVS infection in patients. There also remains a need for early detection and monitoring of diseases such as IPF that are associated with HVS infection in patients.

3. SUMMARY

The present disclosure relates to methods of diagnosing or prognosticating a viral disease in a patient comprising a step of detecting the presence of a virus-specific element from a virus in a clinical sample from said patient. In various embodiments, the virus-specific element is selected from a nucleic acid, a protein or a peptide derived from a virus-specific protein.

In various embodiments, the present disclosure relates to methods of identifying in vitro a therapeutic agent for the treatment of a viral disease, comprising the steps of (a) exposing a virus culture to said agent; (b) measuring the propagation of said virus culture; and (c) comparing said propagation measured in step (b) with the propagation of a virus culture that has not been exposed to the agent, wherein propagation measured in step (b) that is lower than propagation of a virus culture that has not been exposed to the agent identifies a therapeutic agent for the treatment of said viral disease.

In still other embodiments, the present disclosure relates to a method of treating a patient suffering from a viral disease comprising administering to the patient an effective amount of an agent that inhibits replication of a virus, an effective amount of an agent that down-regulates expression of a virus-specific protein, an antagonist of a viral protein or a neutralizing agent that blocks activity of a viral protein. In certain embodiments, agent is an antagonist, and the antagonist is an antibody to virus-specific IL-17.

In various embodiments, the present disclosure relates to kits for diagnosing a viral disease in a patient comprising (a) a reagent for carrying out amplification of a nucleic acid sequence; (b) a primer comprising a sequence complementary to a sequence in one strand of the viral genome; and (c) a primer comprising a sequence identical to a sequence in said strand of the viral genome, wherein said primers are capable of amplifying a nucleic acid of said virus when said nucleic acid is present.

In specific embodiments, the viral disease is idiopathic pulmonary fibrosis. In other embodiments, the viral disease is a lymphoproliferative disease or cancer, such as Castleman's disease in patients not suffering from AIDS, a thymoma, a lymphoma, or a sarcoma.

Accordingly, in various embodiments, the present disclosure relates to methods of detecting the presence of viral target sequences in a human clinical sample comprising the steps of: (a) providing (i) a human clinical sample suspected of having a viral infection, (ii) a labeled nucleic acid probe comprising one or more sequences derived from Herpesvirus saimiri or a related virus, (b) contacting the clinical sample with the labeled nucleic acid probe, (c) allowing hybridization to take place between the labeled nucleic acid probe and the viral target sequences in the clinical sample, if present, and (d) detecting hybridization of the nucleic acid probe to the viral target sequences in the clinical sample. In certain embodiments, the viral target sequences are from a patient suffering from idiopathic pulmonary fibrosis. In other embodiments, the viral target sequences are from a patient suffering from Castleman's disease, a lymphoma, a thymoma or a sarcoma.

In additional embodiments, the present disclosure relates to a method of diagnosing Castleman's disease, a lymphoma, a thymoma or a sarcoma in a human patient comprising (a) providing (i) a human clinical sample suspected of having Castleman's disease, a lymphoma, a thymoma or a sarcoma, (ii) a labeled nucleic acid probe comprising one or more sequences derived from Herpesvirus saimiri or a related virus, (b) contacting the clinical sample with the labeled probe, (c) allowing hybridization to take place between the labeled nucleic acid probe and the viral sequences in the clinical sample, if present, and (d) detecting hybridization of the nucleic acid probe to the viral sequences in the clinical sample, thereby diagnosing the patient as having Castleman's disease, a lymphoma, a thymoma or a sarcoma.

In still other embodiments, the present disclosure relates to a method of diagnosing idiopathic pulmonary fibrosis in a human patient comprising (a) providing (i) a human clinical sample suspected of having IPF, (ii) a labeled nucleic acid probe comprising one or more sequences from Herpesvirus saimiri or a related virus, (b) contacting the clinical sample with the labeled nucleic acid probe, (c) allowing hybridization to take place between the labeled nucleic acid probe and viral sequences in the clinical sample, if present, and (d) detecting hybridization of the nucleic acid probe to the viral sequences in the clinical sample, thereby diagnosing the patient as having idiopathic pulmonary fibrosis.

It should be noted that the indefinite articles "a" and "an" and the definite article "the" are used in the present application to mean one or more unless the context clearly dictates otherwise. Further, the term "or" is used in the present application to mean the disjunctive "or" or the conjunctive "and."

All publications mentioned in this specification are herein incorporated by reference. Any discussion of documents, acts, materials, devices, articles or the like that has been included in this specification is solely for the purpose of providing a context for the present disclosure. It is not to be taken as an admission that any or all of these matters form part of the prior art or were common general knowledge in the field relevant to the present disclosure as it existed anywhere before the priority date of this application.

The features and advantages of the disclosure will become further apparent from the following detailed description of embodiments thereof.

4. BRIEF DESCRIPTION OF THE FIGURES

Figure 1B:
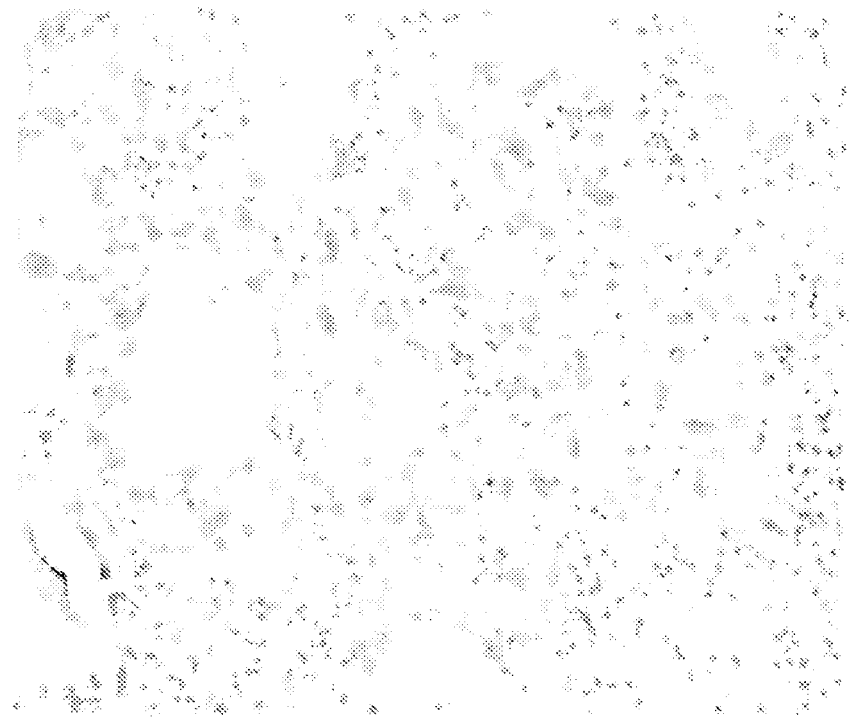

FIGS. 1A-1B. Lung tissue samples from an IPF or lung cancer patient stained with Herpesvirus saimiri-specific probes. FIG. 1A provides a lung tissue specimen from an IPF patient hybridized with a Herpesvirus saimiri transformation-associated protein ("STP") specific probe. FIG. 1B provides a lung tissue specimen from a lung cancer patient hybridized with the STP probe.

Figure 2A:
Figure 2B:
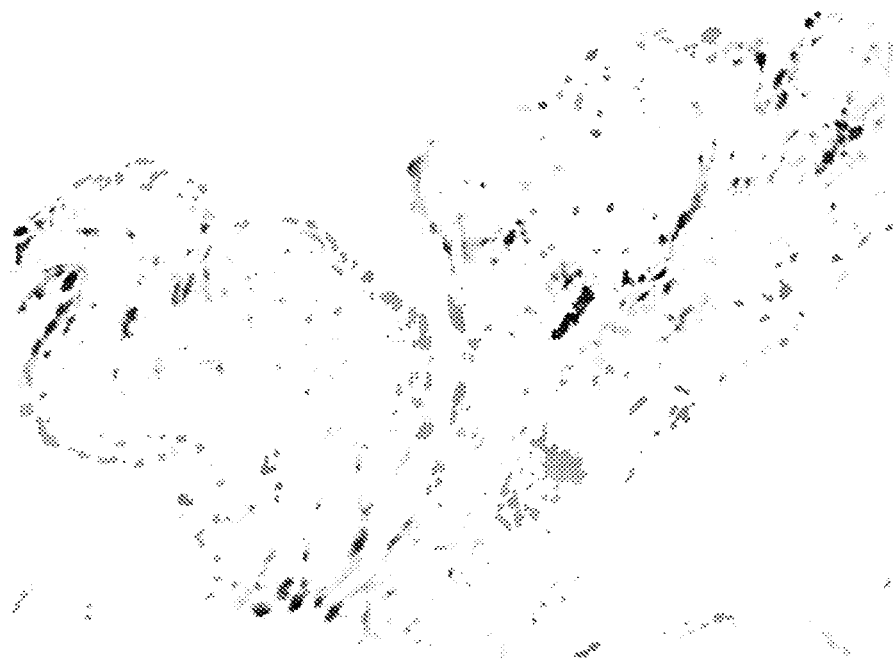

FIGS. 2A-2B. Lung tissue sample from an IPF patient stained with Herpesvirus saimiri-specific probes. FIG. 2A provides a lung tissue specimen from an IPF patient hybridized with a Herpesvirus saimiri STP-specific probe. FIG. 2B provides a lung tissue specimen from an IPF patient hybridized with a Herpesvirus saimiri Terminal region ("TER") probe.

Figure 3A:
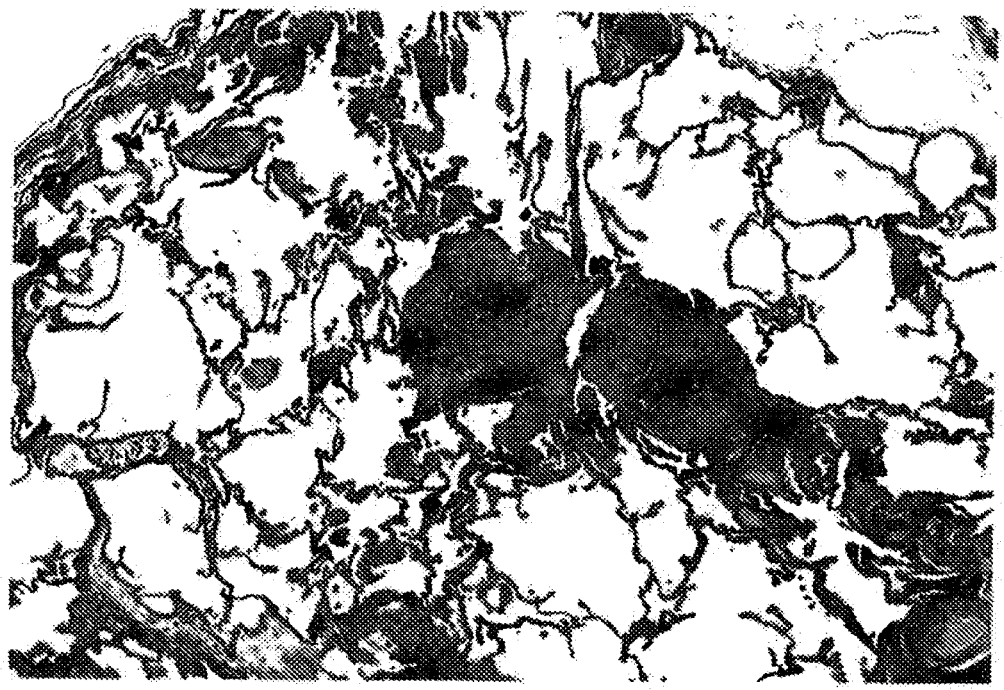
Figure 3B:
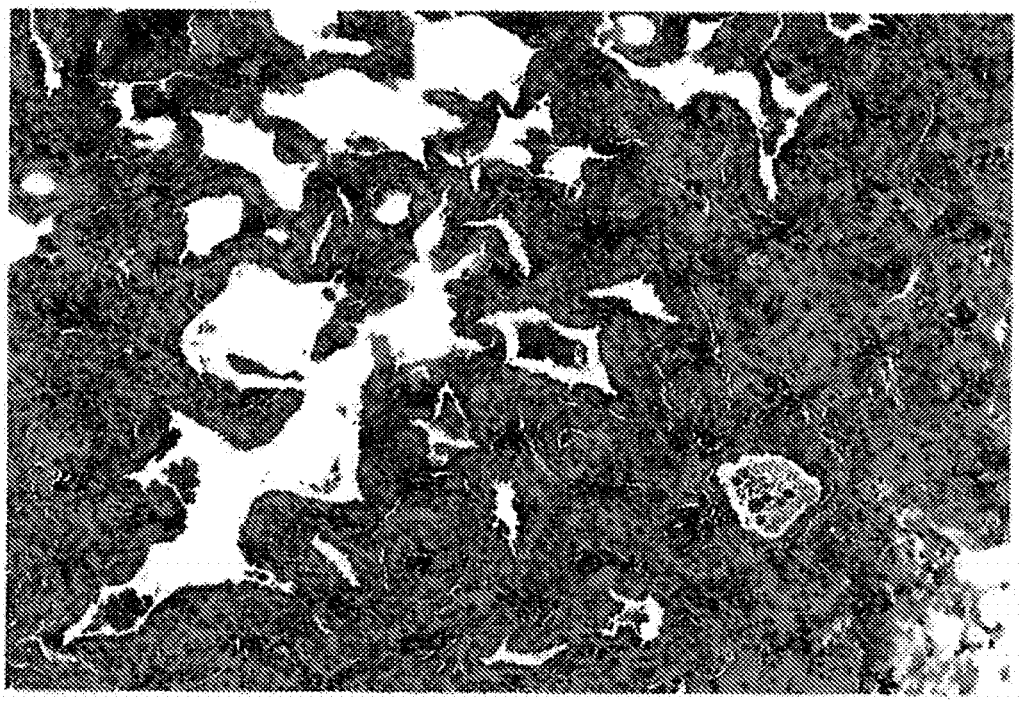
Figure 3C:
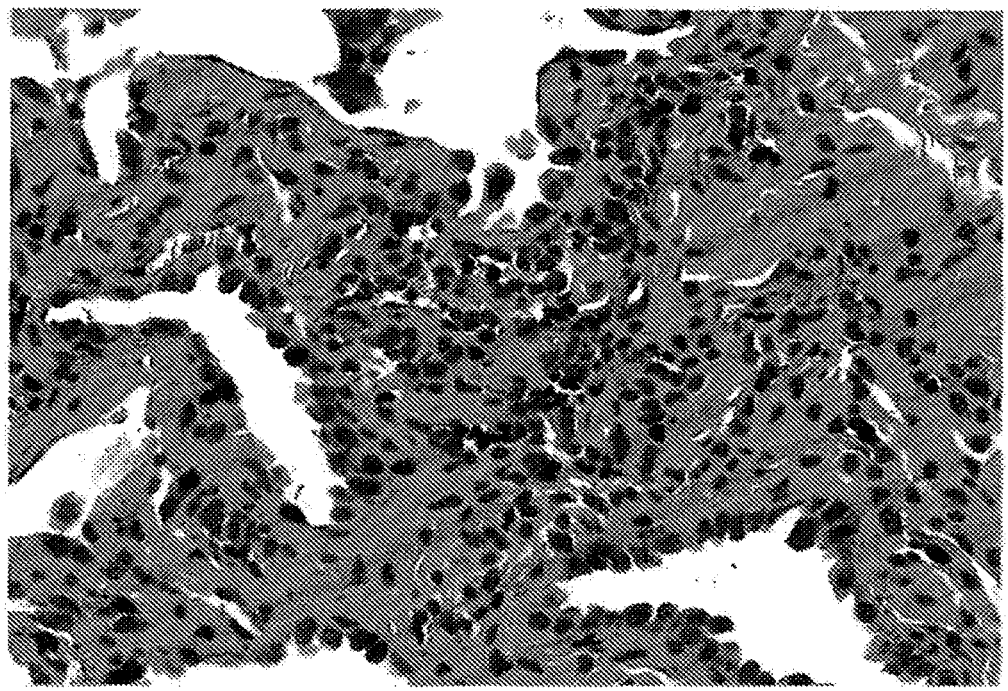
Figure 3D:
Figure 3E:
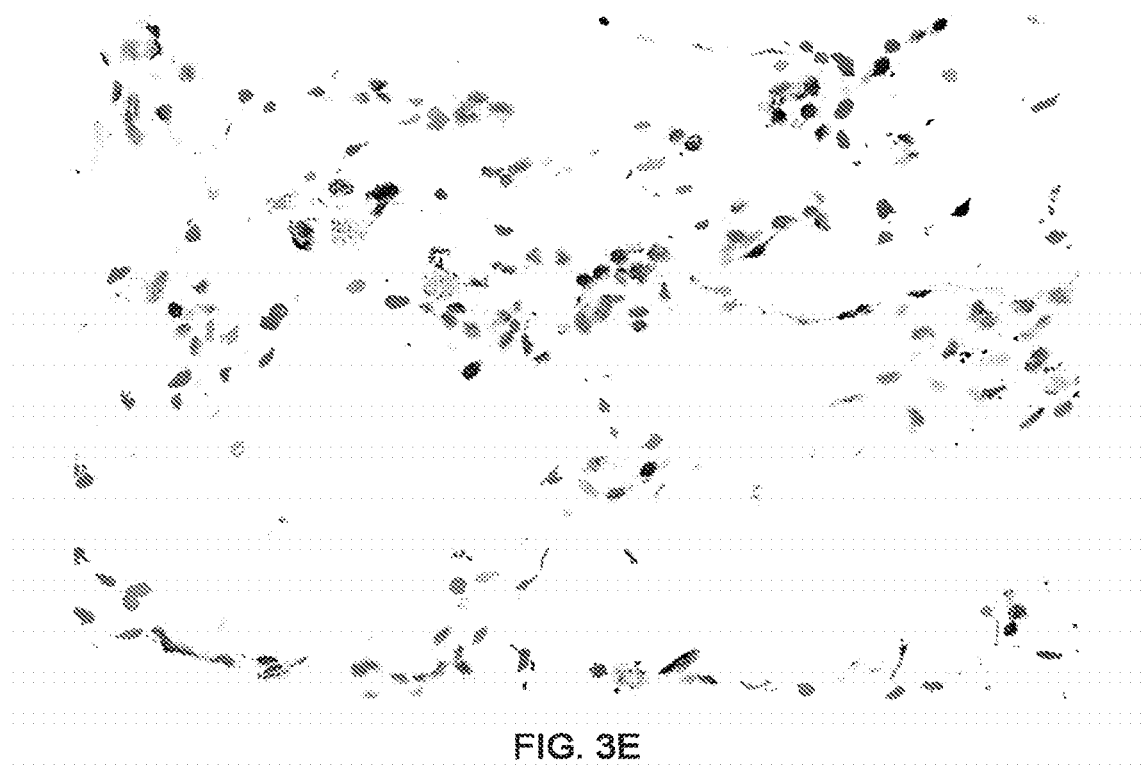
Figure 3F:
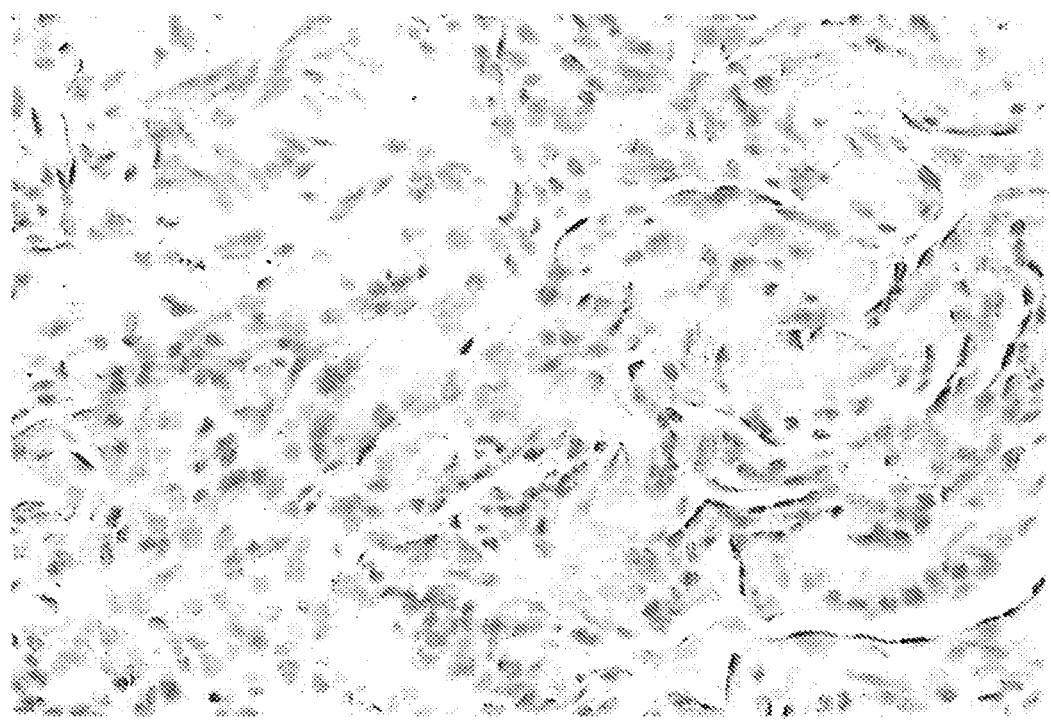
Figure 3G:
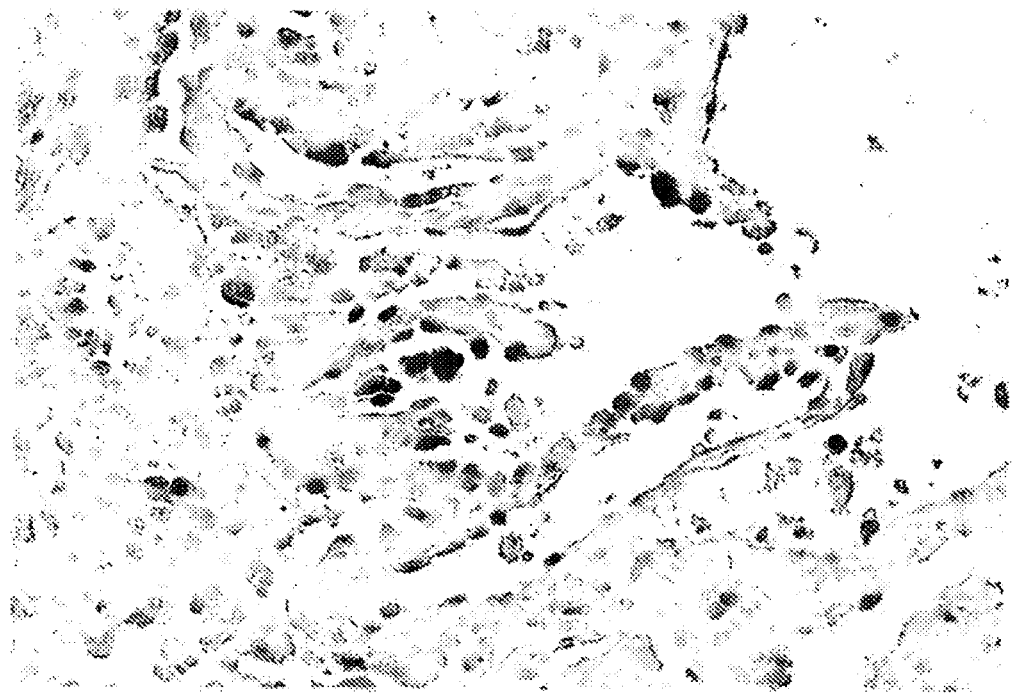
Figure 3H:
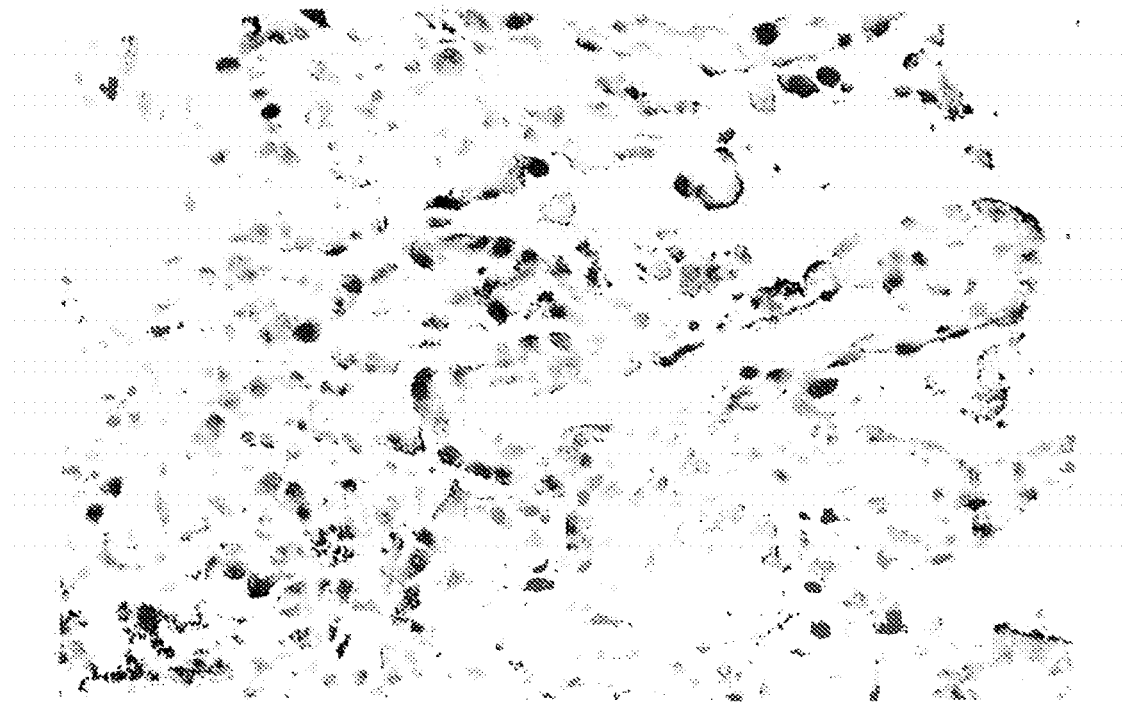

FIGS. 3A-3H. Correlation of IPF histopathology and Herpesvirus saimiri distribution in lung tissue. FIG. 3A provides a correlation of IPF histopathology and Herpesvirus saimiri distribution in a lung tissue specimen from an IPF patient stained with hematoxylin and eosin at 25× magnification. FIG. 3B provides the lung tissue sample from FIG. 3A at 100× magnification. FIG. 3C provides the tissue specimen of FIG. 3A at 400× magnification. FIG. 3D provides a correlation of IPF histopathology and Herpesvirus saimiri distribution in a lung tissue specimen from an IPF patient stained with blue (virus) and nuclear fast red (counterstain) Herpesvirus saimiri-specific probes at 100× magnification. FIG. 3E shows unremarkable lung tissue adjacent to an area of IPF. FIG. 3F provides a lung tissue specimen from a patient suffering from interstitial pneumonitis of known etiology (measles virus) stained with Herpesvirus saimiri STP probes. FIG. 3G provides a lung tissue specimen from an IPF patient stained with Herpesvirus saimiri STP probes at 400× magnification. FIG. 3H provides a lung tissue specimen from an IPF patient stained with Herpesvirus saimiri TER probes at 400× magnification.

FIGS. 4A-4B. Nucleotide and protein sequence comparisons of human IL-17 and Herpesvirus saimiri IL-17. FIG. 4A provides a comparison of the amino acid sequences of human IL-17 (SEQ ID NO:1) and Herpesvirus saimiri IL-17 (SEQ ID NO:2). FIG. 4B provides a comparison of the nucleotide sequences of the gene encoding human IL-17 (SEQ ID NO:3) and the gene encoding Herpesvirus saimiri IL-17 (SEQ ID NO:4).

Figure 5A:
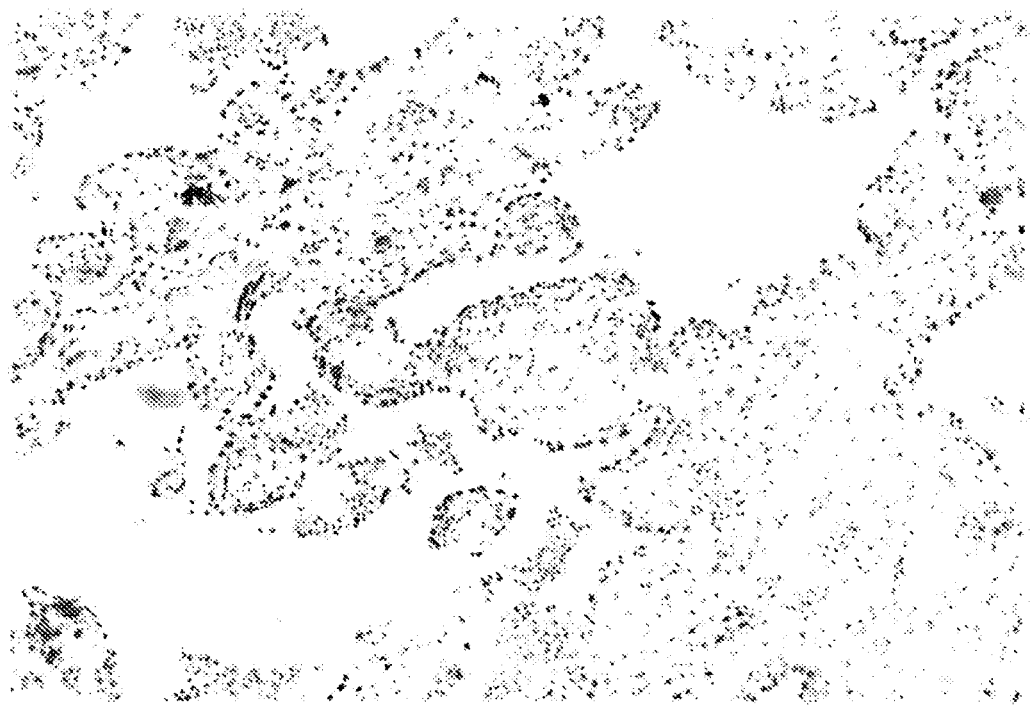
Figure 5B:
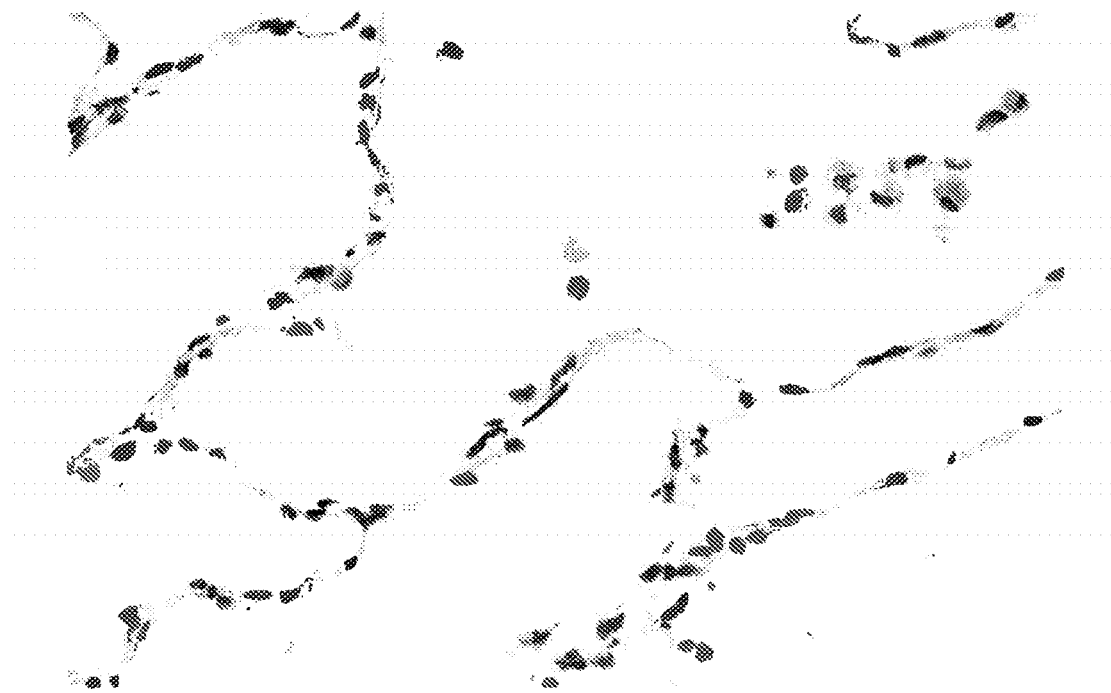
Figure 5C:
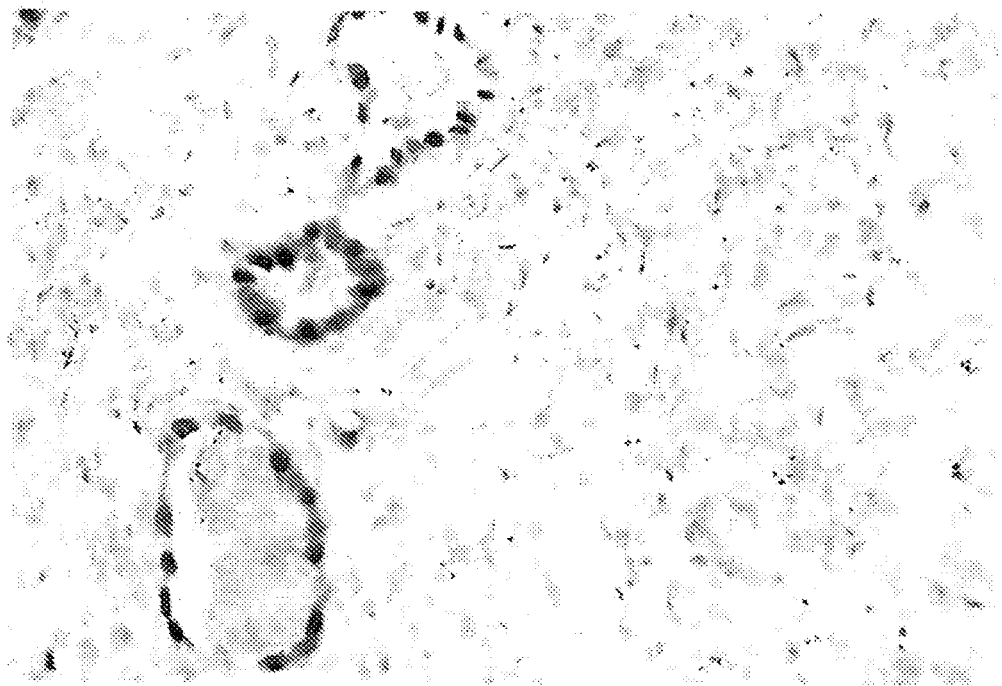
Figure 5D:
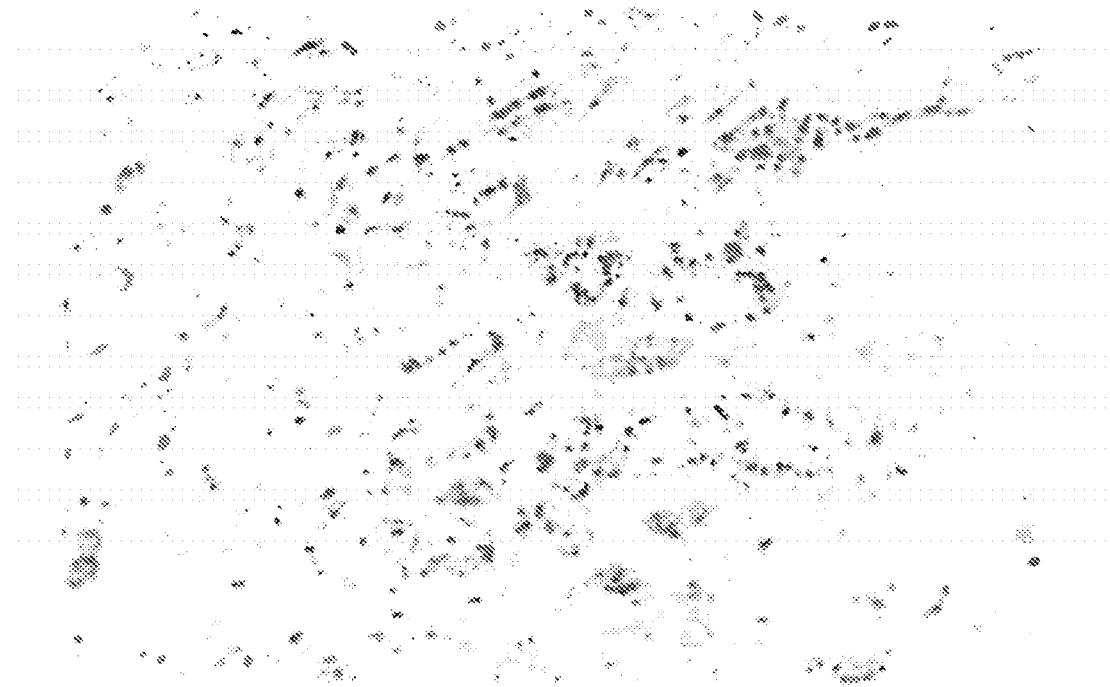
Figure 5E:
Figure 5F:
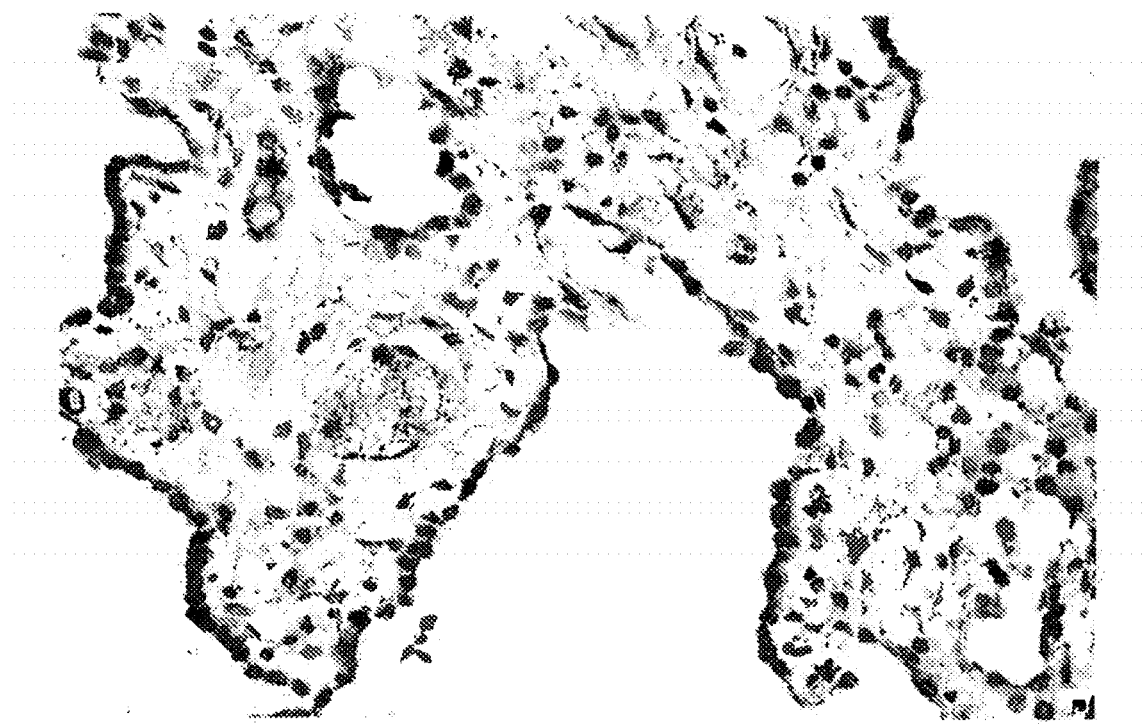
Figure 5G:
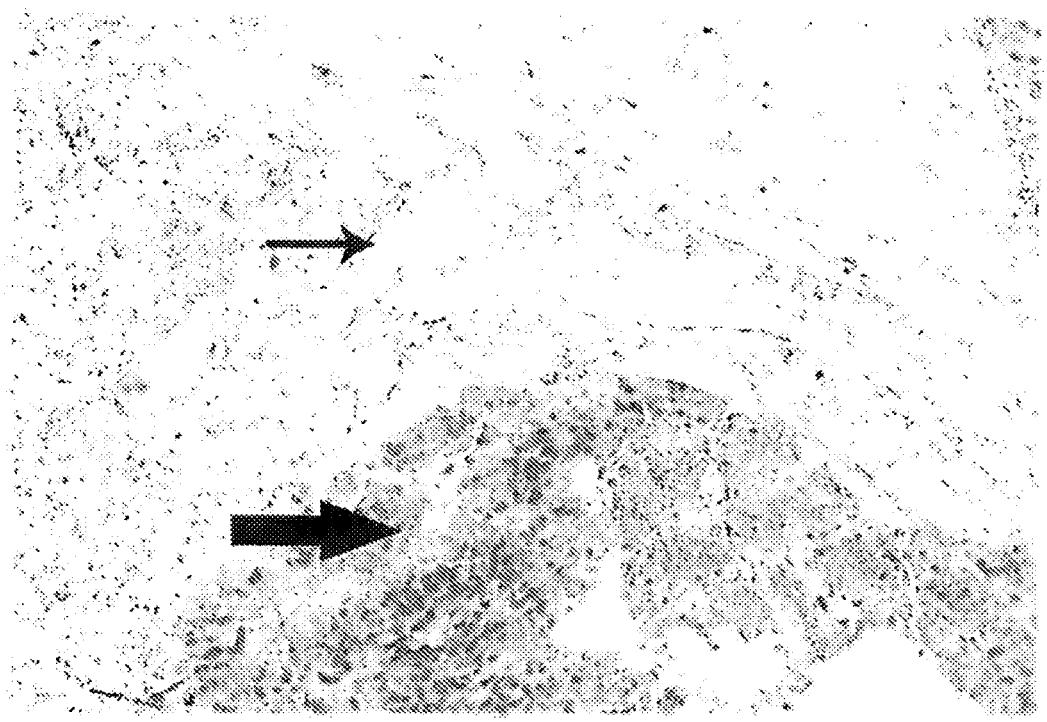
Figure 5H:
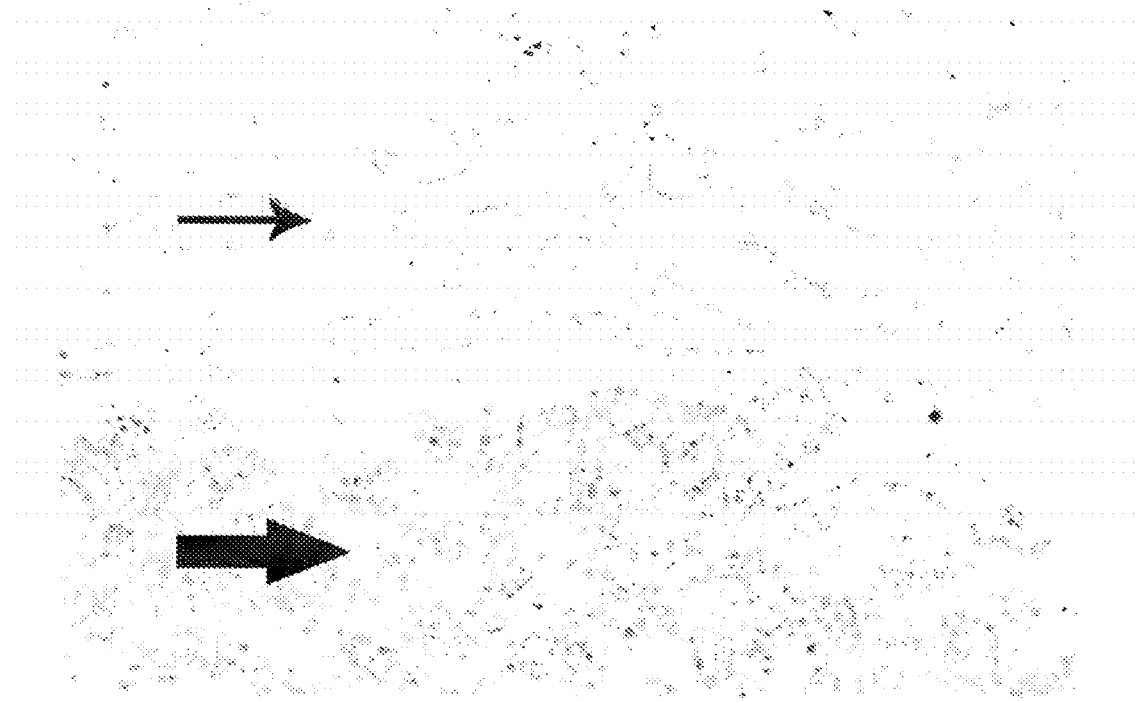

FIGS. 5A-5H. Expression of Herpesvirus saimiri proteins in IPF patient samples. FIG. 5A provides a lung tissue specimen of regenerating epithelial cells from an IPF patient stained with a polyclonal antibody against Herpesvirus saimiri cyclin D using a fast red signal and hematoxylin counterstain at 100× magnification. FIG. 5B shows cyclin D expression in a normal area of lung tissue sample from an IPF patient at 400× magnification. FIG. 5C shows cyclin D expression in an area of lung tissue undergoing active fibrosis at 400× magnification. FIG. 5D provides a lung tissue specimen from an IPF patient stained with a polyclonal antibody against Herpesvirus saimiri dihydrofolate reductase ("DHFR") using a fast red signal and hematoxylin counterstain at 100× magnification. FIG. 5E shows unremarkable lung tissue adjacent to an area of IPF. FIG. 5F provides a lung tissue specimen from an IPF patient stained with a polyclonal antibody against Herpesvirus saimiri thymidylate synthase ("TS") using a DAB signal and hematoxylin counterstain at 400× magnification. FIG. 5G provides a lung tissue specimen from a lung cancer patient stained with a polyclonal antibody against human DHFR using a fast red signal and hematoxylin counterstain at 400× magnification. FIG. 5H provides a lung tissue specimen from a lung cancer patient stained with a polyclonal antibody against human cyclin D using a fast red signal and hematoxylin counterstain at 400× magnification.

Figure 6A:
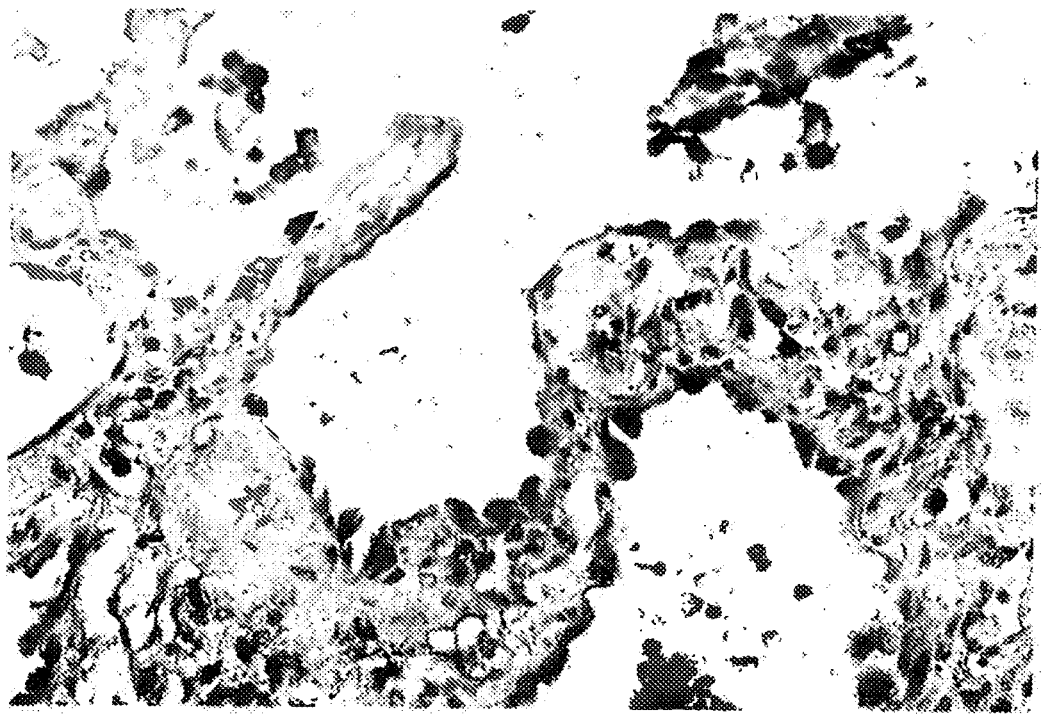
Figure 6B:
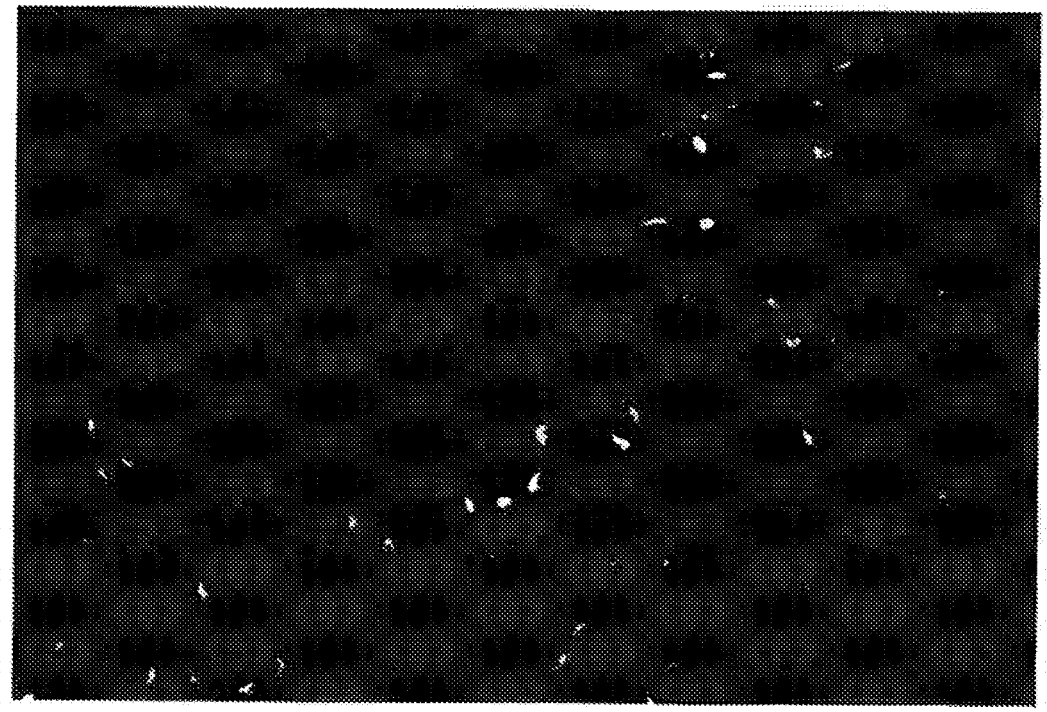
Figure 6C:
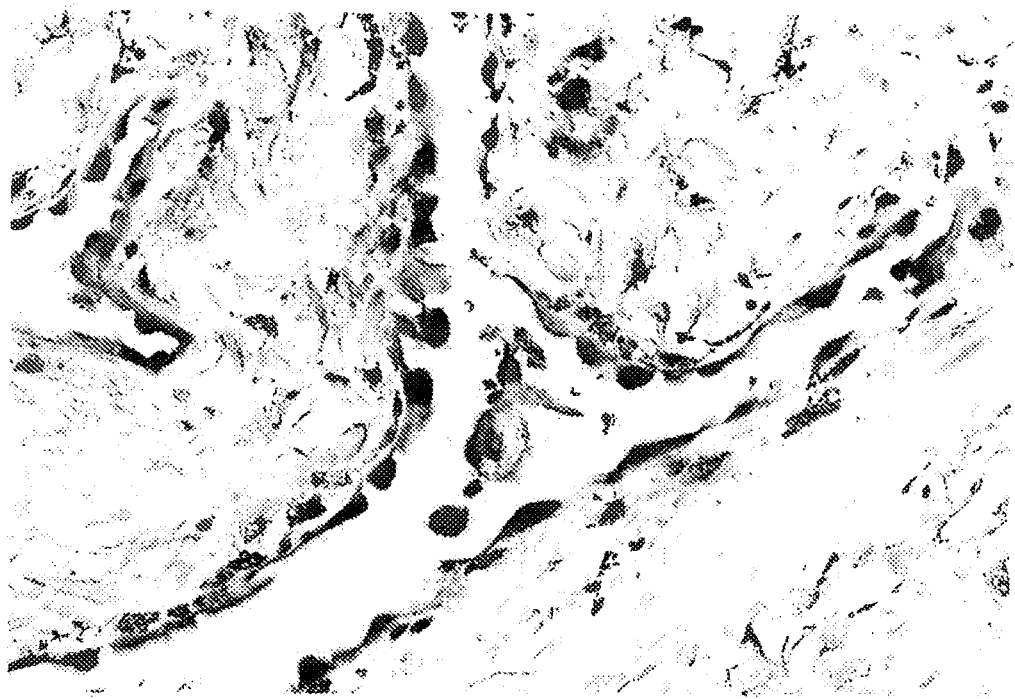
Figure 6D:
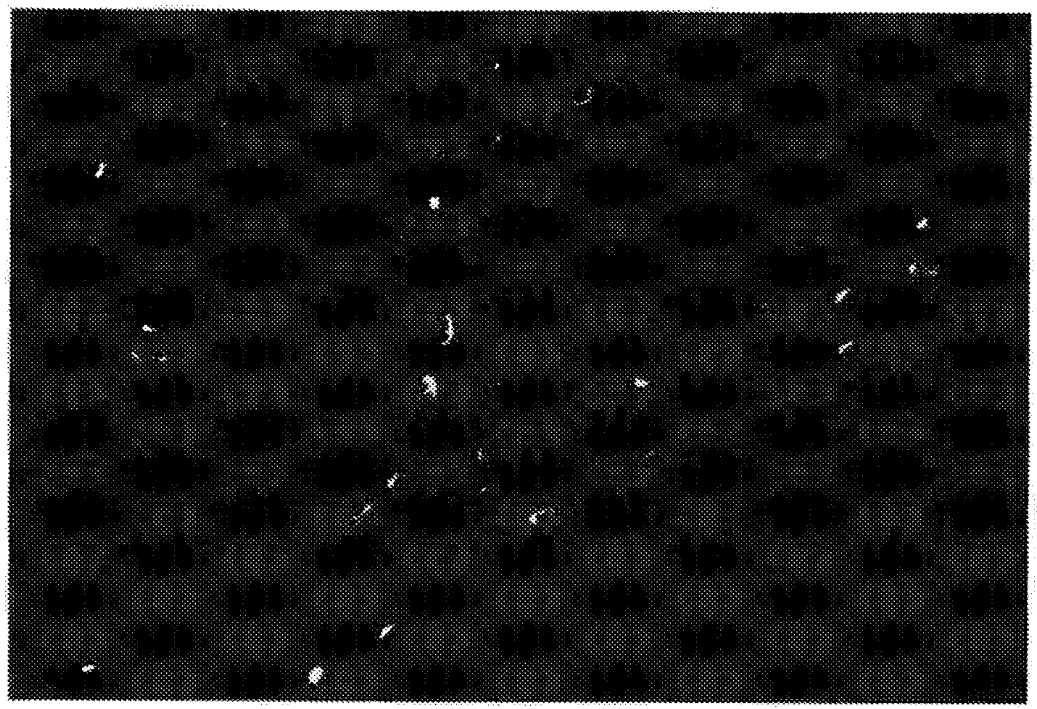
Figure 6E:
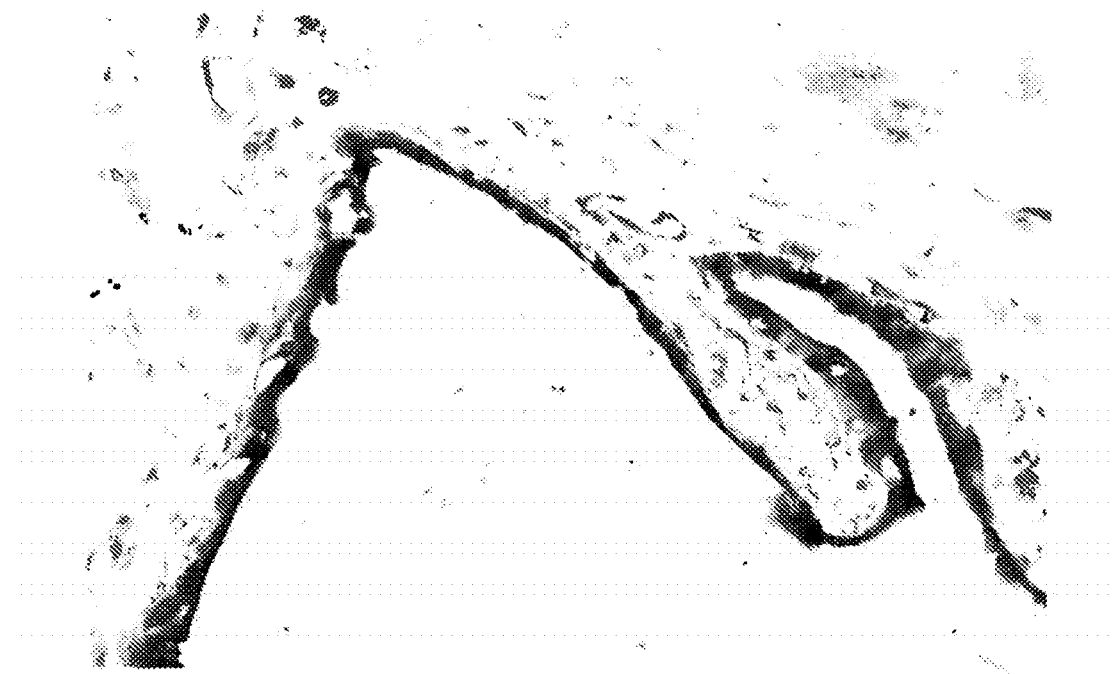
Figure 6F:
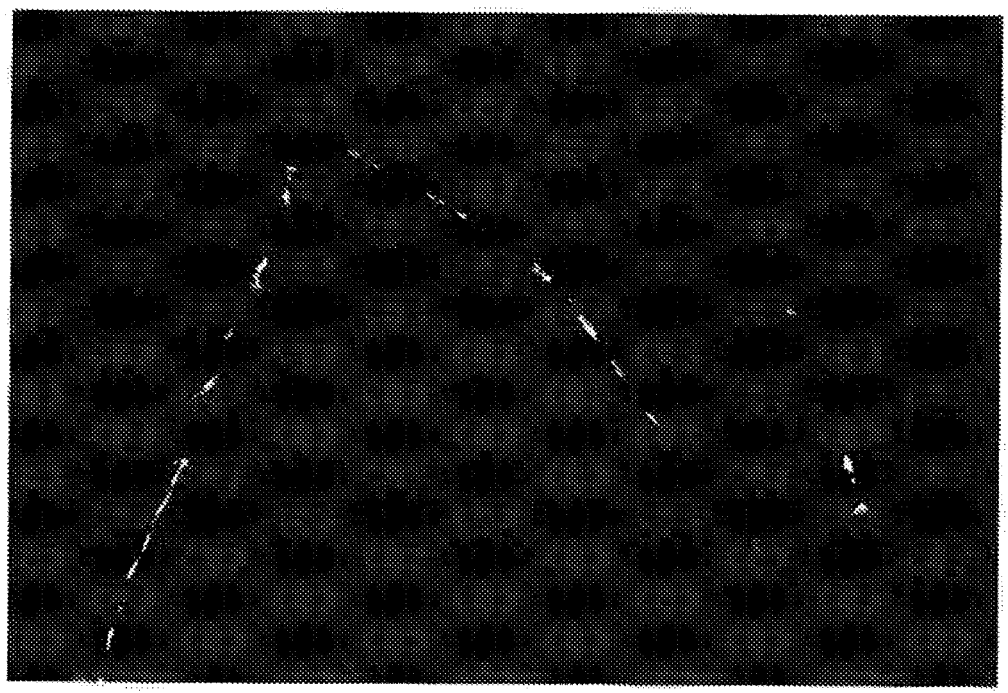
Figure 6G:
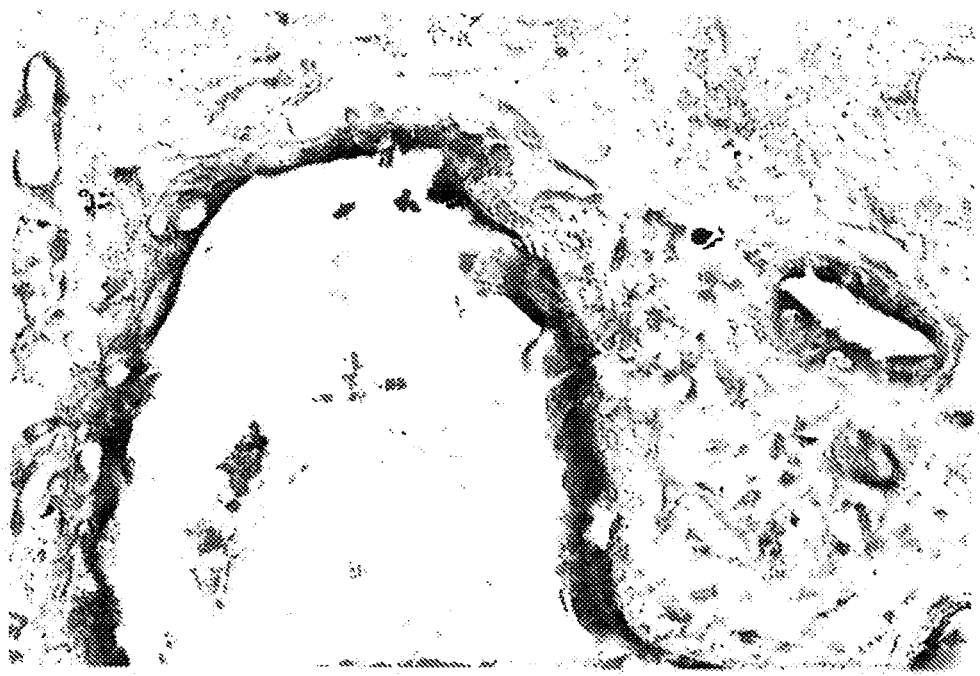
Figure 6H:
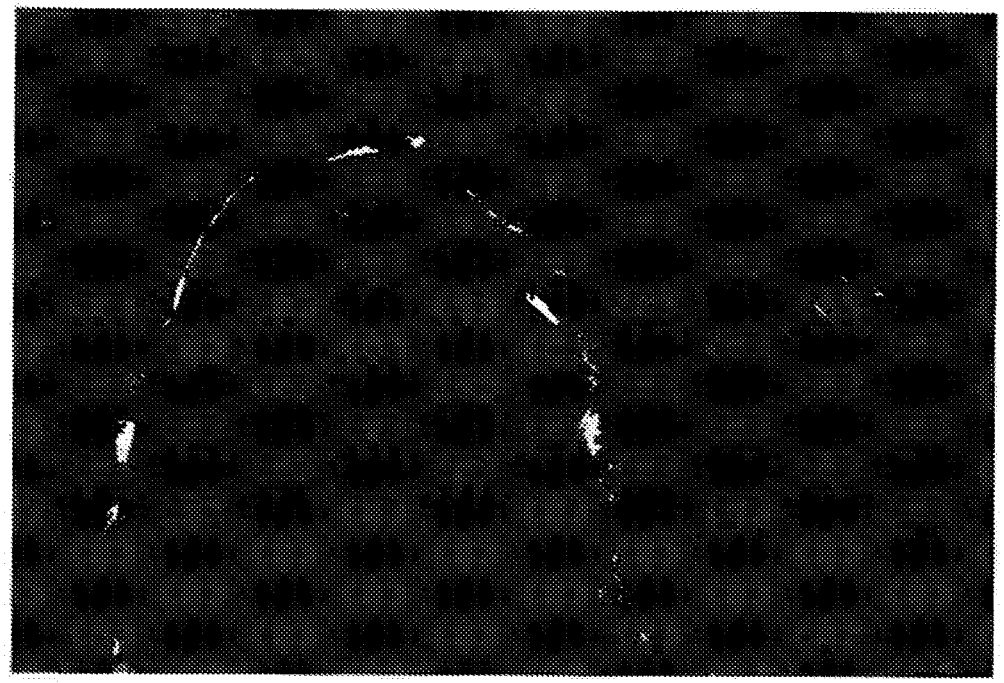

FIGS. 6A-6H. Co-localized expression of Herpesvirus saimiri DNA and proteins. FIG. 6A provides a tissue specimen from an IPF patient that shows co-localization of nucleic acid signal from Herpesvirus saimiri DNA targets stained with NTB/BCIP and an anti-TS antibody to Herpesvirus saimiri TS stained with DAB. FIG. 6B provides a Nuance conversion of FIG. 6A showing signal from Herpesvirus saimiri DNA in blue and signal from the anti-TS antibody in red, where areas of co-localized expression are in yellow. FIG. 6C provides a tissue specimen from an IPF patent that shows co-localization of nucleic acid signal from Herpesvirus saimiri DNA targets stained with NTB/BCIP and an anti-IL-17 antibody to Herpesvirus saimiri IL-17 stained with DAB. FIG. 6D provides a Nuance conversion of FIG. 6C showing signal from Herpesvirus saimiri DNA in blue and signal from the anti-IL-17 antibody in red, where areas of co-localization are in yellow. FIG. 6E provides a tissue specimen from an IPF patient that shows co-localization of nucleic acid signal from Herpesvirus saimiri STP DNA stained with NTB/BCIP and an anti-cyclin D antibody to Herpesvirus saimiri cyclin D stained with fast red signal. FIG. 6F provides a Nuance conversion of FIG. 6E showing signal from Herpesvirus saimiri DNA in blue, signal from the anti-cyclin D antibody in red and where areas of co-localization are in yellow. FIG. 6G provides a tissue specimen from an IPF patient that shows co-localization of nucleic acid signal from Herpesvirus saimiri TER DNA stained with NTb/BCIP and an anti-cyclin D antibody to Herpesvirus saimiri cyclin D stained with fast red. FIG. 6H provides a Nuance conversion of FIG. 6G showing signal from the Herpesvirus saimiri DNA in blue, signal from the anti-cyclin D antibody in red and where areas of co-localization are yellow.

Figure 7A:
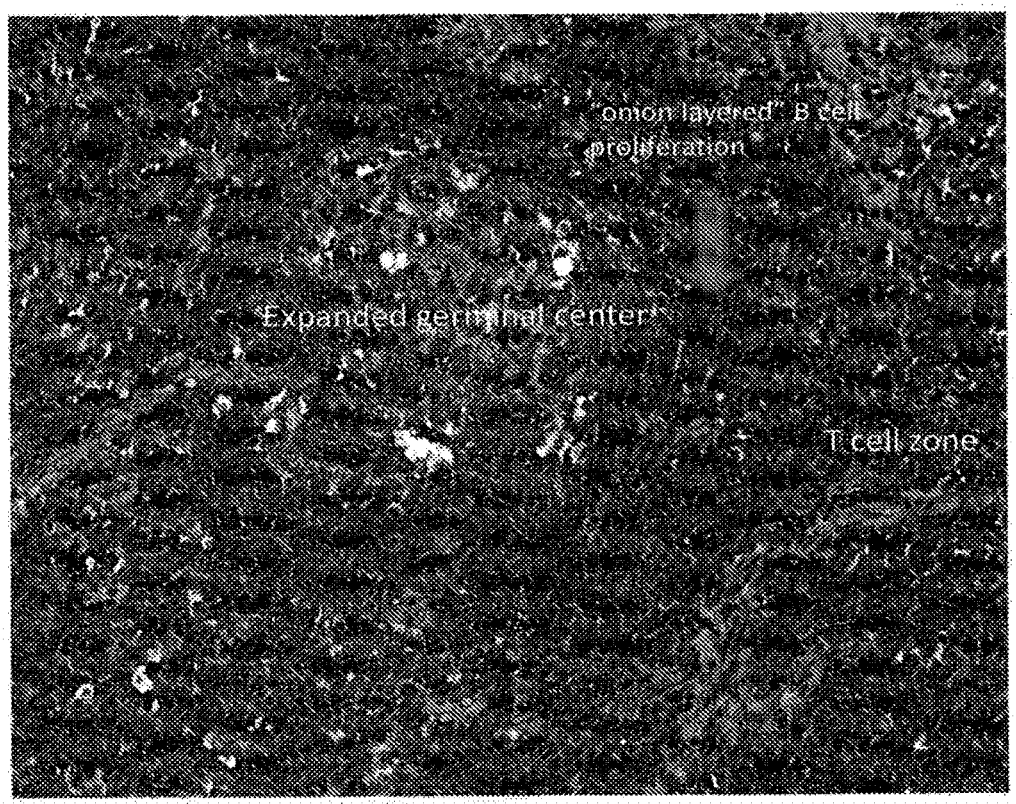
Figure 7B:
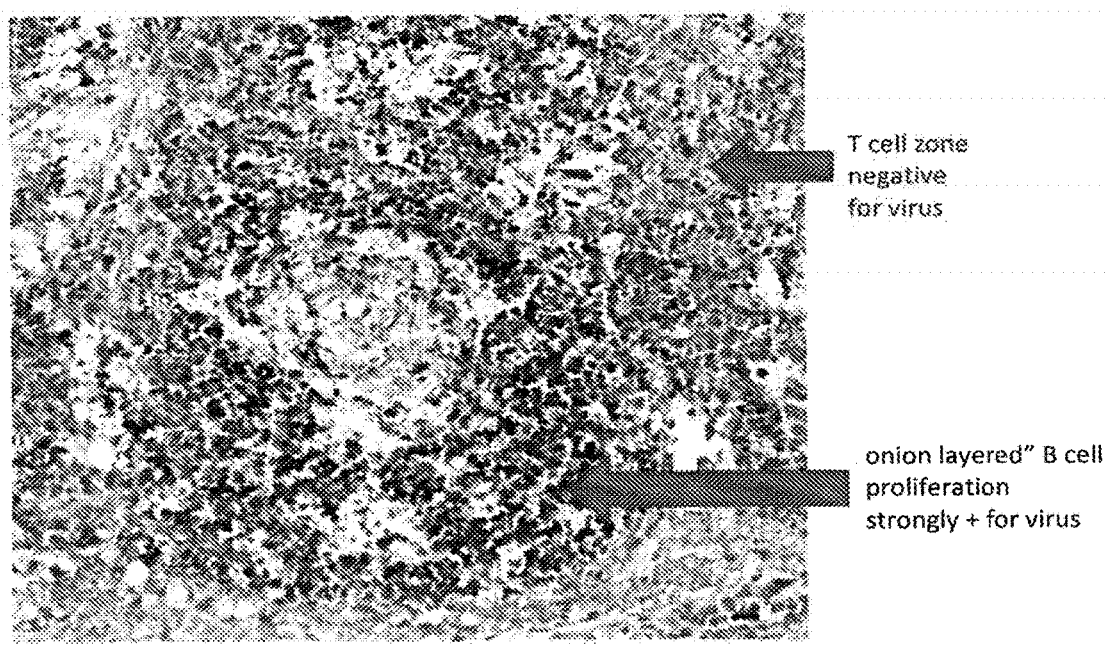
Figure 7C:
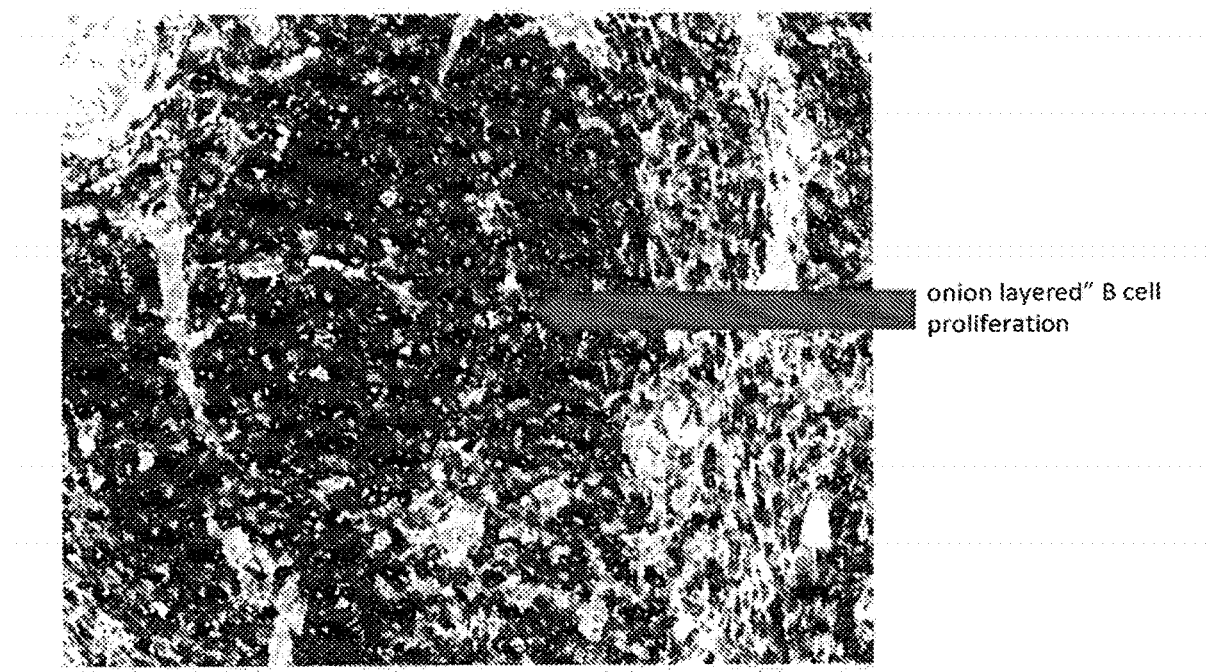
Figure 7D:
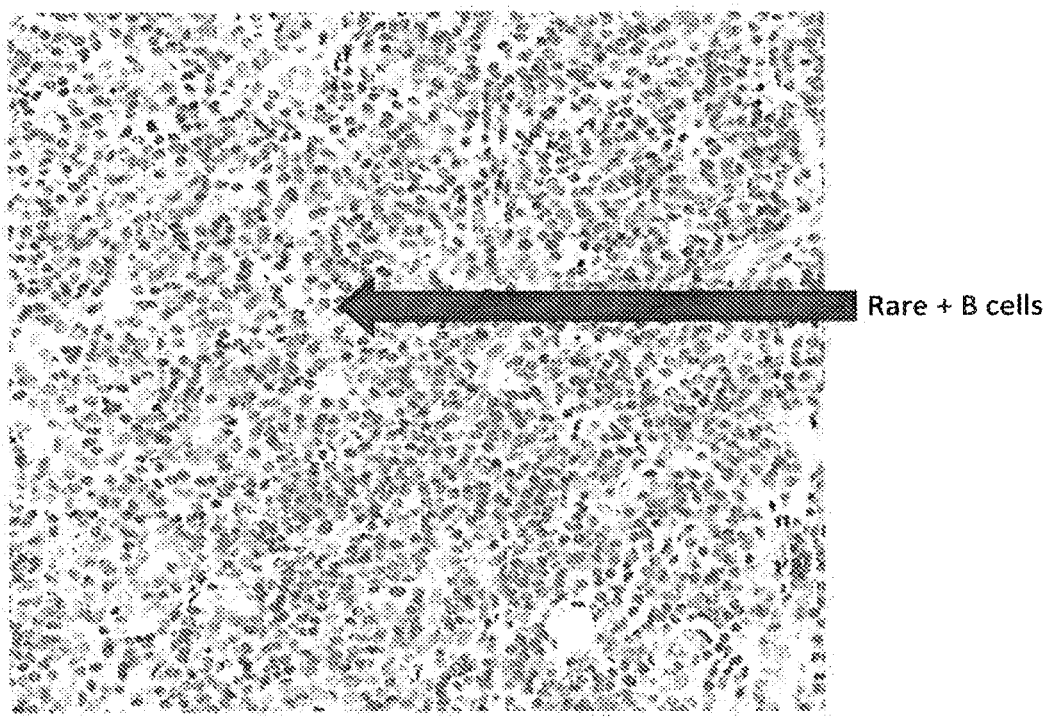
Figure 7E:
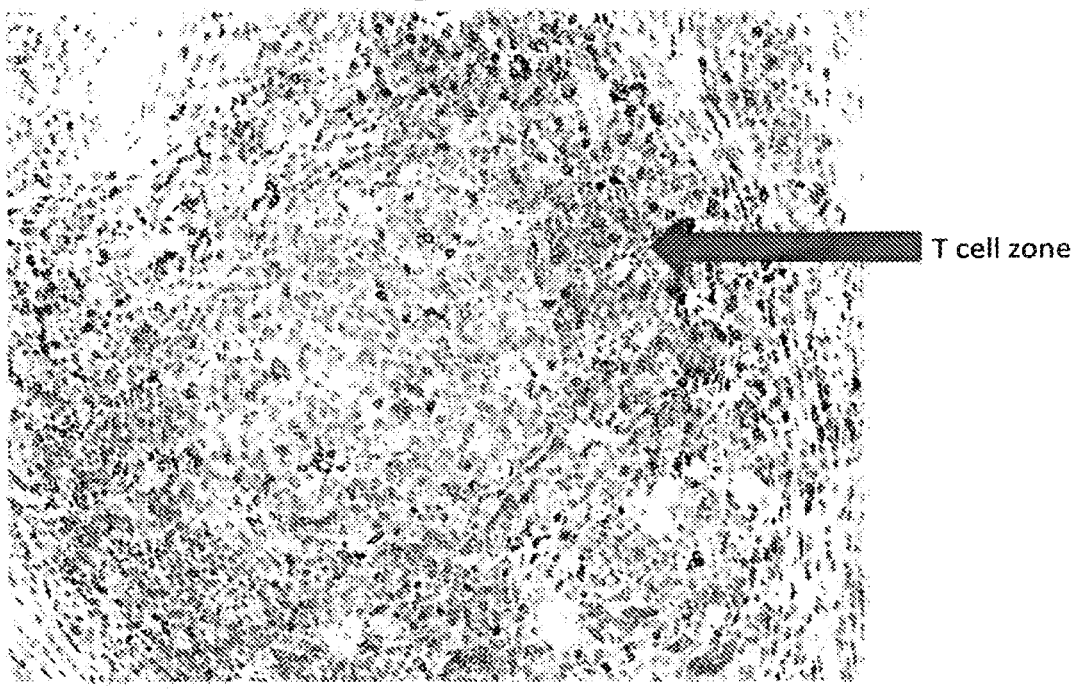
Figure 7F:
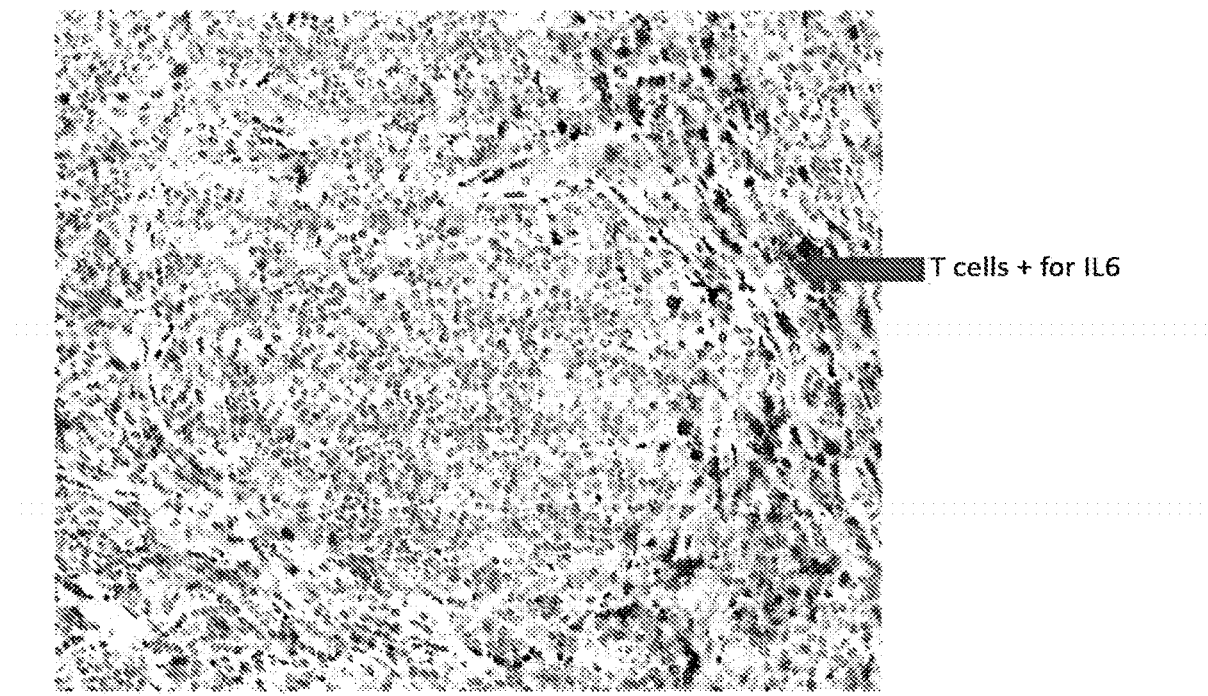
Figure 7G:
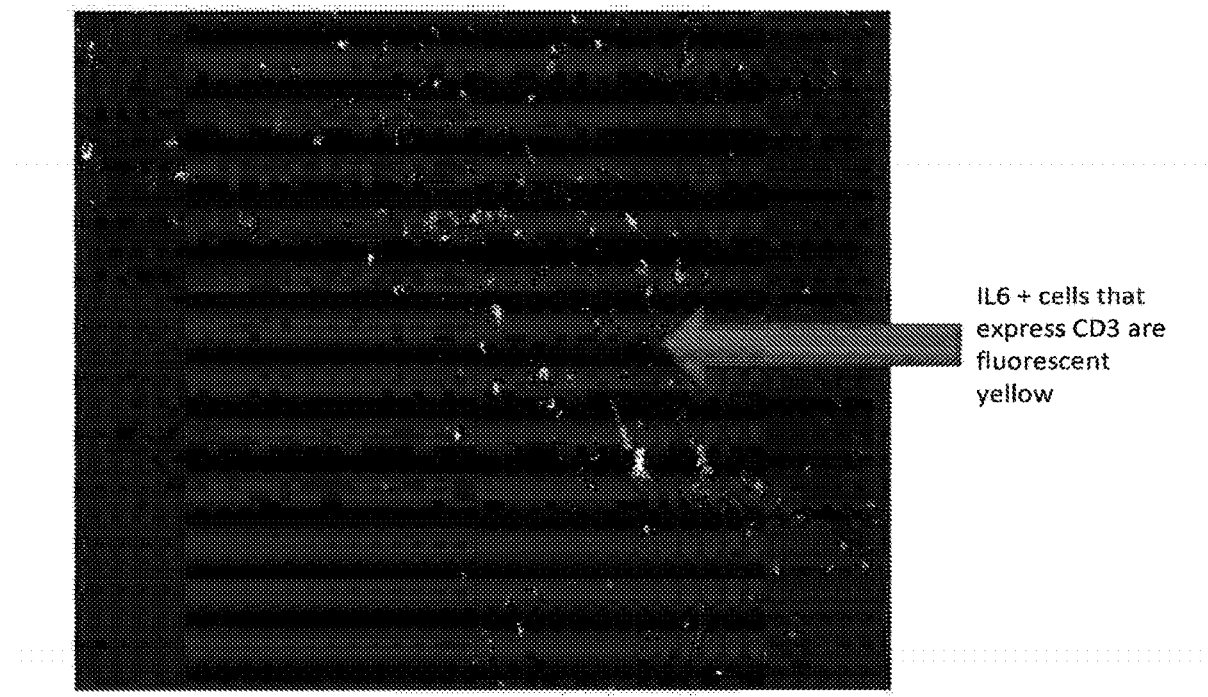
Figure 7H:
Figure 7I:

FIGS. 7A-7I. Herpesvirus saimiri positive B-cells in idiopathic Castleman's disease. FIG. 7A provides a tissue specimen from a mediastinal lymph node of a patient with Castleman's disease stained with hematoxylin and eosin and a central expanded germinal center surrounded by typical "onion-skin" layering of hyperplastic B-cells. The interfollicular zone is noted as the "T cell zone". FIG. 7B provides the specimen of FIG. 7A after in-situ hybridization for HVS DNA using TER probes with NTB/BCIP (blue) as the chromogen and with a pink counterstain. Viral DNA is localized to the "onion-skin" layered areas containing hyperplastic B-cells. The T-cell zone is negative for the viral DNA. FIG. 7C provides the tissue specimen of FIG. 7A after immunohistochemistry for CD20 (B-cells) with DAB (brown) as the chromogen and with a blue counterstain and shows that the expanded germinal center and surrounding hyperplastic mantle zone consist mostly of B-cells. FIG. 7D provides the tissue specimen of FIG. 7A after immunohistochemistry for viral IL-17 with DAB (brown) as the chromogen and with a blue counterstain and shows that few virus-infected B-cells in the expanded germinal center express IL-17, which is indicative of a latent infection. FIG. 7E shows the serial section from the mediastinal lymph node of FIG. 7A after immunohistochemistry for CD3 (T-cells) with DAB (brown) as the chromogen and with a blue counterstain and shows that T-cells localize primarily to the interfollicular zone. FIG. 7F provides the serial section of FIG. 7E probed for the presence of IL-6 with DAB (brown) as the chromogen and with a blue counterstain and shows that the distribution of CD3+ cells matches the distribution of cells expressing IL-6, indicating that T-cells are producing IL-6. FIG. 7G provides co-expression analyses for IL-6 and CD-3, where fluorescent yellow indicates the cells expressing both proteins. Most cells expressing IL-6 are T-cells, whereas the B-cell zone to the left of the IL-6+/CD3+ cells are negative for both markers. FIG. 7H provides the specimen of FIG. 7A after in-situ hybridization for HVS DNA using STP probes, NBT/BCIP (blue) as the chromogen and with a pink counterstain. Viral DNA localizes to the "onion-skin" layered areas which contain the hyperplastic B-cells, while the interfollicular zone which consists of T-cells is negative for viral DNA. FIG. 7I provides the specimen of FIG. 7A after in-situ hybridization for HVS RNA using herpesvirus saimiri U-rich noncoding RNA probes, NBT/BCIP (blue) as the chromogen and with a pink counterstain showing many lymphocytes positive for HVS RNA in the region of an expanded mantle zone.

Figure 8A:
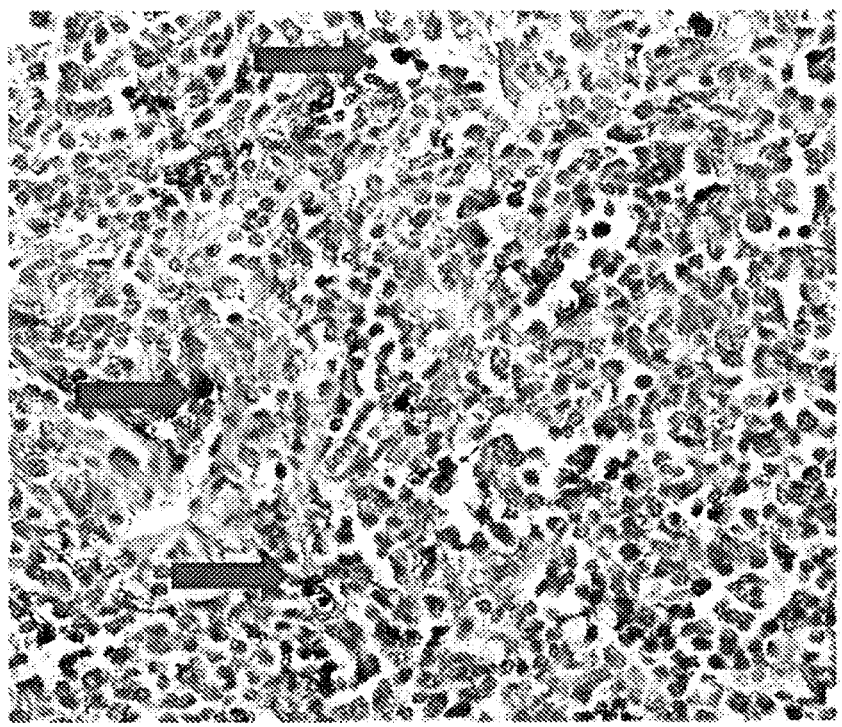
Figure 8B:
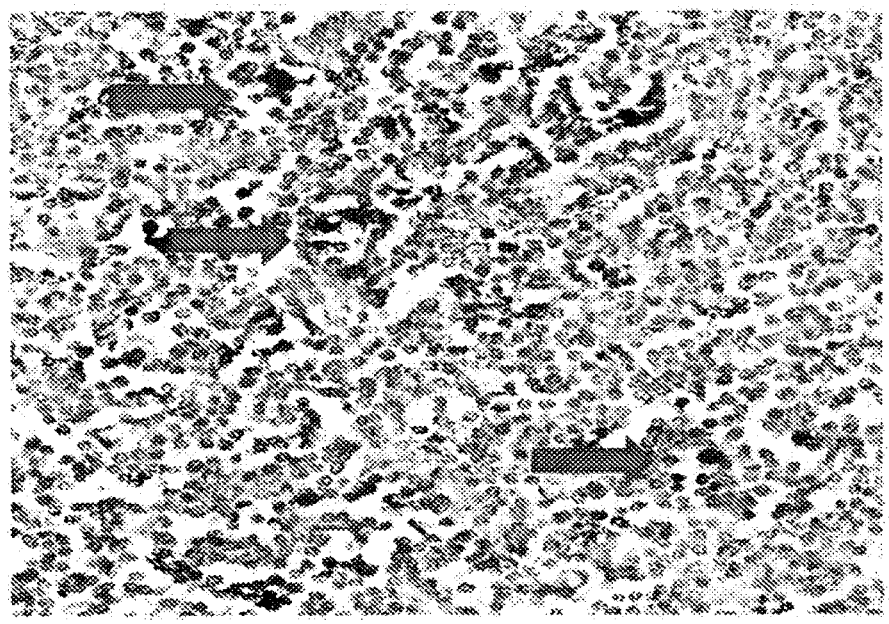
Figure 8C:
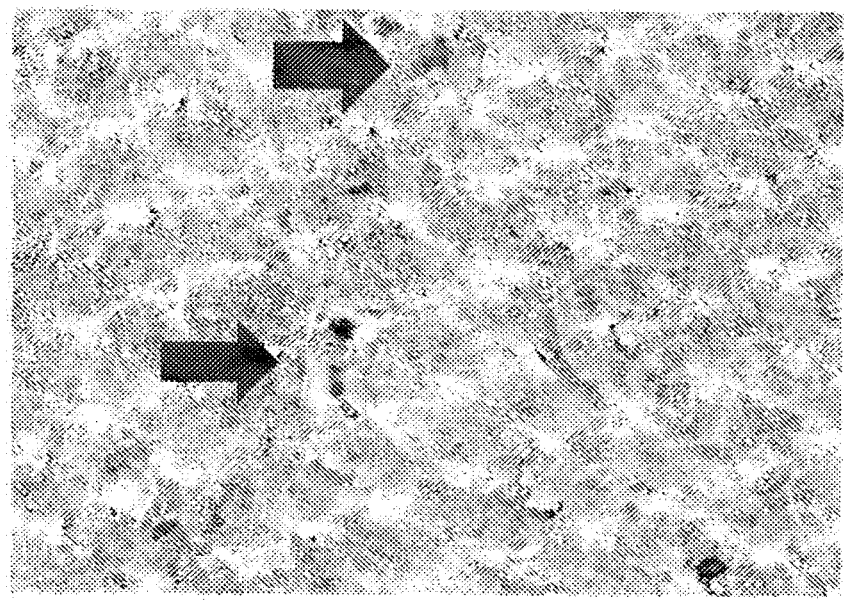
Figure 8D:
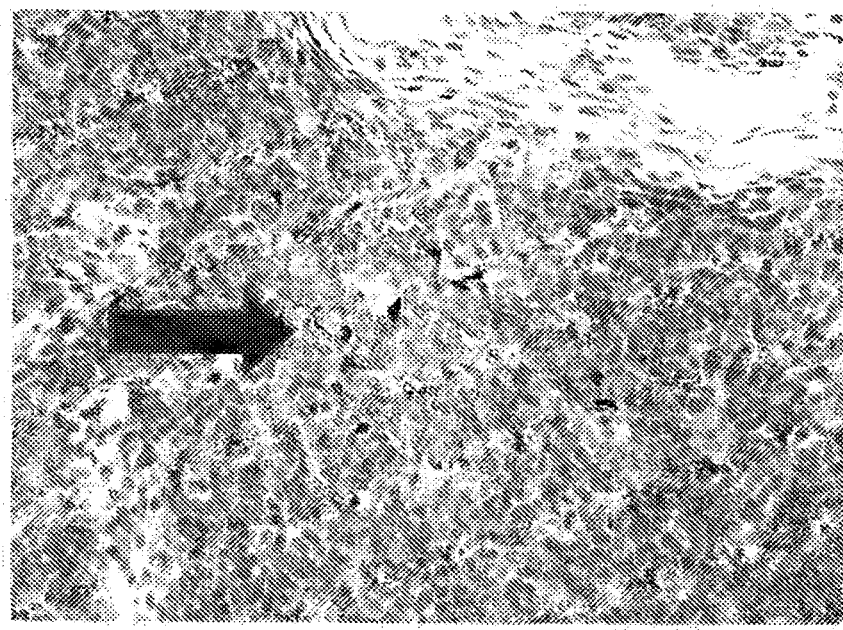

FIGS. 8A-8D. Herpesvirus saimiri positive cells in a thymoma. FIG. 8A provides a tissue specimen from a thymoma after in-situ hybridization with HVS STP probes using NBT/BCIP (blue/black) as the chromogen and with a pink counterstain. A number of HVS+ cells are identified by the arrows. FIG. 8B provides a tissue specimen from a different thymoma than in FIG. 8A after in-situ hybridization with HVS STP probes using NBT/BCIP (blue/black) as the chromogen and with a pink counterstain. A number of HVS+ cells in this second specimen are identified by the arrows. FIG. 8C provides the tissue sample of FIG. 8B after immunohistochemistry for viral IL-17 using DAB (brown) and CD20 using Fast Red signal (red) at high magnification. The specimen shows relatively few IL-17 producing cells and scattered CD20+ cells. FIG. 8D provides the tissue sample of FIG. 8B after immunohistochemistry for viral cyclin D1 with DAB (brown) as the chromogen and with a blue counterstain. The specimen shows relatively few cyclin D1 producing cells.

Figure 9A:
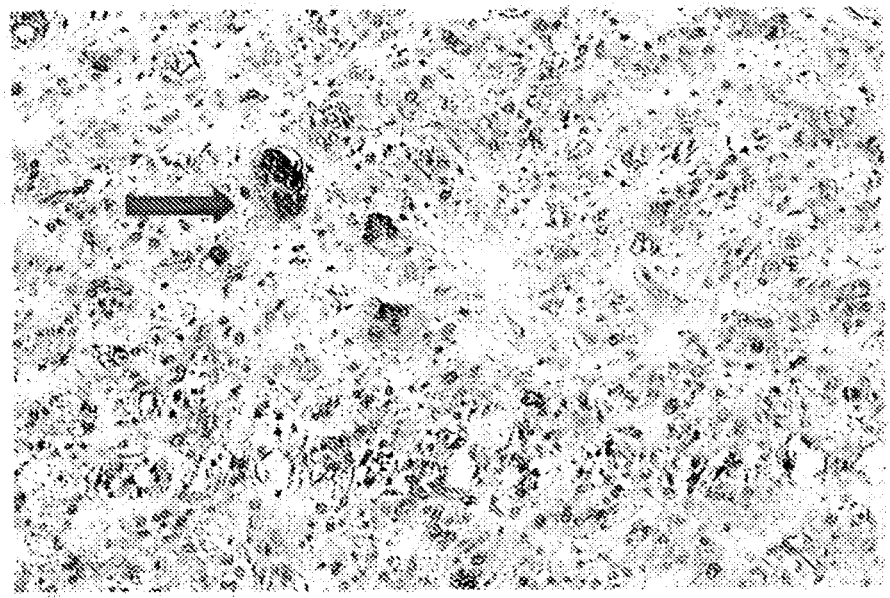
Figure 9B:
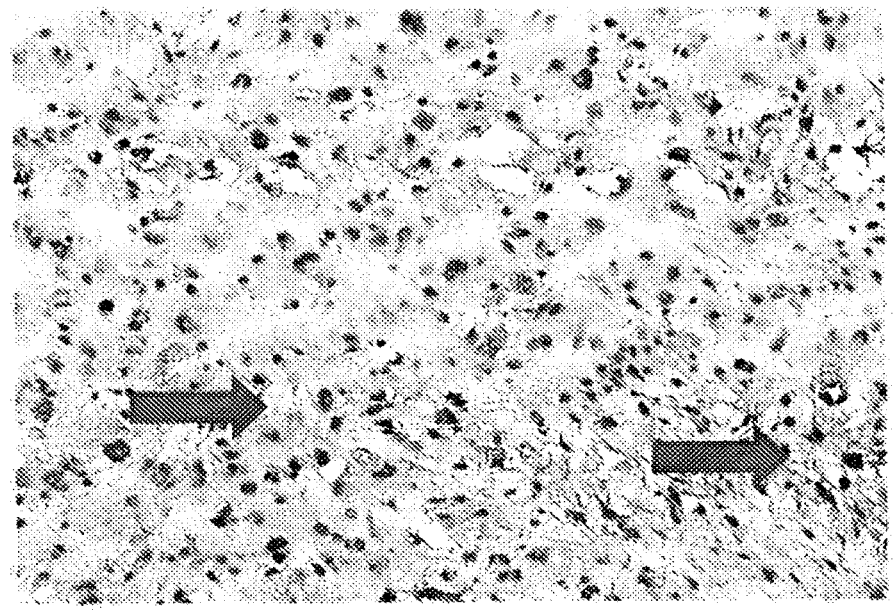

FIGS. 9A-9B. Herpesvirus saimiri positive cells in sarcomas. FIG. 9A provides a tissue specimen from a patient suffering from a retroperitoneal liposarcoma after in-situ hybridization for HVS using STP and TER probes using NBT/BCIP (blue/black) as the chromogen and with a pink counterstain. A number of HVS+ cancer cells show signal localization to the nucleus. FIG. 9B provides a tissue specimen from a different patient suffering from a retroperitoneal liposarcoma after in-situ hybridization for HVS using STP and TER probes using NBT/BCIP (blue/black) as the chromogen and with a pink counterstain. A number of HVS+ cells are identified by the arrows.

Figure 10A:
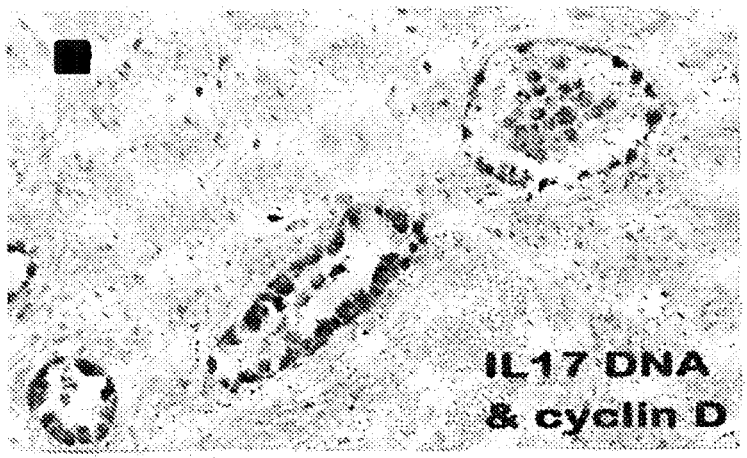
Figure 10B:
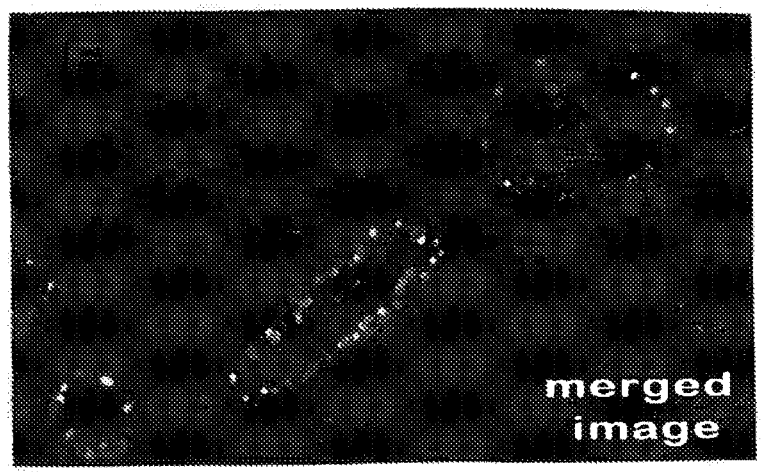
Figure 10C:
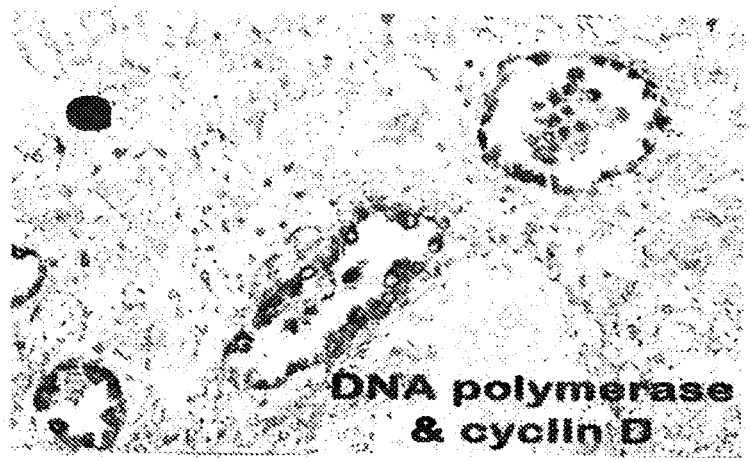
Figure 10D:
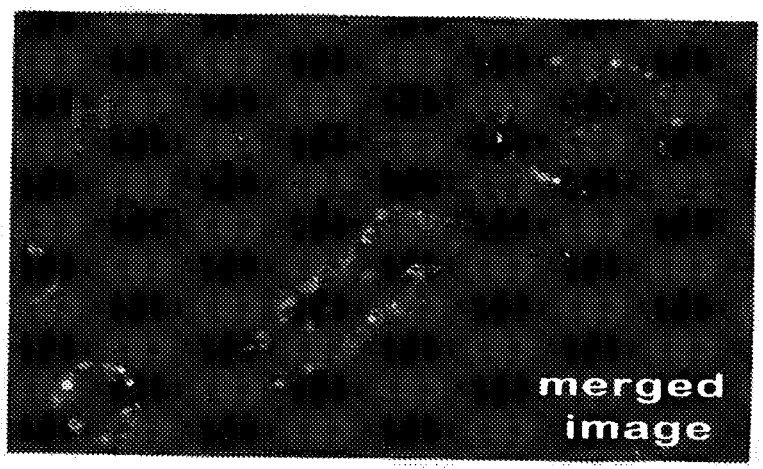

FIGS. 10A-10D. Detection of Herpesvirus saimiri DNA with biotinylated probes. FIG. 10A provides a tissue specimen from an IPF patient analyzed for viral IL-17 using the biotinylated probe described in Example 9 and immunohistochemistry for cyclin D1 with DAB (brown) as the chromogen and with a blue counterstain at 400× magnification. FIG. 10B provides a Nuance conversion of FIG. 10A where the signal for the DNA is blue and signal from the anti-cyclin D antibody in green, where areas of co-localized expression are in yellow. FIG. 10C provides a serial section from the sample of FIG. 2A analyzed for viral DNA polymerase using the biotinylated probe described in Example 9 and immunohistochemistry for cyclin D1 with DAB (brown) as the chromogen and with a blue counterstain at 400× magnification. FIG. 10D provides a Nuance conversion of FIG. 10A where the signal for the DNA is blue and signal from the anti-cyclin D antibody in green, where areas of co-localized expression are in yellow.

5. DETAILED DESCRIPTION

The present invention is based on the inventors' unexpected discovery that Herpesvirus saimiri, a herpesvirus that is endemic and nonpathogenic in squirrel monkeys, and which was previously unknown to be associated with any human disease, causes or is associated with IPF. Specifically, the inventors have discovered that 22 out of 22 lung tissue samples from IPF patients showed the presence of Herpesvirus saimiri DNA, while 25 out of 25 non-IPF samples had a complete absence of the virus DNA. In addition, the present invention is based on the unexpected discovery that Herpesvirus saimiri causes or is associated with tumor or other neoplastic initiation in humans, including lymphoproliferative diseases and cancer, such as Castleman's disease in patients not suffering from AIDS ("idiopathic Castleman's disease"), thymomas, lymphomas, and sarcomas. Specifically, the present inventors have discovered that 13 out of 13 tissue samples from patients suffering from idiopathic Castleman's disease were positive for Herpesvirus saimiri nucleic acids, whereas none of the control patients tested positive for the virus. Furthermore, the present inventors have discovered that Herpesvirus saimiri nucleic acids were present in 6 out of 12 tissue samples from patients with mediastinal or retroperitoneal lymphomas, while no virus was detected in 12 cases of B-cell lymphomas.

Accordingly, the present disclosure relates to methods and compositions for diagnosing, prognosticating and/or monitoring disease progression in a patient known or suspected to be suffering from a viral disease. The present disclosure further relates to methods and compositions for determining the efficacy of therapy in a patient suffering from a viral disease. In still other embodiments, the present disclosure relates to kits for diagnosing, prognosticating and/or monitoring disease progression in a patient known or suspected to be suffering from a viral disease. In some embodiments, the present disclosure relates to methods and compositions for identifying a therapeutic agent for the treatment of a viral disease. In various embodiments, the disclosure relates to methods and compositions for treating a viral disease, and to vaccine compositions for preventing a viral disease by immunizing a subject against infection by a virus.

5.1. Definitions

As used herein, the term "patient" refers to a human subject suffering from or susceptible to a viral disease or who has been exposed to a virus.

The terms "virus" and "viral" as used herein refer to a disease-causing agent that includes Herpesvirus saimiri, including Herpesvirus saimiri strain A ("HVS A"), Herpesvirus saimiri strain B ("HVS B") and Herpesvirus saimiri strain C ("HVS C"). The terms "virus" and "viral" further include any related virus, wherein a "related virus" is defined as a virus that has at least 50%, such as at least about 55%, such as at least about 60%, such as at least about 65%, such as at least about 70%, such as at least about 75%, such as at least about 80%, such as at least about 85%, such as at least about 90%, such as at least about 95%, or such as at least about 99% or more sequence homology of the entire viral genome independently to the entire viral genome of HVS A, or the entire vial genome of HVS B or the entire viral genome of HVS C. For the avoidance of doubt, the genome sequence homology referred to herein is not related to a specific gene or gene segment, but to the homology of the entire genome of a virus to the entire genome of HVS A, or the entire genome of HVS B, or the entire genome of HVS C. The term "Herpesvirus saimiri" when not identified by a specific strain will be understood to include HVS A, HVS B and HVS C.

In the context of the present invention, the term "novel virus" refers to a herpesvirus that is not Herpesvirus saimiri but that is related to it. Specifically, a "novel virus" is a herpes gammavirus having less than 95% homology of the L region with the L region of Herpesvirus saimiri and having 50% or more homology of the L region with the L region of Herpesvirus saimiri. A virus having 95% or more homology in the L region is Herpesvirus saimiri. Furthermore, the gammavirus that is described as having the closest homology with Herpesvirus saimiri is Herpesvirus ateles (Ehlers et al. (2008) J Virol 82; 3509-3516; Lacoste et al. (2010) Inf Genet Evol 10; 1-13) which has about 35% homology with the L region of Herpesvirus saimi (Fleckenstein et al. (1978) J Vir 25; 361-373).

The term "viral disease" as used herein refers to a clinical manifestation in a human that is caused by or associated with infection of a virus that includes Herpesvirus saimiri, including HVS A, HVS B and HVS C. The term "viral disease" further includes a clinical manifestation in a human that is caused by or associated with a related virus. A "viral disease" includes, but is not limited to, idiopathic pulmonary fibrosis (IPF), lymphoproliferative diseases and cancer. In certain embodiments, the lymphoproliferative diseases and cancer include, but are not limited to, idiopathic Castleman's disease, thymomas, lymphomas, and sarcomas. The term "idiopathic Castleman's disease" refers to Castleman's disease that has heretofor had no known cause, and excludes Castleman's disease in patients with HIV infection. Over 90% of Castleman's disease is idiopathic.

As used herein, the terms "unrelated virus" and "unrelated viruses" refer to any virus that has less than 50% homology in the entire viral genome to the entire viral genome of HVS A, or the entire viral genome of HVS B or the entire viral genome of HVS C.

As used herein, the term "virus-specific element" includes any substance derived directly or indirectly from Herpesvirus saimiri or a related virus, including but not limited to, a viral nucleic acid, a viral protein, a peptide derived from a viral protein, a direct or indirect metabolite of a viral protein and/or a patient antibody to a virus-specific element, including but not limited to, envelope proteins of the virus. In some embodiments, a virus-specific element is a virally coded protein involved in viral propagation, viral replication, viral particle assembly or viral latency. In some particular embodiments, the viral protein is a viral analog of a human protein, such as a viral analog of IL-17. In other embodiments, the peptide is derived from a protein that is a viral analog of a human protein (e.g., a peptide from a viral analog of IL-17). In some embodiments, the virus-specific element is an enzyme, such as TS or DHFR. In other embodiments, the viral analog of a human protein is selected from IL-17, TS, DHFR, and cyclin D. In other embodiments, the viral protein is a viral envelope protein or viral capsid protein. In some embodiments, the virus-specific element is the whole virus itself. In still other embodiments, the virus-specific element is a cell that is infected by the virus and thereby expresses a viral-specific element in the cell or on the cell surface.

As used herein, the term "viral metabolite" includes a product of an enzyme of Herpesvirus saimiri or a related virus such as a polymerase, kinase, synthase, protease, reductase, primase, glycosylase, phosphatase, helicase, terminase, transferase, and the like. In some embodiments, the enzyme is unique to the virus. In other embodiments, the enzyme is a viral analog of a host (human) protein.

As used herein, the term "viral property" refers to viral propagation, viral replication, and a virus-specific enzyme, protein or metabolite that are important in the disease-causing process. As described herein, detection of the presence of Herpesvirus saimiri or a related virus and/or association of Herpesvirus saimiri or a related virus with a viral disease means detecting a viral property. In addition, methods of treating or preventing (e.g., by vaccination) a viral disease is by way of manipulation of a viral property.

As used herein, the term "patient antibody" to a virus-specific element includes any antibody produced by a patient that specifically binds to a virus-specific element of Herpesvirus saimiri or a related virus. A patient antibody includes, but is not limited to, a cell-surface bound antibody and an antibody that is not bound to a cell surface. The patient antibody can have any isotype, including IgA, IgD, IgE, IgG and IgM.

As used herein, the terms "antibody" or "antibodies" when referring to an antibody that is not a patient antibody as described above includes, but is not limited to, a human antibody, in which the entire sequence is a human sequence, a humanized antibody, which is an antibody from non-human species whose protein sequences have been modified to increase their similarity to antibody variants produced naturally in humans, and a chimeric antibody, which have certain domains from one organism (e.g., mouse) and other domains from a second organism (e.g., human) to yield, e.g., a partially mouse, partially human antibody. The antibody can include, but is not limited to, an antibody or antibody fragment such as Fab, Fab', F(ab)$_2$, an Fv fragment, a diabody, a tribody, a linear antibody, a single chain antibody molecule (e.g. scFv) or a multi-specific antibody formed by fusions of antibody fragments. In various embodiments, the antibody is polyclonal, monoclonal, multispecific, primatized, or an antibody fragment. In particular embodiments, the antibody is a monoclonal antibody. See, e.g., Riechmann et al. (1988) Nature 332(6162):332-323; Queen et al. (1989) Proc Natl Acad Sci USA. 86 (24):10029-33; Nishimura et al. (1987) Cancer Res. 47:999-1005.

As used herein, the term "clinical sample" refers to a sample from a patient and includes, but is not limited to, whole blood, serum, lung tissue, lavage (e.g., bronchiolar lavage), and formalin fixed paraffin embedded tissue.

The terms "hybrid," "hybridize," "hybridization" and the like refer to the non-covalent interaction between fully complementary or partially complementary nucleic acid sequences. In various embodiments, these terms may be used interchangeably herein, for example, a step of detecting "hybridization" of a nucleic acid probe to a target sequence has the same meaning as detecting the "hybrid" of a nucleic acid probe and a target sequence.

The term "nucleotide analogue" is a variant of a natural nucleotide, such as DNA or RNA nucleotides, by introduction of one or more modifications. In various embodiments, these modifications when incorporated into a nucleic acid will have a functional effect on the properties of the nucleic acid, for example, conferring higher or lower binding affinity for a target sequence, conferring detectability by inclusion of a label and/or conferring the property of degenerate binding to target nucleic acids.

The phrases "treatment of," "treating", and the like include the amelioration or cessation of a condition or a symptom thereof. In one embodiment, treating includes inhibiting, for example, decreasing the overall frequency of episodes of a condition or a symptom thereof.

The phrases "prevention of," "preventing", and the like include the avoidance of the onset of a condition or a symptom thereof.

The term "therapeutic agent" for the treatment of a viral disease, as used herein, refers to an agent identified by the methods described in Section 6.4, the agents described in Section 6.5, known agents for the treatment of viral diseases and combinations thereof.

5.2. Methods for Diagnosing or Prognosticating a Viral Disease, Monitoring Disease Progression and Monitoring the Efficacy of Therapy In certain embodiments, the present disclosure relates to methods for diagnosing a viral disease in a patient, which comprises detecting the presence of a virus-specific element in the patient. In a particular embodiment, the present disclosure relates to methods for diagnosing IPF in a patient, which comprises detecting the presence of a Herpesvirus saimiri-specific element or a related virus-specific element in the patient. In other embodiments, the present disclosure relates to methods for prognosticating a viral disease in a patient by detecting the presence of a virus-specific element in the patient. In a particular embodiment, the present disclosure relates to methods for prognosticating IPF in a patient by detecting the presence of Herpesvirus saimiri-specific element or a related virus-specific element in the patient. In some embodiments, a viral disease is diagnosed or prognosticated in an asymptomatic patient. In other embodiments, a viral disease is diagnosed in a patient suffering from one or more symptoms. In still other embodiments, a viral disease is diagnosed or prognosticated in a patient with one or more potential risk factors for a viral disease.

It will be understood by the skilled artisan that one or more virus-specific elements and/or antibodies to a virus-specific element can be measured in the methods disclosed herein.

In particular embodiments, the viral disease is IPF. In certain embodiments, IPF is diagnosed in a patient who is suffering from interstitial lung disease. In yet other embodiments, IPF is diagnosed in a patient who evidences a usual interstitial pneumonia pattern on high-resolution computed tomography (HRCT). In still other embodiments, IPF is diagnosed in a patient with one or more potential risk factors for IPF, such as cigarette smoking, environmental exposure (e.g., to squirrel monkeys, birds, chemicals used in hair dressing or farming, stone cutting/polishing, and exposure to livestock and to vegetable dust and/or animal dust), chronic viral infection, and abnormal gastroesophageal reflux. In some embodiments, the methods and compositions can be used to screen healthy individuals with one or more risk factors. In yet another embodiment, the methods can be used to screen healthy individuals with no risk factors.

In other embodiments, the viral disease is selected from lymphoproliferative diseases and cancer. In certain embodiments, the lymphoproliferative diseases and cancer include, but are not limited to, idiopathic Castleman's disease, thymomas, lymphomas, and sarcomas. In various embodiments, the viral disease is retroperitoneal or mediastinal lymphocytic proliferation. In some embodiments, the viral disease is retroperitoneal or mediastinal sarcoma. In certain embodiments, the viral disease is gastrointestinal stromal sarcoma. In other embodiments, the viral disease is retroperitoneal liposarcoma.

In various embodiments, the present disclosure also relates to methods of monitoring the progression of a viral disease in a patient, which comprises measuring a first level of a virus-specific element and/or a patient antibody to a virus-specific element in a first clinical sample from the patient, measuring a second level of a virus-specific element and/or a patient antibody to a virus-specific element in a second clinical sample from the patient and comparing the first level of virus-specific element and/or antibody with the second level of virus-specific element and/or antibody, wherein a first level of virus-specific element and/or antibody that is lower than a second level of virus-specific element and/or antibody is indicative of disease progression. In certain embodiments, the viral disease to be monitored is IPF and the virus-specific element is from Herpesvirus saimiri or a related virus and/or the antibody is specific for a Herpesvirus saimiri-specific element or a related virus-specific element. In other embodiments, the viral disease to be monitored is selected from a lymphoproliferative disease and cancer. In certain embodiments, the lymphoproliferative disease and cancer include, but are not limited to, idiopathic Castleman's disease, thymomas, lymphomas, and sarcomas, and the virus-specific element is from Herpesvirus saimiri or a related virus and/or the antibody is specific for a Herpesvirus saimiri-specific element or a related virus-specific element. In various embodiments, the second clinical sample is collected from the patient at least about 1 day, at least about 1 week, at least about 2 weeks, at least about 3 weeks, at least about 1 month, at least about 3 months, at least about 6 months, at least about 9 months, at least about 12 months or more after the first clinical sample is collected.

In still other embodiments, the disclosure relates to methods of monitoring the efficacy of a therapy for the treatment of a viral disease, which comprises measuring a first level of a virus-specific element and/or patient antibody to a virus-specific element in a first clinical sample from an untreated patient, measuring a second level of a virus-specific element and/or patient antibody to a virus-specific element in a second clinical sample from the patient after treatment and comparing the first level of virus-specific element and/or antibody and the second level of virus-specific element and/or antibody, wherein a first level of a virus-specific element and/or antibody that is greater than the second level of the virus-specific element and/or antibody is indicative of the efficacy of the therapy. In certain embodiments, the viral disease is IPF and the virus-specific element is derived from Herpesvirus saimiri or a related virus and/or the antibody is specific for a Herpesvirus saimiri-specific element or a related virus-specific element. In other embodiments, the viral disease is selected from a lymphoproliferative disease and cancer. In certain embodiments, the lymphoproliferative diseases and cancer include, but are not limited to, idiopathic Castleman's disease, thymomas, lymphomas, and sarcomas, and the virus-specific element is derived from Herpesvirus saimiri or a related virus and/or the antibody is specific for a Herpesvirus saimiri-specific element or a related virus-specific element. In various embodiments, the second clinical sample is collected from the patient at least about 1 day, at least about 1 week, at least about 2 weeks, at least about 3 weeks, at least about 1 month, at least about 3 months, at least about 6 months, at least about 9 months, at least about 12 months or more after the therapy is administered to the patient. The skilled artisan will understand that an "untreated patient" may refer to a patient who has not had any treatment for the viral disease or to a patient who was previously treated with a therapy for the viral disease that is different from the therapy being monitored in the methods disclosed herein.

The discovery that the presence of Herpesvirus saimiri is highly correlated with IPF and other diseases such as lymphoproliferative diseases and cancer in patients allows for the development of methods and compositions for diagnosing or prognosticating a viral disease, such as IPF, lymphoproliferative diseases and cancer, in a patient and/or methods for monitoring the progression of a viral disease and/or methods for monitoring the efficacy of therapy in a patient suffering from a viral disease in lieu of elaborate histochemical analyses or high-resolution computed tomography. In certain embodiments, the disease that is diagnosed or prognosticated is IPF. In other embodiments, the disease that is diagnosed or prognosticated is selected from a lymphoproliferative disease (e.g., Castleman's disease), a thymoma, a lymphoma, and a sarcoma. In some embodiments, the virus-specific element detected in a clinical sample is a viral nucleic acid and the detection methods are carried out using one or more nucleic acid probes that specifically bind to a viral nucleic acid. In certain embodiments, the viral nucleic acid is RNA. In the context of the present disclosure, RNA includes both spliced and unspliced RNA molecules transcribed from the genome, such as mRNA and small U-RNAs that do not code for proteins. In other embodiments, the viral nucleic acid is DNA. In some embodiments, the nucleic acid is purified from the clinical sample before detection. In other embodiments, the nucleic acid is not purified from the clinical sample before detection.

In certain embodiments, the detection is carried out by specifically hybridizing a nucleic acid from the clinical sample with a nucleic acid probe. In other embodiments, the detection is carried out by first making a copy of a nucleic acid from the clinical sample and then specifically hybridizing the nucleic acid copy with a nucleic acid probe. In some embodiments, the nucleic acid probe comprises a sequence from viral DNA. In other embodiments, the nucleic acid probe comprises a sequence that is complementary to a nucleic acid sequence from viral DNA. In certain embodiments, the viral DNA is from Herpesvirus saimiri. In still other embodiments, the nucleic acid probe comprises a sequence that is complementary to a nucleic acid sequence from viral RNA. In yet additional embodiments, the nucleic acid probe comprises a sequence that is complementary to a nucleic acid sequence from viral mRNA. In certain embodiments, the viral RNA is from Herpesvirus saimiri or a related virus. As used herein, a nucleic acid from a clinical sample that specifically hybridizes to a nucleic acid probe means that the nucleic acid and the probe have a sufficient degree of complementarity to avoid non-specific binding of the nucleic acid under the conditions of the assay.

In various embodiments, nucleic acid probes that specifically bind to a viral nucleic acid sequence are used for directly detecting target nucleic acids by fluorescent in-situ hybridization (FISH) as described in Example 1. In other embodiments, detection of viral nucleic acids is carried out by isolation of nucleic acids from a clinical sample, binding to a matrix and detection with a labeled probe. Examples of such methods can include dot blot, slot blot, Northern blot, Southern blot and a sandwich assay. In other specific embodiments, labeled nucleic acid probes that specifically bind to viral nucleic acid sequences are used in conjunction with flow cytometry to identify the presence of the virus in cells. See Coquillard et al. (2011) Gynecologic Oncol. 120; 89-93. In still other embodiments, nucleic acids from a clinical sample are labeled and hybridized with probes that specifically bind to viral nucleic acids. In various embodiments, the probes are immobilized on a solid support, e.g., in a microarray, beads or a reverse dot blot. In certain particular embodiments, e.g., when the detection is performed in situ, detection is carried out fluorescently or enzymatically. See, e.g., Langer-Safer et al. (1982) Proc. Natl. Acad. Sci. U.S.A. 79 (14): 4381-85. In other embodiments of the present invention, no labeled nucleic acids are used and detection of viral DNA is carried out by way of a Gardella gel. See Gardella et al. (1984) J. Virol. 50:248-254.

Nucleic acids can be labeled by any method known in the art. In some embodiments, the label is a radioactive label. In other embodiments, the label is a non-radioactive label. In certain embodiments, the non-radioactive label is selected from a fluorescent label, a chemiluminscent label, a hapten label, a chromogenic label, and an energy transfer pair. Such fluorescent labels include, but are not limited to, xanthene dyes, anthracene dyes, cyanine dyes, porphyrin dyes, rhodamine dyes, coumarin dyes and dyes disclosed in any of U.S.

Pat. Nos. 8,247,179, 7,569,695, 8,153,802, 8,389,729, and U.S. Patent Publication No. 2012/0040430, each of which is incorporated herein by reference in its entirety. In certain embodiments, the fluorescent label is covalently attached to one or more nucleotides on the sugar, base, phosphate or a combination thereof. In other embodiments, the fluorescent label is not covalently attached to the nucleic acid, but binds to double-stranded nucleic acids, for example, an intercalator. In various embodiments, the non-radioactive label is a chemiluminescent label. In other embodiments, the label is a chromogenic label, e.g., a compound such as the 1,2-dioxetane reagents disclosed in U.S. Pat. No. 8,247,179 that comprise two groups attached to different sites of a cyclic ring where after catalysis by an appropriate enzyme, the reagent undergoes an intramolecular reaction, thereby leading to signal generation. In still other embodiments, the label is an energy transfer pair. The skilled artisan will understand that energy transfer can be between labeled primers, a labeled primer and one or more labeled nucleotides, labeled nucleotides, a labeled primer and a labeled nucleotide or nucleotides, a labeled probe and a labeled nucleotide or nucleotides, and the like. See U.S. Pat. No. 8,247,179 for discussion of energy transfer protocols. In particular embodiments, the first energy transfer element and the second energy transfer element are independently selected from fluorescein, fluorescein isothiocyanate (FITC), 6-carboxyfluorescein (6-FAM), naphthofluorescein, rhodamine, rhodamine 6G, rhodamine X, rhodol, sulforhodamine 101, tetramethylrhodamine (TAMRA), tetramethylrhodamineisothiocyanate (TRITC), 4,7-dichlororhodamine, eosin, eosinisothiocyanate (EITC), dansyl, hydroxycoumarin, methoxycoumarin or p-(Dimethyl aminophenylazo) benzoic acid (DABCYL), cyanine dyes, or derivatives of any of the foregoing. In various embodiments, the label is a hapten, a highly immunogenic compound that is detected by binding of labeled anti-hapten antibodies. Such haptens include, but are not limited to, digoxigenin, DNP (dinitrophenol), biotin, and fluorescein (which is also a fluorescent dye). In various embodiments, the nucleic acid label is a compound that can be detected by binding to a labeled binding partner other than an antibody, such as biotin, avidin or streptavidin. In various embodiments, the nucleic acid is bound to an enzymatic label—an enzyme whose presence can be detected by the addition of a substrate that the enzyme converts to a detectable product. In certain embodiments, a label is attached directly to the nucleic acid. In other embodiments, the label is attached via a linker arm. Various linker arms that are useful for attaching a label to a nucleic acid can be found, for example, in U.S. Pat. No. 8,247,179.

In certain embodiments, the methods described herein further include a step of amplifying the signal for increasing the sensitivity of detection. In various embodiments, methods for signal amplification include, but are not limited to, detection with bDNA probes, detection with antibodies against DNA/RNA hybrids, use of gold nanoparticles (Verigene), use of the Invader system and rolling circle amplification (RCA). See, e.g., Terry et al. (2001) J. Med. Virol. 65; 155-162; Storhoff et al. (2004) Nature Biotechnology 22; 883-887; Hall et al. (2000) Proc. Nat. Acad. Sci. USA 97; 8272-8277; Lizardi et al., (1998) Nat. Genet. 19; 225-232.

In other embodiments, the methods described herein further include a step of amplifying nucleic acids before detection. In certain embodiments, nucleic acids are amplified by PCR or RT-PCR. In certain embodiments, the amplifying step comprises global amplification of any and all sequences as is typically done when using whole-genome amplification (WGA) or expression arrays. A common method used for amplification of RNA from expression arrays is the Eberwine method (Eberwine et al. (1992) Proc. Nat. Acad. Sci. (USA) 89:3010-14) and exemplary methods for WGA are degenerate oligonucletotide primer PCR (DOP-PCR) as described in Telenius et al. (1992) Genomics 13:718-725, and multiple displacement amplification (MDA) as described in Dean et al. (2002) Proc. Nat'l Acad. Sci. (USA) 99:5261-5266. In other embodiments, amplification may utilize target-specific primers or a reverse transcription step to allow specific amplification of viral nucleic acids. Analysis of amplified products can be performed by end-point PCR using, e.g., a sandwich assay, dot blot, Southern blot, Northern blot, microarray or Mass Spectrometry (including electrospray ionization mass spectrometry of PCR products) or real-time PCR. Microarray formats include probes spotted or synthesized onto solid matrices or bead based formats, including but not limited to, slide arrays (Agilent Technologies), in situ synthesized microarrays (Affymetrix), bead arrays (Illumina) and coded beads detected by flow cytometry using XTag technology (Luminex). Real-time detection methods for PCR include, but are not limited to, detection with SYBR green, Taqman assays, Molecular Beacons, Sunrise primers, Scorpion primers, Light-up probes and the AmpiProbe (Enzo Life Sciences) system described in U.S. Pat. No. 8,247,179. See also, Hofstadler et al. (2005) Int J. Mass Spec. 242; 23-41; Wilhelm et al. (2003) ChemBioChem 4; 1120-1128; Arya et al. (2005) Expert Rev. Molec. Diagn. 5; 209-219.

In various embodiments, nucleic acid amplification can be accomplished by isothermal methods. Such isothermal amplification methods that can be used in the methods described herein include, but are not limited to, a Self-Sustained Sequence Reaction (3SR), a Nucleic acid Based Transcription Assay (NASBA), a Transcription Mediated Amplification (TMA), a Strand Displacement Amplification (SDA), a Helicase-Dependent Amplification (HDA), a Loop-Mediated isothermal amplification (LAMP), stem-loop amplification, signal mediated amplification of RNA technology (SMART), isothermal multiple displacement amplification (IMDA), a single primer isothermal amplification (SPIA), and a circular helicase-dependent amplification (cHDA). See, e.g., Notomi et al. (2000) Nucl. Acids Res. 28:e63; U.S. Pat. No. 6,743,605; Gill et al., (2008) Nucleosides, Nucleotides, and Nucleic Acids 27:224-243. The skilled artisan will understand that most signal generation systems typically used for PCR can be applied to end-point and real-time detection methods using isothermal amplification systems.

In various embodiments, viral nucleic acid targets for detection in the methods described herein include any nucleic acid sequence that is present in the genome of Herpesvirus saimiri or a related virus, but not the genome of unrelated viruses that infect humans, or in the human genome. Accordingly, probes for detection of virus can be designed to specifically bind to such unique sequences. Sequences that may also be included for this purpose include fusion products derived from splicing of mRNA species of Herpesvirus saimiri or a related virus where the junctions generate new sequences that are only partially present in the genome. In particular embodiments, viral nucleic acid targets for detection of a virus in the methods described herein preferably include a nucleic acid target that is conserved between virus strains, such as nucleic acid targets that code for proteins involved in virus replication or viral assembly. Accordingly, in some embodiments, the nucleic acid target is selected from major single-stranded DNA binding protein (mDNA-BP) gene sequences, DNA polymerase gene sequences, DNA packaging terminase gene sequences, helicase-primase complex gene sequences, uracil DNA glycosylase gene sequences, deoxyuridine triphosphatase (dUTPase) gene sequences, DNA polymerase processivity factor gene sequences, and capsid assembly and DNA maturation protein gene sequences. In other embodiments, the nucleic acid target is selected from TER gene sequences, STP gene sequences, repeat sequences of the virus, and sequences of genes that have been adopted by the virus from mammalian systems, such as, IL-17 gene sequences, Cyclin D gene sequences, dihydrofolate reductase (DHFR) gene sequences, and thymidylate synthase gene sequences. In still other embodiments, the nucleic acid target is selected from glycoprotein B gene sequences, Sag gene sequences, CD59 gene sequences, Bcl2 gene sequences, capsid protein gene sequences, envelope protein gene sequences, ribonucleotide reductase gene sequences, tegument protein gene sequences, FLICE interacting protein (FLIP) gene sequences, IL-8 receptor gene sequences, glycoprotein M gene sequences, and FGARAT gene sequences. In additional embodiments, the nucleic acid target is selected from thymidine kinase gene sequences, phosphotransferase gene sequences, and tyrosine kinase gene sequences. In various embodiments, viral nucleic acid targets for detection of Herpesvirus saimiri or a related virus in the methods described herein include any gene in the viral genome. In other embodiments of the present disclosure, amplification is carried out with primers that amplify a variety of different viral sequences and identification of the particular type of herpesvirus is carried out with one or more species-specific probes or by restriction enzyme digestion. Examples of such techniques are described by VanDevanter et al. (1996) J. Clin. Micro. 34:1666-1671; Chmielewicz et al. (2001) Virus Research 75:87-94.

It will be evident to the skilled artisan that unique sequences of a virus can be identified by comparing the degree of complementarity between a reference sequence from the virus genome with human and/or unrelated virus sequences. In determining the degree of "complementarily" between the virus and unrelated virus or human nucleic acids, the degree of "complementarity" (also, "homology") is expressed as the percentage identity between the sequence of the virus sequence (or region thereof) and the reverse complement of the sequence of the region of the human or unrelated virus nucleic acid that best aligns therewith. The percentage is calculated by counting the number of aligned bases that are identical as between the 2 sequences, dividing by the total number of contiguous monomers in the reference sequence, and multiplying by 100. Polynucleotide alignments, percentage sequence identity, and degree of complementarity may be determined for purposes of the invention using the ClustalW algorithm using standard settings: see http://www.ebi.ac.uk/emboss/align/index.html, Method: EMBOSS::water (local): Gap Open=10.0, Gap extend=0.5, using Blosum 62 (protein), or DNAfull for nucleotide/nucleobase sequences. Also useful for this purpose are various forms of BLAST searches available by NCBI at http://blast.ncbi.nlm.nih.gov/Blast.cgi.

In various embodiments in which the method comprises detecting more than one virus nucleic acid, the detection of the plurality of nucleic acids may be detected concurrently or simultaneously in the same assay reaction. In some embodiments, the detection of the plurality of nucleic acids is carried out concurrently or simultaneously in separate reactions. In some embodiments, detection is carried out at different times, such as in serial assay reactions.

In some embodiments, the methods of detecting a nucleic acid of Herpesvirus saimiri or a related virus described herein employ one or more modified oligonucleotides. In certain embodiments, the oligonucleotides comprise one or more affinity-enhancing nucleotides. Modified oligonucleotides for use in the methods described herein include probes and primers for reverse transcription and/or amplification. In some embodiments, the incorporation of affinity-enhancing nucleotides increases the binding affinity and specificity of an oligonucleotide for its target nucleic acid as compared to oligonucleotides that contain only deoxyribonucleotides, and allows for the use of shorter oligonucleotides or for shorter regions of complementarity between the oligonucleotide and the viral nucleic acid.

In some embodiments, affinity-modulating nucleotides include nucleotides comprising one or more base modifications, sugar modifications and/or backbone modifications.

In some embodiments, modified bases for use in affinity-modulating nucleotides include 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.

In other embodiments, affinity-modulating modifications include nucleotides having modified sugars such as 2'-substituted sugars, such as 2'-O-alkyl-ribose sugars, 2'-amino-deoxyribose sugars, 2'-fluoro-deoxyribose sugars, 2'-fluoro-arabinose sugars, and 2'-O-methoxyethyl-ribose (2'MOE) sugars. In some embodiments, modified sugars are arabinose sugars, or d-arabino-hexitol sugars.

In still other embodiments, affinity-modulating modifications include backbone modifications such as peptide nucleic acids (e.g., an oligomer including nucleobases linked together by an amino acid backbone). Other backbone modifications include phosphorothioate linkages, phosphodiester modified nucleic acids, combinations of phosphodiester and phosphorothioate linkages, methylphosphonates, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof.

In some embodiments, the oligomer includes at least one affinity-enhancing nucleotide that has a modified base, at least one nucleotide (which may be the same nucleotide) that has a modified sugar, and at least one internucleotide linkage that is non-naturally occurring.

In some embodiments, the affinity-enhancing oligonucleotide contains a locked nucleic acid ("LNA") sugar, which is a bicyclic sugar. In some embodiments, an oligonucleotide for use in the methods described herein comprises one or more nucleotides having an LNA sugar. In some embodiments, the oligonucleotide contains one or more regions consisting of nucleotides with LNA sugars. In other embodiments, the oligonucleotide contains nucleotides with LNA sugars interspersed with deoxyribonucleotides. See, e.g., Frieden, M. et al. (2008) Curr. Pharm. Des. 14(11):1138-1142.

In certain embodiments, the oligomer includes at least one universal base, i.e., a base that can base pair with more than one complementary base, were first used in oligonucleotides to maintain stable hybridization with target nucleic acids that had ambiguity in the identity of their nucleotide sequence. A well-known example of this is the substitution of inosine in PCR primes (Liu and Nichols, (1994) Biotechniques 16; 24-26). Inosine has the property of being able to base pair efficiently with either G, A, T or C in a complementary strand (Kawase et al., 1986, Nucl. Acids Res. 19;

7727-7736). The melting temperature is less than a normal base pairing but still higher than a mismatch. When used as a template, inosine is recognized as if it was effectively G and a C is preferentially incorporated into the complementary copy. Other analogs of nucleotides that can act as universal bases have also been described. For instance, 5-nitroindolenine and 3-nitopyrrole analogues have also been described as universal bases (Loakes and Brown, 1994, Nucl. Acids Res. 22; 4039-4043, Nichols et al., 1994, Nature 369; 492-493 both of which are incorporated by reference). The use of these and other universal bases are reviewed by Loakes (2001) in Nucl. Acids Res. 29; 2437-2447 (incorporated by reference). The ability of universal bases to add stability without adding to the complexity of primers has been described by Ball et al., (1998, Nucl. Acids Res. 26; 5225-5227, incorporated by reference) where the addition of 5-nitroindolenine residues at the 5' end, improved the specificity and signal intensity of octamer primers used for cycle sequencing. Thus, these and other universal bases may all find use in the present invention.

In another embodiment of the present invention, a protein is detected. In some embodiments, the protein is a virus-specific protein. In certain embodiments, the virus-specific protein is an analog of a human protein. In particular embodiments, the protein to be detected is selected from IL-17, thymidylate synthase, dihydrofolate reductase, cyclin D, STP, Sag, CD59, Bcl2, FGARAT, FLIP, a peptide derived from any of the foregoing and combinations thereof. In other particular embodiments, the protein to be detected is a viral envelope protein or a capsid protein such as VP23, glycoprotein M, and FGARAT, a peptide derived from any of the foregoing, and combinations thereof. Accordingly, in various embodiments, the presence of virus-specific proteins is detected by immunological methods. Immunological reagents that bind to viral antigens (e.g., proteins or peptides) can be generated and selected by any method taught in the art. Such reagents include, but are not limited to, antibodies and antibody fragments such as Fab, Fab', F(ab)$_2$ and Fv fragments, diabodies, tribodies, linear antibodies, single chain antibody molecules (e.g. scFv) and multi-specific antibodies formed by fusions of antibody fragments. See, e.g., Holliger et al. (2005) Nature Biotechnology 23:1126-1136.

Methods of selecting appropriate antigen binding reagents, e.g., antibodies that recognize viral antigens, but that do not cross-react with unrelated viral antigens or human antigens, can be accomplished by any method known in the art. Accordingly, in some embodiments, an antibody is developed by immunizing a mammalian host, e.g., a goat or rabbit, with one or more viral proteins or peptides and, after a suitable time period (and possible booster shots), identifying cells that secrete an appropriate antibody. In other embodiments, an artificial system for antigen binding reagent selection, such as library displays, can be used. In these embodiments, pre-made antibody libraries are screened for reactivity to a specific antigen. In some embodiments, negative selection can be used to eliminate antigen binding reagents that have affinity for inappropriate targets. See, e.g., Hoogenboom (2005) Nature Biotechnology 23:1105-1116. The skilled artisan will understand that an appropriate antigen binding agent for detection of virus-specific proteins will react with the protein of Herpesvirus saimiri or a related virus, but not with the human protein or with a protein from an unrelated virus.

In some embodiments, the antibody is a primary antibody for direct detection of the viral antigen. In other embodiments, detection is carried out by a secondary antibody that binds to the primary antibody in an immunoassay. Secondary antibodies can be any antibody that binds to a constant region of the primary antibody, including but not limited to, an anti-mouse antibody, an anti-rabbit antibody, an anti-goat antibody and the like. Antibodies can be labeled by any method known in the art. In certain embodiments, a label, e.g., a fluorescent dye, a chemiluminescent compound, a radioactive label, a hapten label, a chromogenic label, an energy transfer pair, or a compound that can be detected by binding to a labeled binding partner, such as biotin, avidin or streptavidin, is covalently attached, either directly or through a linker arm (e.g., maleimide), to either the primary or secondary antibody. In various embodiments, a label is non-covalently bound to a primary antibody or a secondary antibody. In still other embodiments, the primary antibody or the secondary antibody is covalently or non-covalently bound to an enzyme whose presence can be detected by the addition of a substrate that the enzyme converts to a detectable product. Non-limiting examples of such enzymes include, but are not limited to, alkaline phosphatase, horseradish peroxidase, and luciferase.

Antibodies for detection and/or quantification of virus-specific elements can be used in any assay known in the art for detection of proteins of interest, including enzyme-linked immune sorbent assays ("ELISA"), such as indirect ELISA, sandwich ELISA, competitive ELISA and multiple and portable ELISA, histological detection, protein chip arrays and bead assays. A variety of different assay formats for detecting proteins and various means of signal generation are discussed in Pei et al. (2012) Analytica Chimica Acta 758:1-18.

As discussed above, the antibodies referred to herein can be any type of antibody, including, but not limited to polyclonal, monoclonal, chimeric human, humanized, multispecific, primatized, a single chain or an antibody fragment such as Fab, ScFv, Fab', F(ab')2, Fv, Fv(ab)$_2$ or combinations thereof. See, e.g., Hollinger & Hudson (2005) Nature Biotechnol. 23(9):1126-1136 for a review of useful engineered antibody fragments and single antibody domains. Antibodies for use in the present invention can be developed and isolated by any method known in the art. In certain embodiments, antibodies can be identified by screening of recombinant antibody libraries using, for example, platforms such as phage display, ribosome and mRNA display, microbial cell (such as yeast cell) display, and directed evolution platforms such as retroviral display, display based on protein-DNA linkage, microbead display by in vitro compartmentalization, in vivo-based growth selection based on the protein fragment complementation assay (PCA) or other systems and single-molecule sorting. Selection procedures include identification and selection of antibodies that bind to specific antigens, selection of antibodies with improved binding affinity or kinetics toward a target antigen, and screening of target-binding properties of particular antibodies. In certain embodiments, the antibody is optimized by, for example, affinity maturation, humanization, selection for biophysical properties (e.g., thermostability, resistance to proteases, etc.). See Hoogenboom et al. (2005) Nature Biotechnol 23(9):1105-1116 for a review of selection and screening methods and antibody optimization strategies. In particular embodiments, antibodies to structural and/or non-structural proteins from Herpesvirus saimiri, a related virus or a novel virus can be obtained or identified by any method known in the art. In various embodiments, anti-viral antibodies can be obtained by immunizing mice with purified virions and creating hybridomas for screening to identify hybridomas secreting specific antibodies to viral antigens and binding can be characterized by known methods, such as Western blotting. See, e.g., Dahlberg et al. (1985) J Virol 53(1):279-286 for exemplary methods of producing and characterizing monoclonal antibodies to Herpesvirus saimiri proteins. In still other embodiments, antibodies can be identified and/or characterized using recombinant viral proteins. See, e.g., Randall et al. (1984) J Virol 52(3):872-883. Recombinant viral proteins, such as viral IL-17 can be obtained by known methods or are available from commercial sources. See, e.g., MyBioSource.com at http://www-.mybiosource.com/advanced_search_result.php?keywords=interleukin%2017,%20il-17%20herpesvirus%20saimiri&target=13&search_in=name for a source of recombinant viral IL-17 from Herpesvirus saimiri.

In certain embodiments, the virus-specific protein is an enzyme and is detected using an enzyme activity assay. Enzyme assays can be performed by any method known in the art, including, but not limited to, spectrophotometric assays (including colorimetric assays such as an MTT assay), fluorometric assays, calorimetric assays, chemiluminescent assays, light scattering assays, microscale thermophoresis assays, radiometric assays and chromatographic assays. See, e.g., Bergmeyer (1974). Methods of Enzymatic Analysis 4. New York: Academic Press. pp. 2066-72; Passonneau et al. (1993). Enzymatic Analysis. A Practical Guide. Totowa N.J.: Humana Press. pp. 85-110; Todd et al. (2001). Anal. Biochem. 296 (2): 179-87; Churchwella et al. (2005) J Chromatog B 825 (2):134-143. Specific assays for Herpesvirus enzymes can be found, for example, in Nicholas et al. (1998) J Natl Cancer Inst Monogr. 23:79-88. In some embodiments, the enzyme is selected from thymidine kinase, phosphotransferase, tyrosine kinase, uracil DNA glycosylase, deoxyuridine triphosphatase, TS and DHFR.

In some embodiments where the viral protein is a viral analog of a human protein, a virus can be detected by detecting aberrant expression of the viral protein. As used herein "aberrant expression" refers to expression of a protein in a cell, tissue, organ or body fluid of a patient that does not normally produce the protein in a healthy individual (inappropriate expression) or expression of higher levels of a protein in a cell, tissue, organ or body fluid of a patient than are detected in the same type of cell, tissue, organ or body fluid of a healthy individual (differential expression). In various embodiments, aberrant expression is detected using an antibody that specifically binds to the viral protein, but not to the human protein. In other embodiments, aberrant expression is detected using an antibody that binds to both the human protein and the viral analog of the human protein. Accordingly, in certain embodiments where the antibody binds to both the human protein and the viral analog, the detected aberrant expression is at least about 10%, such as at least about 15%, such as at least about 20%, such as at least about 25%, such as at least about 30%, such as at least about 35%, such as at least about 40%, such as at least about 45%, such as at least about 50% or greater than expression of the human protein in a healthy individual. It will be understood by the skilled artisan, that in some embodiments, a peptide of a viral protein can also be detected in the disclosed methods. In various embodiments, aberrant expression is detected in an immunological assay, such as ELISA. In situ detection may also be carried out for detection in cells where undetectable levels are seen only in the absence of disease. In still other embodiments in which the protein is an enzyme, aberrant expression is detected by affinity purification followed by an enzyme assay.

In certain embodiments where the viral protein is an enzyme that is a viral analog of a human enzyme, a virus can be detected by detecting aberrant expression of a metabolite of the enzyme. Accordingly, in some embodiments, the metabolite is detected by inappropriate expression in a cell, tissue, organ or body fluid of a patient that does not normally produce the metabolite in a healthy individual. In other embodiments, the metabolite is detected by differential expression, such as expression of higher levels of the metabolite in a cell, tissue, organ or body fluid of a patient than are detected in the same type of cell, tissue, organ or body fluid of a healthy individual. Accordingly, in certain embodiments, the detected aberrant expression of the metabolite is at least about 10%, such as at least about 15%, such as at least about 20%, such as at least about 25%, such as at least about 30%, such as at least about 35%, such as at least about 40%, such as at least about 45%, such as at least about 50% or greater than expression of the metabolite in a healthy individual. Methods of detecting and/or quantifying enzyme metabolites are known in the art. Such methods include, but are not limited to, gas chromatography, high performance liquid chromatography, capillary electrophoresis, mass spectrometry, surface-based mass analysis such as MALDI and secondary ion mass spectrometry (SIMS), desorption electrospray ionization (DESI) and nuclear magnetic resonance (NMR). Schauer et al. (2005) FEBS Lett. 579(6):1332-7; Gika et al. (2007) J. Proteome Res. 6(8): 3291-303; Soga et al. (2003) J. Proteome Res. 2(5):488-494; Northen et al. (2007) Nature 449(7165):1033-6; Woo et al. (2008) Nature Protocols 3 (8):1341-9; Griffin (2003) Curr Opin Chem Biol 7(5):648-54; Beckonert et al. (2007) Nat Protoc 2(11):2692-703.

In various embodiments, detection of a virus-specific protein, peptide or metabolite comprises a step of separating and/or purifying the protein, peptide or metabolite to be measured. In particular embodiments, the method includes a step of quantifying the protein, peptide or metabolite. Separation and/or purification of proteins, peptides and/or metabolites can be accomplished by any method known in the art, including, but not limited to, liquid chromatography techniques (e.g., HPLC, affinity chromatography, size-exclusion chromatography, ion-exchange chromatography and combinations thereof), electrophoresis (e.g., capillary electrophoresis, gel electrophoresis and the like) and immunological methods (e.g., antibody capture). Methods of quantifying a protein, peptide or metabolite can be accomplished by any method known in the art, including, but not limited to, quantitative mass spectrometry, two-dimensional gel electrophoresis, immunoassay (e.g., ELISA) and the like.

In various embodiments, the viral protein is a cytokine. In some embodiments, the cytokine is a viral analog of a human cytokine. In certain of these embodiments, detection of a viral analog of a human cytokine can be performed using an antibody that binds to the viral cytokine but not to the human cytokine. In other embodiments, detection can be performed using an antibody that binds to both the viral cytokine and the human cytokine. In still other embodiments, the viral cytokine is detected in a cell proliferation assay, such as a T-cell proliferation assay. T-cell proliferation can be measured by any method known in the art, such as by cell counting using flow cytometry, [41]-thymidine uptake and the like. Various methods for measuring T-cell proliferation can be found for example in U.S. patent application Ser. No. 13/871,730 and references cited therein.

In various embodiments, a patient antibody to a virus-specific element is detected. In some embodiments, the virus-specific element is part of the viral envelope. In other embodiments, the virus-specific element is part of the viral capsid. In other embodiments, the virus-specific element is not part of the viral envelope or the viral capsid, but can be released from the interior of the virus, for example, by dissociation of the viral particles. In other embodiments, the virus-specific element is released by during lysis of a host cell. In some embodiments, the presence of a patient antibody to the virus is indicative of latency of viral infection. In other embodiments, the presence of a patient antibody to the virus is indicative of exposure to the virus in the absence of established infection. Patient antibodies to a virus-specific element can be detected and/or quantified by any method known in the art, including, but not limited to, Western blotting, ELISA, a microparticle enzyme immunosorbent assay, a magnetic immunoassay, and an ELISPOT assay. Other methods for detection of patient antibodies can be found in Corchero et al. (2001) Clinical and Diagnostic Laboratory Immunol. 8(5):913-921.

In other embodiments, the virus or a cell infected by the virus is detected. In certain embodiments, the virus is detected using an antibody that specifically binds to an envelope protein or a capsid protein of the virus. In some embodiments, the virus is detected in an immunoassay, such as an ELISA assay. In other embodiments, the virus is detected by flow cytometry. In some embodiments, the cells are derived from tissue. In some embodiments, serum or whole blood is analyzed. In other embodiments, peripheral blood cells are examined for the presence of virus. In these embodiments, peripheral blood is obtained from a patient and mononuclear cells are separated, e.g., by centrifugation onto Ficoll-Hypaque. The cell layer at the interface is removed, washed in phosphate-buffered saline without $Ca^{2+}$ and $Mg^{2+}$, and fixed with 90% methanol, and intracellular viral antigens are detected, e.g., by indirect immunofluorescence with antibodies to viral antigens as the primary antibody and a labeled secondary antibody and/or by flow cytometry.

5.3. Kits for Diagnosing or Prognosticating a Viral Disease, Monitoring Disease Progression and Monitoring the Efficacy of Therapy In some embodiments, the present disclosure relates to kits for diagnosing or prognosticating a viral disease in a patient. In other embodiments, the present disclosure relates to kits for monitoring disease progression and/or monitoring the efficacy of therapy in a patient. In various embodiments, the kits are for detection of Herpesvirus saimiri or a related virus in a clinical sample from a patient. In certain embodiments, the kit comprises one or more reagents for detecting a virus-specific nucleic acid. In other embodiments, the kit comprises one or more reagents for detecting a virus-specific protein, peptide or metabolite in a clinical sample. In still other embodiments, the kit comprises one or more reagents for detecting a patient antibody to a virus-specific element. In certain embodiments, the kits are for detection of Herpesvirus saimiri or a Herpesvirus saimiri-specific element. In other embodiments, the kits are for detection of a related virus, or a related virus-specific element.

In certain embodiments where the kit is for detection of virus-specific nucleic acids, the kit includes oligonucleotide probes that specifically bind to a virus-specific nucleic acid. In some embodiments, the oligonucleotide probes comprise one or more affinity-modulating nucleotides. Such affinity-enhancing nucleotides include nucleotides comprising one or more base modifications, sugar modifications and/or backbone modifications. In some embodiments, modified bases for use in affinity-enhancing nucleotides include 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine. In other embodiments, affinity-enhancing modifications include nucleotides having modified sugars such as 2'-substituted sugars, such as 2'-O-alkyl-ribose sugars, 2'-amino-deoxyribose sugars, 2'-fluoro-deoxyribose sugars, 2'-fluoro-arabinose sugars, and 2'-O-methoxyethyl-ribose (2'MOE) sugars. In some embodiments, modified sugars are arabinose sugars, or d-arabino-hexitol sugars.

In still other embodiments, affinity-modulating modifications include backbone modifications such as peptide nucleic acids (e.g., an oligomer including nucleobases linked together by an amino acid backbone). Other backbone modifications include phosphorothioate linkages, phosphodiester modified nucleic acids, combinations of phosphodiester and phosphorothioate linkages, methylphosphonates, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof. In some embodiments, the affinity-enhancing oligonucleotide contains a locked nucleic acid ("LNA") sugar, which is a bicyclic sugar. In some embodiments, an oligonucleotide for use in the methods described herein comprises one or more nucleotides having a modified backbone, e.g., an LNA or a peptide nucleic acid. In other embodiments, the oligonucleotide contains one or more regions consisting of nucleotides with modified backbones. In various embodiments, all of the nucleotides have a modified backbone. In other embodiments, the oligonucleotide contains nucleotides having a modified backbone interspersed with deoxyribonucleotides. See, e.g., Frieden, M. et al. (2008) Curr. Pharm. Des. 14(11):1138-1142.

In some embodiments, the probes include at least one affinity-modulating nucleotide that has a modified base, at least one nucleotide (which may be the same nucleotide) that has a modified sugar, and at least one internucleotide linkage that is non-naturally occurring.

In some embodiments, the virus-specific probes for inclusion in the kit are lyophilized and can be reconstituted in an appropriate buffer. In other embodiments, the virus-specific probes are bound to a solid support, e.g., an addressable array or magnetic beads.

In some embodiments, where the kit is for detection of viral nucleic acids, the kit may further include one or more reagents for amplifying a nucleic acid of interest. Such one or more reagents may include, but is not limited to, virus-specific primers and a polymerase.

In other embodiments, the kits are for detection of a virus-specific protein, peptide or metabolite. In some embodiments, the kits are for detection and quantification of a virus-specific protein, peptide or metabolite, for example, to detect inappropriate expression or differential expression of a virus-specific protein, a peptide derived from a virus-specific protein or a metabolite. In these latter embodiments, the kit can include one or more reagents for quantification of a protein, peptide or metabolite, such as a Bradford reagent or antibody that specifically binds to a virus-specific protein, peptide or metabolite. In various embodiments, the virus-specific protein is from Herpesvirus saimiri or a related virus and the antibody specifically binds to a viral protein selected from IL-17, TS, DHFR, cyclin D, Sag, CD59, Bcl2, FGARAT, FLIP, a viral envelope protein, a viral capsid protein, a protein involved in viral replication, or a peptide derived from any of these proteins. In various embodiments, the virus-specific element is a virus-specific metabolite. In these embodiments, the metabolite is a product of a virus-specific enzyme, such as thymidylate synthase, dihydrofolate reductase, thymidine kinase, phosphotransferase, tyrosine kinase, uracil DNA glycosylase, or deoxyuridine triphosphatase.

In some embodiments, the kit includes an immunological reagent that specifically binds to a virus-specific protein, peptide or metabolite, for example, an antibody or antibody fragment such as Fab, Fab', F(ab)$_2$, an Fv fragment, a diabody, a tribody, a linear antibody, a single chain antibody molecule (e.g. scFv) or a multi-specific antibody formed by fusions of antibody fragments. See, e.g., Holliger et al. (2005) Nature Biotechnology 23:1126-1136. In certain embodiments, the kit includes a primary antibody that specifically binds to a virus-specific protein, peptide or metabolite derived therefrom. In other embodiments, the kit includes a primary antibody that specifically binds to a virus-specific protein, peptide or metabolite derived therefrom and a secondary antibody that binds to the primary antibody. In various embodiments, the primary antibody and/or the secondary antibody is labeled. In other embodiments, the kit includes one or more reagents for labeling the primary antibody and/or the secondary antibody. In some embodiments, the label is selected from a fluorescent dye, a chemiluminescent compound, a radioactive label, a hapten label, a chromogenic label, an energy transfer pair, a compound that can be detected by binding to a labeled binding partner, such as biotin, avidin or streptavidin, and an enzyme whose presence can be detected by the addition of a substrate that the enzyme converts to a detectable product. In some embodiments, the label is covalently attached to the antibody. In other embodiments, the label is non-covalently attached to the antibody. In still other embodiments, the label is attached directly to the antibody. In some embodiments, the linker comprises a labeled nucleic acid. See, e.g., U.S. Pat. No. 7,514,551; U.S. Patent Publication No. 2010/0273145 and Zheng et al. (2007) Bioconjugate Chemistry 18:1668-1672. In yet other embodiments, the label is attached indirectly to the antibody through a linker arm. In some embodiments, the kit further includes standards for quantification of virus-specific proteins, peptides and/or metabolites.

In still other embodiments, the kits are for detection of human antibodies to Herpesvirus saimiri or a related virus. In some embodiments, the kit comprises an immunological reagent that specifically binds to a patient antibody raised against epitopes of Herpesvirus saimiri or a related virus. In other embodiments, the kit includes a primary antibody that specifically binds to a patient antibody raised against a virus, or peptide derived therefrom, and a secondary antibody that binds to the primary antibody. In various embodiments, the primary antibody and/or the secondary antibody is labeled. In other embodiments, the kit includes one or more reagents for labeling the primary antibody and/or the secondary antibody. In some embodiments, the label is selected from a fluorescent dye, a chemiluminescent compound, a radioactive label, a hapten label, a chromogenic label, an energy transfer pair, a compound that can be detected by binding to a labeled binding partner, such as biotin, avidin or streptavidin, and an enzyme whose presence can be detected by the addition of a substrate that the enzyme converts to a detectable product. In some embodiments, the label is covalently attached to the antibody. In other embodiments, the label is non-covalently attached to the antibody. In still other embodiments, the label is attached directly to the antibody. In yet other embodiments, the label is attached indirectly to the antibody through a linker arm. In some embodiments, the kit further includes standards for quantification of human anti-viral antibodies.

In various embodiments, the kits are for detection of Herpesvirus saimiri, a related virus and/or a host cell that is infected by the virus. In certain embodiments, the kit comprises an antibody that specifically binds to a virus envelope protein or a virus capsid protein. In other embodiments, the kit comprises an antibody that specifically binds to a viral marker on the surface of an infected host cell, e.g., a blood cell. In certain embodiments, for example, when the virus or infected cell is identified by immunoassay, the kit can further include a secondary antibody that binds to the primary antibody that binds to a cell-surface marker, a virus envelope protein or a virus capsid protein. In still other embodiments, the kit comprises one or more reagents, e.g., antibodies to host cell-surface and/or virus-envelope or capsid markers that are fluorescently labeled for use in flow cytometry, and in particular, fluorescence-activated cell sorting (FACs) based on the cell- or virus-envelope or capsid markers. In various embodiments, the kit may further include one or more antibody labeling reagents.

In other embodiments, the various kits described herein include one or more of (i) a cell line for culturing a virus; (ii) a cell growth medium; and/or (iii) a buffer. In certain embodiments, the cell line is a permissive cell line selected from owl monkey kidney cells, co-cultured epithelial cells and peripheral blood cells from naturally infected squirrel monkeys. In other embodiments, the cell line is a permissive cell line such as Raji B-cells, HFF fibroblasts and PANC-1 epithelial cells. In still other embodiments, the cell line is a semi-permissive cell line, e.g., T-cells such as Jurkat cells, CCRF-CEM and Molt 3 cells, B-cells such as BALL-1 and Daudi cells, epithelial cells such as 5673 or myeloid/erythroid cell lines including K562 and HEL 92.1.7 cells. See Simmer et al. (1991) J Gen. Vir. 72:1953-58.

5.4. Methods for Identifying a Therapeutic Agent for Treatment of a Viral Disease In certain embodiments, the present disclosure relates to a method of identifying a therapeutic agent for the treatment of a viral disease, which comprises the steps of (i) exposing a virus culture to an agent; (ii) measuring the replication or propagation of said virus culture; and (iii) comparing said replication or propagation measured in step (ii) with a the replication or propagation of a virus culture that has not been exposed to the agent, wherein replication or propagation measured in step (ii) that is lower than replication or propagation of the virus culture that has not been exposed to the agent identifies a therapeutic agent for the treatment of the viral disease. In certain specific embodiments, the virus culture is a Herpesvirus saimiri culture. In other specific embodiments, the virus culture is a related virus culture. In some embodiments, the viral disease is IPF. In other embodiments, the viral disease is a lymphoproliferative disease or cancer.

In various embodiments, in vitro assays are carried out in human T-lymphocytes. See Kaschka-Dierich et al. (1982) J Virol 44:295-310.

In certain embodiments, in vitro assays to measure the effect of a putative therapeutic agent on virus infectivity and/or replication comprise culturing a virus in a cell line that is permissive for viral infection. In some embodiments, permissive cell lines that can be used in the described methods include, but are not limited to, owl monkey kidney cells, and a co-culture of permissive epithelial cells with peripheral blood cells from naturally infected squirrel monkeys. Other cell lines that are useful for this purpose include permissive cell lines such as Raji B-cells, HFF fibroblasts and PANC-1 epithelial cells. In still other embodiments, the cell line is a semi-permissive cell line, e.g., T-cells such as Jurkat cells, CCRF-CEM and Molt 3 cells, B-cells such as BALL-1 and Daudi cells, epithelial cells such as 5673 or myeloid/erythroid cell lines including K562 and HEL 92.1.7 cells. See Simmer et al. (1991) J Gen. Vir. 72:1953-58.

In some embodiments, viral replication is measured by counting the number of virus particles or the number of infected host cells. Virus counting techniques include plaque assays, determination of the 50% Tissue Culture Infective Dose, a fluorescence focus assay (FFA), transmission electron microscopy and flow cytometry (such as fluorescence activated cell sorting using fluorescent labeled binding agents for virus surface antigens). See, e.g, Kaufmann et al. (2002) Methods in Microbiology Vol. 32: Immunology of Infection (Academic Press); Martin (1978). The Biochemistry of Viruses (Cambridge University Press); Flint et al. (2009) Principles of Virology. ASM Press; Malenovska (2013) J. Virological Methods, doi: 10.1016/j.jviromet.2013.04.008; Stoffel et al. (2005) American Biotechnology Laboratory 37 (22): 24-25.

In various embodiments, virus replication is measured by measuring an amount of viral nucleic acid. In some embodiments, the nucleic acid is viral DNA. In particular embodiments, the nucleic acid is Herpesvirus saimiri DNA. In other embodiments, the nucleic acid is viral mRNA. In particular embodiments, the nucleic acid is Herpesvirus saimiri mRNA. In various embodiments, the step of measuring viral replication is preceded by a step of amplifying viral nucleic acids. Exemplary methods for nucleic acid amplification and quantification are set forth in Section 6.2, supra.

In other embodiments, viral replication is measured by measuring an amount of viral protein and/or functional activity of a viral protein, e.g., by measuring an amount of a metabolite of the viral protein. In some embodiments, the assay quantifies the amount of total protein of the virus. In other embodiments, the assay quantifies the amount of a specific viral protein in the sample. In other embodiments, the assay quantifies the amount of functional activity of the viral protein. In some embodiments, the viral protein is involved in metabolism, and a functional assay can be carried out by measuring a metabolite produced by enzymatic activity. Examples of such viral proteins include thymidine kinase, phosphotransferase, tyrosine kinase, uracil DNA glycosylase, deoxyuridine triphosphatase, TS and DHFR. In other embodiments, the viral protein is involved in signal secretion, and a functional assay can be carried out by measuring a reporter gene that is influenced by cytokine/cytokine receptor binding. Examples of such viral proteins include IL-6 and IL-17. In various embodiments, the virus is Herpesvirus saimiri or a related virus and the viral protein that is measured is selected from IL-17, TS, cyclin D, Sag, CD59, Bcl2, FGARAT, FLIP, a viral envelope protein, a viral capsid protein, a protein involved in viral replication, and combinations thereof. In other embodiments, the metabolite is a product of a Herpesvirus saimiri or a related virus thymidine kinase, phosphotransferase, tyrosine kinase, uracil DNA glycosylase, deoxyuridine triphosphatase, TS or DHFR. In some embodiments, protein and/or metabolite detection and quantification is performed using an assay selected from a bicinchoninic acid assay, a single radial immunodiffusion assay, mass spectrometry, LabMap assays and ELISA. See, e.g., Smith et al. (1985) Anal. Biochem. 150 (1): 76-85; Rodda et al. (1981) Journal of Clinical Microbiology 14 (5): 479-482; Kemeny et al. (1988) ELISA and Other Solid Phase Immunoassays: Theoretical and Practical Aspects (John Wiley and Sons); Kuby et al. (2007) Kuby Immunology 6th edition (W.H. Freeman and Company); Dunbar et al. (2003) J Microb Methods 53:245-252. In still other embodiments, viral quantification is accomplished by measuring both viral nucleic acids and viral proteins, for example, by flow cytometry. See Stoffel et al. (2005) American Biotechnology Laboratory 37 (22): 24-25.

The skilled artisan will understand that the methods described herein can be used for de novo screening of therapeutic agents to determine their effects on a virus, or for screening of known drugs, e.g., known anti-viral agents, cytokine antagonists and the like. Screening can be from a library of agents. Screening can further be of modified versions of known drugs, e.g., known anti-viral agents or of combinations of known drugs. The skilled artisan will understand that the screening methods described herein are applicable to therapeutic agents and/or known drugs and/or modified versions of known drugs or therapeutic agents alone or in combination. Screening can also include virtual methods, such as structure-based drug design based on, e.g., the three-dimensional structure of a virus essential protein such as a DNA polymerase, followed by in vitro testing using the methods described herein.

5.5. Methods and Compositions for Treating a Viral Disease

The present inventors' unexpected discovery that the presence of Herpesvirus saimiri is strongly correlated with IPF, and certain lymphoproliferative diseases and cancers, in humans allows for new treatment approaches for these and other viral diseases. Anti-viral agents for use in the present invention include (i) agents that inhibit propagation of the virus; (ii) agents that neutralize a component of the virus; and (iii) agents that inhibit an enzyme of the virus.

Accordingly, in some embodiments, the present disclosure relates to methods and compositions for inhibiting propagation of Herpesvirus saimiri or a related virus. In certain embodiments, the compositions comprise an effective amount of a therapeutic agent identified by the methods described in Section 6.4. In various embodiments, the compositions include one or more therapeutic agents that are known anti-viral agents, e.g., acyclovir, vidarabine, idoxuridine, brivudine, cytarabine, foscarnet, docosanol, formivirsen, tromantidine, imiquimod, podophyllotoxin, cidofovir, interferon alpha-2b, peginterferon alpha-2a, ribavirin, moroxydine, valacyclovir, trifluridine, and bromovinyldeoxyuridine.

In some embodiments, the agent is an agent that inhibits replication of the virus, such as a nucleotide analog that is incorporated into DNA by the viral DNA polymerase and results in early chain termination. In other embodiments, the agent binds to and blocks one or more viral polymerases. In still other embodiments, the agent is directed to viral proteins responsible for viral DNA maturation (cleavage/packaging). In other embodiments, the agent inhibits episomal persistence of the viral genome. See Collins et al. (2002) J. Gen. Virol. 83:2269-78.

In other embodiments, the agent down-regulates expression of virus-specific proteins. In various embodiments, the virus-specific protein is selected from viral IL-17, viral IL-10, and the latency-associated nuclear antigen (LANA). Gene expression can be down-regulated by any method known in the art, including, but not limited to, by administering antisense DNA or antisense mRNA, by RNA interference (RNAi) and by the use of ribozymes to cleave RNA transcripts.

In other embodiments, the present disclosure relates to methods and compositions for neutralizing a component of Herpesvirus saimiri or a related virus. Accordingly, in some embodiments, the neutralizing agent is an antagonist of a viral protein, such as an agent that blocks one or more interactions of a viral protein with other viral proteins or with host proteins. In other embodiments, the neutralizing agent blocks activity of a specific viral protein. In certain embodiments, when the viral protein is a human homolog, the antagonist inhibits or down-regulates the viral analog without significantly impacting the human protein.

In certain embodiments, the neutralizing agent is an antibody. In various embodiments, the antibody is a monoclonal antibody. In other embodiments, the antibody is a polyclonal antibody. In various embodiments, the antibody is a human antibody. In still other embodiments, the antibody is a humanized antibody. In particular embodiments, the antagonist is an antibody to virus-specific IL-17. In some embodiments, the antibody is specific for variants of virus-specific IL-17. In specific embodiments, the antibody is specific for virus-specific IL-17A. In some embodiments, the neutralizing agent is an antibody to an IL-17 receptor (IL17R). In various embodiments, the IL17R antibody is specific for IL17RA. In other embodiments, the IL17R antibody is specific for IL17RB. In yet other embodiments, the IL17R is specific for IL17RC. In additional embodiments, the antibody is specific for more than one of IL17RA, IL17RB and IL17RC. In some embodiments, the neutralizing agent is IL-10 or an agonist of IL-10, such as isoproterenol, IT 9302 and combinations thereof. In other embodiments, the neutralizing agent is an inhibitor of IL-17 expression. In additional embodiments, the neutralizing agent is an inhibitor of expression of one or more IL-17 receptors.

In still other embodiments, the neutralizing agent is an antagonist of TGF-β. In certain embodiments, the antagonist is an antibody to TGF-β. In various embodiments, the antibody is a monoclonal antibody. In other embodiments, the antibody is a polyclonal antibody. In still other embodiments, the antibody is a human antibody. In further embodiments, the antibody is humanized. In some embodiments, the neutralizing agent is an antibody to a TGF-β receptor. In certain embodiments, the neutralizing agent is an inhibitor of TGF-β expression. In other embodiments, the neutralizing agent is an inhibitor of TGF-β receptor expression.

In various embodiments, the present disclosure relates to methods and compositions for treating a viral disease in a patient by administering an effective amount of a neutralizing agent that is an antagonist of IL-23. In certain embodiments, the neutralizing agent is an antibody to IL-23. In various embodiments, the antibody is a monoclonal antibody. In other embodiments, the antibody is a polyclonal antibody. In still other embodiments, the antibody is a human antibody. In further embodiments, the antibody is humanized. In some embodiments, the neutralizing agent is an antibody to an IL-23 receptor. In additional embodiments, the neutralizing agent is an inhibitor of IL-23 expression. In other embodiments, the neutralizing agent is an inhibitor of IL-23 receptor expression.

In certain embodiments, the present disclosure relates to methods and compositions for treating a viral disease in a patient by administering an effective amount of a neutralizing agent that is an antagonist of IL-1β. In certain embodiments, the neutralizing agent is an antibody to IL-1β. In various embodiments, the antibody is a monoclonal antibody. In other embodiments, the antibody is a polyclonal antibody. In still other embodiments, the antibody is a human antibody. In further embodiments, the antibody is humanized. In some embodiments, the neutralizing agent is Canakinumab. In other embodiments, the neutralizing agent is an inhibitor of IL-1β expression. In yet other embodiments, neutralizing agent is an inhibitor of IL-1β receptor expression.

In various embodiments, the present disclosure relates to methods and compositions for treating a viral disease in a patient by administering an effective amount of a neutralizing agent that is a soluble extra-cellular domain of a receptor of a viral protein, e.g., a viral cytokine. Accordingly, in some embodiments, the composition comprises a soluble IL-17R extra-cellular domain, such as a soluble IL17RA, IL17RB or IL17RC extra-cellular domains. In other embodiments, the composition comprises a soluble IL-R8 receptor extra-cellular domain. Without being bound by any particular theory, a soluble extra-cellular domain of a cytokine receptor competes with membrane-bound cytokine receptors on human cells for binding to the cytokine, thereby neutralizing the deleterious effects of viral cytokine production in the patient.

In various embodiments, the present disclosure relates to methods and compositions for treating a viral disease in a patient by administering an effective amount of an agent that inhibits virus entry into host cells. Accordingly, in some embodiments, the inhibitor is a small molecule, a peptide or a peptide mimetic of a host cell receptor that binds to a viral surface protein or glycoprotein and blocks binding of the virus to the host cell receptor. In other embodiments, the agent is a soluble extra-cellular domain of a host cell receptor. In still other embodiments, the inhibitor is a small molecule, a peptide or a peptide mimetic of a viral protein or glycoprotein that binds to a host cell receptor and blocks binding of the virus to the host cell receptor. In various embodiments, the agent is a soluble extra-cellular domain of a viral surface protein or glycoprotein. In still other embodiments, the agent is an antibody that binds to either a viral protein or glycoprotein or the host receptor to inhibit virus entry into the host cells. In various embodiments, the agent blocks entry of the virus into the cell.

In various embodiments, the present disclosure relates to methods and compositions for inhibiting an enzyme of Herpesvirus saimiri or a related virus. Accordingly, in some embodiments, the enzyme is selected thymidine kinase, phosphotransferase, tyrosine kinase, uracil DNA glycosylase, deoxyuridine triphosphatase, TS and DHFR. In certain embodiments, the viral inhibitor is a reversible inhibitor. In other embodiments, the viral inhibitor is an irreversible inhibitor. In various embodiments, the viral enzyme inhibitor is a competitive inhibitor and binds to the same site as the natural substrate. In other embodiments, the viral enzyme inhibitor is an uncompetitive inhibitor and binds only to the enzyme/substrate complex. In still other embodiments, the viral enzyme inhibitor is a mixed inhibition inhibitor where binding of the inhibitor affects the binding of the substrate, and vice versa. In yet other embodiments, the viral enzyme inhibitor is a non-competitive inhibitor that binds to the enzyme and reduces its activity but does not affect the binding of substrate.

In particular embodiments, the competitive inhibitor increases $K_m$. In some embodiments, the competitive inhibitor increases $K_m$ by at least about 5%, such as at least about 10%, such as at least about 15%, such as at least about 20%, such as at least about 25%, such as at least about 30%, such as at least about 35%, such as at least about 40%, such as at least about 45%, such as at least about 50%, such as at least about 55%, such as at least about 60%, such as at least about 65%, such as at least about 70%, such as at least about 75%, such as at least about 80%, such as at least about 85%, such as at least about 90%, such as at least about 95%, such as at least about 99% or more as compared to the $K_m$ of the enzyme in the absence of the inhibitor.

In other particular embodiments, the non-competitive inhibitor decreases $V_{max}$. In various embodiments, the non-competitive inhibitor decreases $V_{max}$ by at least about 5%, such as at least about 10%, such as at least about 15%, such as at least about 20%, such as at least about 25%, such as at least about 30%, such as at least about 35%, such as at least about 40%, such as at least about 45%, such as at least about 50%, such as at least about 55%, such as at least about 60%, such as at least about 65%, such as at least about 70%, such as at least about 75%, such as at least about 80%, such as at least about 85%, such as at least about 90%, such as at least about 95%, such as at least about 99% or more as compared to the $V_{max}$ of the enzyme in the absence of the inhibitor.

In still other embodiments, the mixed inhibition inhibitor increases $K_m$ and decreases $V_{max}$. In some embodiments, the mixed inhibition inhibitor increases $K_m$ by at least about 5%, such as at least about 10%, such as at least about 15%, such as at least about 20%, such as at least about 25%, such as at least about 30%, such as at least about 35%, such as at least about 40%, such as at least about 45%, such as at least about 50%, such as at least about 55%, such as at least about 60%, such as at least about 65%, such as at least about 70%, such as at least about 75%, such as at least about 80%, such as at least about 85%, such as at least about 90%, such as at least about 95%, such as at least about 99% or more as compared to the $K_m$ of the enzyme in the absence of the inhibitor. In various embodiments, the mixed inhibition inhibitor decreases $V_{max}$ by at least about 5%, such as at least about 10%, such as at least about 15%, such as at least about 20%, such as at least about 25%, such as at least about 30%, such as at least about 35%, such as at least about 40%, such as at least about 45%, such as at least about 50%, such as at least about 55%, such as at least about 60%, such as at least about 65%, such as at least about 70%, such as at least about 75%, such as at least about 80%, such as at least about 85%, such as at least about 90%, such as at least about 95%, such as at least about 99% or more as compared to the $V_{max}$ of the enzyme in the absence of the inhibitor. It will be understood that a mixed inhibition inhibitor, which interferes with substrate binding and catalysis in the enzyme-substrate complex, can have any combination of $K_m$ increase and $V_{max}$ decrease, e.g., $K_m$ is increased by 20% and $V_{max}$ is decreased by 50% or $K_m$ is increased by 10% and $V_{max}$ is decreased by 40%, etc.

In other embodiments, the inhibitor is an irreversible enzyme inhibitor. In various embodiments, the irreversible enzyme inhibitor covalently modifies an enzyme target. Such irreversible enzyme inhibitors include, but are not limited to, agents that have reactive functional groups such as aldehydes, haloalkanes, alkenes, Michael acceptors, phenyl sulfonates, or fluorophosphonates that covalently modify nucleophilic groups such as hydroxyl or sulfhydryl groups, e.g., on serine, cysteine, threonine or tyrosine, to destroy enzyme activity.

In some embodiments, one or more of the therapeutic agents described herein is administered to a subject who has a viral infection. In some embodiments, the patient has developed disease. In other embodiments, the disease is developing in the patient. In still other embodiments, the patient is asymptomatic. In certain embodiments, the patient is suffering from interstitial lung disease. In yet other embodiments, the patient evidences a usual interstitial pneumonia pattern on high-resolution computed tomography (HRCT). In further embodiments, the patient has one or more potential risk factors for a viral disease, such as cigarette smoking, environmental exposure, chronic viral infection, and abnormal gastroesophageal reflux. In other embodiments, the patient is suffering from a lymphoproliferative disease or cancer.

When administered to a patient, a therapeutic agent can be administered as a component of a composition that comprises a pharmaceutically acceptable carrier or excipient. Compositions comprising the compound can be administered by absorption through mucocutaneous linings (e.g., oral, rectal, and intestinal mucosa, etc.). Administration can be systemic or local. Methods of administration include, but are not limited to, intradermal, intramuscular, intraperitoneal, parenteral, intravenous, subcutaneous, intranasal, epidural, oral, sublingual, intracerebral, intravaginal, transdermal, rectal, by inhalation, or topical.

In certain embodiments, the therapeutic agent is administered by pulmonary administration, e.g., by use of an inhaler or nebulizer, and formulation with an aerosolizing agent, or via perfusion in a fluorocarbon or synthetic pulmonary surfactant. In certain embodiments, a therapeutic agent can be formulated as a suppository, with traditional binders and excipients such as triglycerides.

When a therapeutic agent is incorporated for parenteral administration by injection (e.g., continuous infusion or bolus injection), the formulation for parenteral administration can be in the form of a suspension, solution, emulsion in an oily or aqueous vehicle, and such formulations can further comprise pharmaceutically necessary additives such as one or more stabilizing agents, suspending agents, dispersing agents, and the like. A therapeutic agent can also be in the form of a powder for reconstitution as an injectable formulation.

In yet another embodiment, a therapeutic agent can be delivered in a controlled-release system or sustained-release system (see, e.g., Goodson, "Dental Applications" (pp. 115-138) in Medical Applications of Controlled Release, Vol. 2, Applications and Evaluation, R. S. Langer and D. L. Wise eds., CRC Press (1984)). Other controlled or sustained-release systems discussed in the review by Langer, Science 249:1527-1533 (1990) can be used.

The compositions can optionally comprise a suitable amount of a pharmaceutically acceptable excipient so as to provide the form for proper administration to the subject. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to the subject. Water is a particularly useful excipient when a therapeutic agent is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The compositions, if desired, can also contain minor amounts of wetting or emulsifying agents, or pH buffering agents. Specific examples of pharmaceutically acceptable carriers and excipients that can be used to formulate oral dosage forms are described in the Handbook of Pharmaceutical Excipients, American Pharmaceutical Association (1986).

The compositions can take the form of solutions, suspensions, emulsions, tablets, pills, pellets, capsules, capsules containing liquids, powders, sustained release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described in Remington's Pharmaceutical Sciences 1447-1676 (Alfonso R. Gennaro ed., 19th ed. 1995).

In one embodiment, the therapeutic agent is formulated in accordance with routine procedures as a composition adapted for oral administration. A therapeutic agent to be orally delivered can be in the form of tablets, capsules, gelcaps, caplets, lozenges, aqueous or oily solutions, suspensions, granules, powders, emulsions, syrups, or elixirs, for example. When a therapeutic agent is incorporated into oral tablets, such tablets can be compressed tablets, tablet triturates (e.g., powdered or crushed tablets), enteric-coated tablets, sugar-coated tablets, film-coated tablets, multiply compressed tablets or multiply layered tablets. Techniques and compositions for making solid oral dosage forms are described in Pharmaceutical Dosage Forms: Tablets (Lieberman, Lachman and Schwartz, eds., 2nd ed.) published by Marcel Dekker, Inc. Techniques and compositions for making tablets (compressed and molded), capsules (hard and soft gelatin) and pills are also described in Remington's Pharmaceutical Sciences 1553-1593 (Arthur Osol, ed., 16th ed., Mack Publishing, Easton, Pa. 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in Pharmaceutical Dosage Forms: Disperse Systems, (Lieberman, Rieger and Banker, eds.) published by Marcel Dekker, Inc.

When a therapeutic agent is to be injected parenterally, it can be, e.g., in the form of an isotonic sterile solution. Alternatively, when a therapeutic agent is to be inhaled, it can be formulated into a dry aerosol or can be formulated into an aqueous or partially aqueous solution.

An orally administered composition can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, wherein tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the therapeutic agent can be formulated for intravenous administration. Typically, compositions for intravenous administration comprise sterile isotonic aqueous buffer. Where necessary, the compositions can also include a solubilizing agent. A therapeutic agent for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where a therapeutic agent is to be administered by infusion, it can be dispensed, for example, with an infusion bottle containing sterile pharmaceutical grade water or saline. Where a therapeutic agent is administered by injection, an ampule of sterile water for injection or saline can be provided so that the ingredients can be mixed prior to administration.

A therapeutic agent can be administered by controlled-release or sustained-release means or by delivery devices that are known to those in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566. Such dosage forms can be used to provide controlled or sustained release of one or more active ingredients using, for example, hydroxypropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled or sustained-release formulations known to those in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled or sustained-release.

Controlled or sustained-release compositions can initially release an amount of a therapeutic agent that promptly produces the desired therapeutic or prophylactic effect, and gradually and continually release other amounts of the therapeutic agent to maintain this level of therapeutic or prophylactic effect over an extended period of time. To maintain a constant level of the therapeutic agent in the body, the agent can be released from the dosage form at a rate that will replace the amount of agent being metabolized and excreted from the body. Controlled or sustained-release of an active ingredient can be stimulated by various conditions, including but not limited to, changes in pH, changes in temperature, concentration or availability of enzymes, concentration or availability of water, or other physiological conditions or compounds.

The amount of therapeutic agent can be determined by standard clinical techniques. In addition, in vitro and/or in vivo assays can optionally be employed to help identify optimal dosage ranges. The precise dose to be employed will also depend on, e.g., the route of administration and the seriousness or stage of the condition, and can be decided according to the judgment of a practitioner and/or each patient's circumstances. In other examples thereof, variations will necessarily occur depending upon the weight and physical condition (e.g., hepatic and renal function) of the patient being treated, the severity of the symptoms, the frequency of the dosage interval, the presence of any deleterious side-effects, and the particular agent utilized, among other things.

Administration can be as a single dose or as a divided dose. In one embodiment, an effective dosage is administered once per month until the disease is abated. In another embodiment, the effective dosage is administered once per week, or twice per week or three times per week until the disease is abated. In another embodiment, an effective dosage amount is administered about every 24 h until the disease is abated. In another embodiment, an effective dosage amount is administered about every 12 h until the disease is abated. In another embodiment, an effective dosage amount is administered about every 8 h until the disease is abated. In another embodiment, an effective dosage amount is administered about every 6 h until the disease is abated. In another embodiment, an effective dosage amount is administered about every 4 h until the disease is abated. The effective dosage amounts described herein refer to total amounts administered; that is, if more than one agent is administered, the effective dosage amounts correspond to the total amount administered.

In various embodiments, the therapeutic agent can be administered together with a second therapeutically active agent. In some embodiments, the additional agent is an anti-viral agent, such as a viral entry inhibitor, a viral uncoating inhibitor, an agent that inhibits release of viruses from cells, an agent that interferes with post-translational protein modification or with viral protein targeting, or with viral maturation, an antisense compound that is complementary to critical sections of the viral genome, and the like. Exemplary anti-viral compounds include, but are not limited to, acyclovir, vidarabine, idoxuridine, brivudine, cytarabine, foscarnet, docosanol, formivirsen, tromantidine, imiquimod, podophyllotoxin, cidofovir, interferon alpha-2b, peginterferon alpha-2a, ribavirin, moroxydine, valacyclovir, trifluridine, and bromovinyldeoxyuridine. In other embodiments, the additional agent is a chemotherapeutic agent, such as an alkylating agent, an anti-metabolite, an anti-microtubule agent, a topoisomerase inhibitor, or a cytotoxic antibiotic.

In various embodiments, where viral infection leads to autoimmunity in a patient, a tolerizing strategy can be employed. Various tolerizing strategies can be found, for example, in U.S. patent application Ser. No. 13/871,730.

In one embodiment, a first therapeutic agent is administered concurrently with a second therapeutic agent as a single composition comprising an effective amount of the first therapeutic agent and an effective amount of the second therapeutic agent. Alternatively, a composition comprising an effective amount of a first therapeutic agent and a second composition comprising an effective amount of the second therapeutic agent are concurrently administered. In another embodiment, an effective amount of a first therapeutic agent is administered prior or subsequent to administration of an effective amount of the second therapeutic agent. In this embodiment, the first therapeutic agent is administered while the second therapeutic agent exerts its therapeutic effect, or the second therapeutic agent is administered while the first therapeutic agent exerts its therapeutic effect for treating disease.

An effective amount of the second therapeutic agent will be known to the art depending on the agent. However, it is well within the skilled artisan's purview to determine the second therapeutic agent's optimal effective-amount range. In some embodiments of the invention, where a second therapeutic agent is administered to a patient for treatment of a viral disease, the minimal effective amount of the compound will be less than its minimal effective amount would be where the second therapeutic agent is not administered. In this embodiment, the first therapeutic agent and the second therapeutic agent can act synergistically to treat or prevent a condition.

A composition of the invention is prepared by a method comprising admixing a therapeutic agent or a pharmaceutically acceptable derivative thereof with a pharmaceutically acceptable carrier or excipient. Admixing can be accomplished using methods known for admixing therapeutic agents and a pharmaceutically acceptable carrier or excipient. In one embodiment, the therapeutic agent is present in the composition in an effective amount.

5.6. Methods of Preventing Viral Disease

In another embodiment, the present invention relates to methods and compositions for preventing a viral disease in a subject. In certain embodiments, the viral disease is IPF. In other embodiments, the viral disease is a lymphoproliferative disease or cancer. In various embodiments, methods of preventing a viral disease comprise a step of immunizing a subject with an immunizing effective amount of an antigen. Accordingly, the present disclosure further relates to a vaccine composition for use in the disclosed methods. In certain embodiments, the antigen is an antigenic protein or peptide from a virus. In certain embodiments, the antigen is a protein or peptide from the envelope or capsid of the virus. In some embodiments, the antigen is selected from a virus envelope associated antigen, a virus latency-associated nuclear antigen, a virus cytoplasmic late antigen, a virus nuclear early antigen, and combinations thereof. In certain embodiments, the virus is Herpesvirus saimiri. In other embodiments, the virus is a related virus.

Accordingly, the present disclosure further relates to vaccine composition for use in the disclosed methods. In certain embodiments, the antigen is an antigenic protein or peptide from the virus. In certain embodiments, the antigen is a protein or peptide from the capsid of the virus. In some embodiments, the antigen is selected from a virus membrane associated antigen, a virus latency-associated nuclear antigen, a virus cytoplasmic late antigen, a virus nuclear early antigen, and combinations thereof. In certain embodiments, the virus is Herpesvirus saimiri. In other embodiments, the virus is a related virus.

A variety of methods can be used to produce antigenic material for inclusion in vaccine compositions. In certain embodiments, antigenic peptides can be synthesized based on the complete nucleic acid and/or amino acid sequence of the genome of the virus. In other embodiments, the viral genome can be used as a source of nucleic acids to be used with recombinant DNA techniques to generate cells that express proteins encoded by the viral nucleic acids apart from the rest of the viral genome. Alternatively, antigenic proteins or peptides can be isolated from viral particles grown in cell culture.

In various embodiments, the vaccine composition comprises an effective immunizing amount of a virus. In some embodiments, the virus is a live attenuated whole virus. In other embodiments, the virus is an inactivated virus. In particular embodiments, the live whole virus comprises an inactivating mutation in the genome, e.g., a deletion, substitution or insertion in an endogenous promoter region of an intermediate-early gene. In other particular embodiments, the live attenuated whole virus is incapable of establishing latent infection. In still other embodiments, the live vaccine is genetically engineered to lack viral persistence. See, e.g., Wu et al. (2010) Immunology Research 48:122-146. In other embodiments, the vaccine comprises recombinant bacteria that express viral antigens. See, e.g., Karem et al. (1997) J of Gen Virology 78:427-434. Other Herpesvirus vaccine applications and methods are disclosed, for example, in Burke et al. (1992) Current Topics in Microobiology and Immunology 179:137-158; Koelle et al. (2003) Clin Microbiol Rev 16:96-113; Johnston et al. (2011) J Clin Investigation 121:4600-4609.

In certain embodiments, a vaccine composition for immunization for Herpesvirus saimiri or a related virus can comprise one or more antigens from a virus other than Herpesvirus saimiri or a related virus, as inoculation against one Herpesvirus type has been found to protect against infection from other Herpesvirus types. See, e.g., Goaster et al., in "Open Access Journal of Clinical Trials" (reporting that inoculation with a vaccine against varicella zoster also provided benefits to patients with HSV1 and HSV2 infections). Accordingly, in certain embodiments, the vaccine composition is selected from Zostavax® (Merck), Varivax® (Merck), GEN-003 (Genocea Biosciences) and ACAM529 (Sanofi Pasteur).

In certain embodiments, a healthy subject is inoculated. In other embodiments, a subject who has a viral infection is inoculated. In other embodiments, a subject who does not have a viral infection, but who has one or more potential risk factors for viral infection is inoculated. In still other embodiments, the subject to be inoculated is developing or has developed a viral disease. In certain embodiments, the subject is asymptomatic. In other embodiments where the vaccine is for Herpesvirus saimiri, the subject to be inoculated is suffering from interstitial lung disease. In yet other embodiments where the vaccine is for Herpesvirus saimiri, the subject to be inoculatd evidences a usual interstitial pneumonia pattern on high-resolution computed tomography (HRCT).

Administration of the vaccine compositions described herein can be as a single immunizing effective dose or as a divided immunizing effective dose. In one embodiment, an immunizing effective dose is administered once per month. In another embodiment, the immunizing effective dose is administered once per year, twice per year, three times per year or more. In other embodiments, the immunizing effective dose is administered once every two years, once every three years, once every four years or more. In certain embodiments, the vaccine compositions can be administered in a single immunizing effective dose with booster inoculations after, e.g., 1 week, 2 weeks, 1 month, 3 months, 6 months or one year or more as needed after the initial inoculation. The skilled artisan will recognize that the vaccination schedule is dependent on many factors, including the amount of anti-viral antibodies present in the blood of the subject after initial inoculation, the weight and physical condition of the subject, and the presence of infection and its severity, among other things.

Immunization procedures may be carried out by any method known in the art, including but not limited to, intravenous, intramuscular, intraperitoneal, nasal and/or oral administration. The vaccine compositions described herein can include one or more additional agents selected from an adjuvant, a preservative, a diluent, a stabilizer, a buffer, a solvent, an inactivating agent, a viral inactivator, an antimicrobial, a tonicity agent, a surfactant, a thickening agent and combinations thereof. Adjuvants that enhance immunogenic reactions include, but are not limited to, aluminum phosphate, aluminum hydroxide, squalene, an extract of *Quillaja saponaria*, MF59, QS21, Malp2, incomplete Freund's adjuvant, complete Freund's adjuvant, Alhydrogel®, 3 De-O-acylated monophosphoryl lipid A (3D-MPL), Matrix-M™ (Isconova) and combinations thereof. Other agents that can be included in vaccine compositions can be found, for example, at http://www.vvaccinesafety.edu/components-Excipients.htm.

5.7. Isolation of Disease-Causing Herpesvirus Sequences

As disclosed in Examples 1 and 2, below, high levels of signal were obtained using various probes derived from Herpesvirus saimiri that were modified with Locked Nucleic Acid (LNA) monomers. Probes comprising LNA monomers form very stable hybrids with target nucleic acids with the result that probes that are not completely complementary to the viral genome may still be able to identify the presence of herpesvirus nucleic acids if there is sufficient homology. Accordingly, there is a possibility that the herpesvirus present in the IPF specimens assayed in Examples 1 and 2 is a variant of Herpesvirus saimiri having mutations and/or alterations in the genome that confer on the virus the ability to grow in humans. Furthermore, there is a possibility that the Herpesvirus present in IPF patients is not Herpesvirus saimiri itself, but is an undescribed but related gamma herpesvirus that shares extensive homology with Herpesvirus saimiri.

To gather further information regarding the viral infectious agent in IPF, tissue samples were tested with probes using unmodified nucleotides rather than LNA nucleotides to insure that any positive results for the presence of the virus were dictated by the complementarity of the probe and not by affinity enhancing modifications such as LNA. As described in Example 9, below, larger probes composed of normal bases were made by creating clones that contained the Herpesvirus saimiri sequences for the polymerase gene (1,826 nucleotides; SEQ ID NO: 11), the Terminal Repeat region (1,383 nucleotides; SEQ ID NO: 12), the IL-17 gene (853 nucleotides; SEQ ID NO: 13) and the STP gene (1,232 nucleotides; SEQ ID NO: 14). Plasmid DNA from these clones was nick-translated and labeled with biotin-labeled dUTP ("biotin-labeled probes") and hybridized under the same conditions as the LNA probes in the experiments described in Examples 1 and 2. See Example 10, below. As seen in FIG. 10, the larger unmodified probes gave substantially the same results as the LNA probes in Examples 1 and 2. Specifically, the biotin-labeled probes showed strong hybridization to epithelial cells in IPF samples. Accordingly, in situ hybridization with LNA probes as reported in Examples 1 and 2 and with the biotin-labeled probes as reported in Example 10 demonstrate that both types of probes target viral sequences present in IPF samples.

Nevertheless, these experiments do not clearly establish whether there is total or partial homology between the Herpesvirus saimiri derived probes and the target sequences in IPF samples. To establish the degree of homology of the probes with target sequences in the IPF samples, hybridizations were carried out with a pool of the four biotin-labeled probes described above (SEQ ID NOs: 11-14) followed by washing with varying degrees of stringency. For comparison, the digoxigenin labeled LNA STP probes from Example 1 were also used with high stringency (50° C.) washes. As described in Example 11, three different washing conditions were used for the biotin-labeled probes, "high stringency" with 0.1×SSC at 50° C.; "low stringency" with 0.1×SSC at 4° C. and "very low stringency" with 1×SSC at 4° C. The results of these experiments are shown in Table 3. When the biotin-labeled probes were used, three specimens (137431, 7480 and 71706) showed a difference in hybridization in only one level between low stringency and very high stringency, and two samples (994326 and 205601) showed a difference in hybridization in two levels—3/0 to 1/0 for 994326 and 2/0 to 0/0 for 205601—indicating a possibility that there are sequence differences between the biotin-labeled probes and the herpesvirus sequences in the IPF samples. In contrast, the LNA probes continued to show high signal levels for all of the tested IPF samples, even after a high stringency wash. In addition to the IPF specimens, some of the other diseases that have now been shown to be associated with Herpesvirus saimiri were also tested in the same manner as described in Example 12. The results are shown in Table 3. Interestingly, a consistent loss of signal was observed when using the biotin-labeled probes under high stringency conditions as compared to low stringency conditions. This result may indicate that the clinical samples are not infected by Herpesvirus saimiri, but by one or more novel viruses.

It should be pointed out that, even considering the results indicating that there is not a perfect match between Herpesvirus saimiri sequences and the target sequences in the clinical samples, Herpesvirus probes can be used under proper hybridization and washing conditions to efficiently bind to related gammavirus sequences in clinical specimens. More sensitive detection may be developed by examining the Herpesvirus sequences in IPF and other diseases that generate signals with Herpesvirus saimiri probes. Once these sequences are determined, assays can be further optimized by redesigning probes such that they are more highly complementary to viral sequences in the clinical samples. The use of optimized probes will allow for the detection of viral sequences in clinical specimens using more stringent hybridization and washing conditions, thereby potentially reducing background signal from non-target sequences. The present invention allows such optimized probes to be designed according to the experimental results described herein relating to the reactivity of Herpesvirus saimiri probes. These results allow a 'tag' to be used for screening clones from a library of nucleic acids made from infected cells. The principle that limited homology between viruses can be used as a marker for isolating novel viruses from clinical samples is well established, as it has been done to identify and clone human papilloma viruses. Specifically, numerous types of HPV were identified and cloned using a "leapfrog" technique with a probe designed for a known HPV type used to isolate novel but related family members. For instance, HPV6b was used to identify HPV11 at low stringency in a phage library (Gissman et al., 1982 J Virol 44; 393); labeled HPV11 was then later used to isolate a clone of HPV16 (Durst et al., 1983 Proc Nat Acd Sci (USA) 80; 3812-3815) and in turn, low stringency probing with labeled HPV16 allowed isolation of a clone of HPV33 (Beaudenon et al., 1986 Nature 321 246-249). In a similar fashion, the clone for HPV18 was identified and isolated using a mixture of HPVs 8, 9, 10 and 11 (Boshart et al., 1984 EMBO Journal 3; 1151-1157), and a pool of HPV types were used to isolate HPV31 (Lorincz et al., 1986 J Virol 58; 225-229) and HPV51 (Nuovo et al., 1988 J Virol 62; 1452-55). In addition, limited homology can also be used on a microscale where certain segments of a virus tend to be more conserved. Thus again using the example of HPV, after information on a number of sequences of various types had accumulated, consensus primers were developed that could amplify a large variety of different HPV types by PCR. The consensus primers that have been used most frequently to identify other HPVs are the MY09/MY10 pair (Manos et al., 1989 Cancer Cells 7; 209-214) and the GP5+/GP6+ pair (Husman et al., 1995 J Gen Virol 76; 1057-1062), which are both derived from conserved sequences in the HPV L1 gene.

The knowledge that there is a herpesvirus in IPF that has homology with various DNA probes derived from Herpesvirus saimiri allows for isolation of all or a portion of the genomes of the virus that is present in patients using various known methods. For instance, similar to what has been described for HPV, primer sets have been described that are sufficiently generic that they can amplify a number of novel gamma herpesviruses from tissue samples from a variety of organisms by taking advantage of a relative conservatism in the DNA polymerase, glycoprotein B and/or terminase genes among various members of the gamma herpesvirus family. (Chmielewicz, et al., 2001 Virus Research 75; 87-94; Ehlers et al., 2007 J Virol 81; 8091-8100; Ehlers et al., 2008 J Virol 282; 3509-3516). Animals that were successfully used to obtain sequences of new gammaviruses were phylogenetically very disparate and included representatives of Primates (gorilla), Artiodactyla (chamois and pigmy hippopotamus), Perissodactyls (zebra and tapir), Proboscidea (Asian elephant) and carnivores (lion and spotted hyena). Not surprisingly, the viral sequences between the generic primers echoed the phylogentic distances between the hosts. (Ehlers et al., 2008). Consequently, in one embodiment, these primer sets can be used to obtain sequences from clinical samples that are suitable for identification of the phylogenetic relationship of the gamma herpesvirus in IPF patients to the known sequence of Herpesvirus saimiri, where the patient-derived viral sequence is a) identical to Herpesvirus saimiri, b) essentially the same as Herpesvirus saimiri with some sequence variation or c) a novel virus related to Herpesvirus saimiri sufficiently similar such that probes derived from Herpesvirus saimiri can display stable probe binding in clinical samples. The connectivity of the IPF pathogen to sequences that are more distant from the Herpesvirus saimiri genome can then be validated using these new sequences to make labeled probes that can be reapplied to clinical specimens previously showing positivity with the Herpesvirus saimiri probes.

In some embodiments, semi-generic primers are used to isolate the infecting gamma herpesvirus. In this approach, recognition of the similarity between Herpesvirus saimiri and the herpesvirus resident in IPF patients implies that it is unlikely to be a distantly-related gamma herpesvirus. As such, instead of using primers that are designed to amplify any and all gammaviruses, a more selective approach can be used by aligning the sequences of, for example, the polymerase genes in gammaviruses that are phylogenetically close and designing primers that will amplify all polymerase genes in the subgroup. In theory, this approach is more selective and more efficient because primers designed using this approach will have fewer mismatches with the infecting pathogen that a pan-gammavirus primer set.

In other embodiments, subtractive hybridization is used to eliminate much of the chromosomal DNA or RNA that is present in a nucleic acid preparation made from a clinical specimen from an IPF patient. A brief review of this method for isolation of novel viruses is set forth in Muerhoff et al. (1997) J Med Virol 53: 96-103. An example of this technique as applied to HVS is described in Knappe et al. (2000) J Vir 74:3881-3887 where cDNA fragments were searched for genes expressed in HVS-transformed lymphocytes but not in untransformed cells. The power of the method can be seen in that, among 399 sequenced clones, 280 were viral DNA clones and 119 were cellular cDNA clones. In this particular instance, Knappe et al. were focused on the nature and identity of the cellular cDNA clones, but the fact that they achieved such a high number of viral clones from the HVS-infected transformants as a byproduct implies that similar results can be achieved when using IPF and normal cells instead of infected and uninfected lymphocytes.

In yet other embodiments, positive selection is used to isolate a virus. For example, LNA probes that were used against the TER and STP regions of Herpesvirus saimiri were discovered to be specific and able to bind efficiently to the viral sequences present in IPF patients, as shown in Examples 1 and 2. As such, the same LNA sequences used with digoxigenin labels can be sythesized with a biotin label at a terminus and, after hybridization with IPF DNA (STP Or TER) or mRNA (STP), bound nucleic acids can be obtained with either a streptavidin column or streptavidin beads. The captured nucleic acids can then be used as a library of clones to be probed with LNA probes or other Herpesvirus saimiri sequences. A similar approach can also be taken with LNA probes that are designed for other genome segments.

In various embodiments, classic shotgun cloning of a library of either DNA or cDNA from IPF patients and screening of clones using probes derived from either a portion or the entire genome of Herpesvirus saimiri can be used to isolate the infecting virus. This method provides no bias either for or against clones and identification is strictly due to the presence of homology with Herpesvirus saimiri. Since there is a large amount of chromosomal DNA in any virus-infected cell, a sequence-independent enrichment process can used to increase the portion of viral DNA as compared to host DNA. In certain embodiments, enrichment can be accomplished using a Hirt procedure (Hirt (1967) J Mol Biol 26:365-369) that selectively allows episomal DNA to remain in solution while most of the chromosomal DNA is precipitated with detergent. This method has been successful when used with herpesviruses, even though the viral genome is large (130-150 kb) (Pater et al. (1976) Virology 75; 481-483; Rosenthal et al. (1983) Intervirology 19; 113-120; Eizuru et al. (1984) J Clin Microbiol 20; 1012-1014). Other techniques for sequence-independent enrichment include separation of viral-protein complexes (Pignatti et al. (1979) Virology 93; 260-264) and isolation of viral particles (Kintner and Brandt (1994) J Vir Methods 189-196). Low stringency hybridization with HVS probes should allow identification and isolation of clones with homology with HVS that have been linked to the various diseases previously described. Sequencing of these probes should clarify the relationship of the herpesvirus in the clinical samples with the Herpesvirus saimiri sequence.

5.8. Mouse Model of IPF

In certain embodiments, the various methods described herein can be carried out using an animal model of disease in lieu of, or in addition to, patient samples. Accordingly, in some embodiments the various methods described herein can be carried out using a mouse model, such as the mouse model described by Pierce et al. (2007) Am J Pathology 170:1152-1164. This mouse model is achieved by intravenously injecting human primary fibroblasts from IPF patient lung biopsies into Severe Combined Immunodifficient ("SCID") mice. The human cells migrate to the lungs and cause patchy interstitial fibrosis upon examination at 35 and 63 days after injection. In contrast, fibroblasts from normal donors do not induce fibrotic change in lung structure when injected into SCID mice. This mouse model has been used to investigate the roles of CC ligand 21 and CCR7 (Pierce et al. 2007) and the TL9 receptor (Trujillo et al. (2010) Sci Transl Med 2(57): 57ra82) in pulmonary fibrosis, as well as the exacerbation of fibrosis by CpG-oligodeoxynucleotide (Hogaboam et al. (2012) Fibrinogen & Tissue Repair 5(Suppl. 1):S3). Furthermore, transfer of fibroblasts from IPF patients to a SCID mouse host should also convey the Herpesvirus causative agent of IPF.

Although the SCID mouse model of IPF does not totally recapitulate the disease, the observation that human primary fibroblasts from IPF patients colonize the mouse lung and are associated with development of fibrotic lung tissue offers an easily manipulated and inexpensive system for further research into disease markers, compositions for detection of disease, and identification of therapeutic agents. Accordingly, in some embodiments, the SCID mouse model is used to identify and optimize probes and primers for detection of viral nucleic acids and/or amplification of nucleic acids from patient samples. In one particular embodiment, original cells taken from a human patient after fibrosis has been established are expanded in vivo, and the mouse lungs are used as a source of tissues for examination of Herpesvirus sequences, either by in situ hybridization and/or by extraction of nucleic acids from the cells and tissues. In various embodiments, markers of human cells are used to distinguish between mouse cells and human cells in order to determine if viral sequences and/or viral protein expression are transferred from the transplanted patient cells to the cells of the murine host. In various embodiments, the extracted nucleic acids are used for isolation and amplification of viral nucleic acid sequences by any means previously described.

In various embodiments, the SCID mouse model of IPF is used for detecting the presence of various disease markers of IPF that are not readily assayed in a human patient. In certain embodiments, the mouse model is utilized for detecting IPF markers not only in lung tissues or bronchiolar lavage, but also in blood or other tissues that are more easily collected from a human patient than lung tissue. In various embodiments, the mouse model is used for identifying disease-driven physiological changes in tissues that are not normally associated with IPF, or detecting disease-driven physiological changes associated with a particular stage of the disease, or associated with rapidly progressing disease versus slowly progressing disease.

The collection of human lung samples by needle biopsy is invasive and presents many risks, including lung collapse, respiratory failure and bleeding, which are more common in patients ages 60 to 69 (IPF usually presents in adults over 50 years of age), smokers, and patients with chronic obstructive pulmonary disease (COPD). See Soylemez Weiner et al. (2011) Annals of Internal Medicine 155(3):137-144. Accordingly, in still other embodiments, the SCID mouse model is used in assays that require a negative control in lieu of a lung biopsy from a human subject that does not have IPF. In these embodiments, the IPF mouse model is the positive control and a non-infected SCID mouse is the negative control.

In still other embodiments, the SCID mouse model is used to identify therapeutic agents for the treatment of IPF, such as those described in Section 6.5, above. In particular embodiments, by virtue of its inability to make antibodies, the SCID mouse model is used to determine the efficacy of therapeutic antibodies, such as antibodies to viral gene products whose expression is correlated with IPF. Accordingly, in some embodiments, the SCID mouse model is used to determine the therapeutic efficacy of a viral IL-17 antibody, a viral IL-10 antibody or a viral latency-associated nuclear antigen antibody. In other embodiments the mouse model is used to determine the therapeutic efficacy of an antibody selected from an anti-TGF-β antibody, an anti-IL-23 antibody, and an anti-IL-1β antibody. In still other embodiments, the mouse model is used to determine the therapeutic efficacy of an antibody selected from an anti-DHFR antibody, an anti-cyclin D antibody, and an anti-thymidylate synthase antibody. Furthermore, although the identification and evaluation of therapeutic agents that target viral replication and/or propagation can be carried out in virus infected human cell culture, the ability to administer such agents in an in vivo model of disease should generate results that have a likelier chance of success when positive candidates are later tested in humans.

6. EXAMPLES

This section describes the various different working examples that will be used to highlight the features of the invention(s).

Example 1: Hybridization with LNA Oligonucleotide Probes from STP Region of Herpesvirus Saimiri Detection of Herpesvirus saimiri sequences in paraffin embedded formalin fixed samples from IPF patients was carried out by in situ hybridization with oligonucleotides probes according to methods described in Nuovo et al. (2010) Methods 52:307-315. Formalin fixed paraffin embedded tissue samples from 22 IPF patients in which sufficient tissue was available for molecular studies were obtained from archived files. The mean age of the patients was 56.6 years (SEM=2.5 years), 14 were men and 8 were women. Evaluation of the hematoxylin and eosin stains of these tissues confirmed the heterogeneous histologic findings of usual interstitial pneumonitis. In each IPF case, no etiology or underlying disease state could be identified for the patient's illness.

In brief, slides were pre-treated for 4 minutes with Proteinase K (Ventana Medical Systems) and then hybridization was carried out with a 5 femtomole/4, solution of labeled probes. The probes used for this process were LNA analogues with digoxigenin labels at their 5' ends (Exiqon) and were derived from the sequence of the Herpesvirus saimiri STP gene of the C488 strain of Herpesvirus saimiri (Albrecht et al. (1992) J Virology 66:5047-5058).

```
                                         (SEQ ID NO: 5)
    Oligo #1   5'-CTCTAAGCACAGGGGCACAG-3'

(SEQ ID NO: 6)
    Oligo #2   5'-CTACGCAGAAGTCGGAAGCC-3'
```

The oligonucleotides were used as labeled probes (SEQ ID NO: 5 and SEQ ID NO: 6). Their relative locations can be found using Genbank Accession #M28071 for the STP sequence. Probe/target complex was detected with alkaline phosphatase-anti-digoxigenin conjugate reacting with nitroblue tetrazolium and bromochloroindolyl phosphate (NBT/BCIP) forming an insoluble blue precipitate. Negative cells were counterstained with nuclear fast red. Negative controls included the omission of probes, oligonucleotides with scrambled probe sequences and the use of specimens from non-IPF lung fibrosis patients. Hybridization and detection with these probes gave positive readings in the IPF samples as shown in FIG. 1A where intense cellular staining with the Herpesvirus saimiri DNA probes can be seen at the arrow indicator. For comparison, a lung cancer specimen is shown in FIG. 1B, indicating a lack of any staining with the Herpesvirus saimiri-specific labeled probes.

Example 2: Hybridization with LNA Oligonucleotides from STP and TER

In order to rule out the possibility of an artifact giving false positives, another set of digoxigenin-labeled LNA probes (SEQ ID NO: 7; SEQ ID NO: 8) were designed to specifically bind to a different portion of the Herpesvirus saimiri genome, the 1,444 nucleotide Terminal Repeat (TER) sequence of C488 (Bankier et al. (1985) J Virology 55:133-139).

```
Oligo #3   5'-GCCGCCTCAGAATTTTAGCA-3'   (SEQ ID NO: 7)

Oligo #4   5'-CTCTGCGTGAAGCACAGTGC-3'   (SEQ ID NO: 8)
```

These oligonucleotides were used as labeled probes. Their relative locations can be found using Genbank Accession # K03361 for the reference sequence. In FIG. 2, two serial sections of a specimen were tested with the STP pair (SEQ ID NO:5 and SEQ ID NO:6, FIG. 2A) or the TER pair (SEQ ID NO:7 and SEQ ID NO:8, FIG. 2B). Hybridization was accomplished with both sets of labeled probes and the signal from each set was generated in the same areas of the biopsy section, confirming that these are areas of viral infection. As a further control, other mix and match experiments were carried out using serial sections with the STP or TER probe sets in individual hybridization reactions, and 5 out of 5 specimens were positive for each set (data not shown). In another variation, either the (+) strand STP probe or the (−) strand STP probe was individually used, and 5 out of 5 specimens gave the same results (data not shown).

Twenty-two IPF samples were tested, and all specimens scored positive for Herpesvirus saimiri DNA. A number of pulmonary samples from non-IPF patients were tested as negative controls. These specimens included 7 cases of scar adenocarcinoma of the lung, 9 cases of lung fibrosis associated with emphysema and 9 cases of nonspecific interstitial pneumonia (NSIP) associated with known viral infection, including measles (1 case), adenovirus (3 cases), hantavirus (3 cases) and rotavirus (2 cases). All 25 of these non-IPF specimens were negative for hybridization of the Herpesvirus saimiri probes, demonstrating a strong negative correlation. The majority of the cases were also tested using biotinylated DNA probes (Enzo Biochem) for other viruses, including Epstein-Barr Virus (EBV) cytomegalovirus (CMV) and Herpes simplex virus types I and II (HSV-I/II) and all were negative for the presence of these viruses.

The Herpesvirus saimiri DNA distribution closely paralleled the histopathology of IPF (FIG. 3A-3C). Herpesvirus saimiri nucleic acids were evident in the regenerating epithelial cells in the areas of active IPF (FIGS. 3D, 3G and 3H). Rare viral DNA-positive pneumocytes were seen in the histologically unremarkable areas of the IPF lung sections (FIG. 3E) and various positive cells were not in evidence in the areas of end-stage fibrosis of IPF which lacked epithelial cells (data not shown), or in the regenerating epithelial cells of interstitial pneumonitis of known etiology (FIG. 3F). Although scattered interstitial cells with the cytological appearance of macrophages as well as rare endothelial cells were positive for viral DNA, over 95% of the cells positive for viral DNA were regenerating epithelial cells.

Example 3: Detection of IL-17

The discovery that there is active infection by Herpesvirus saimiri in epithelial cells of IPF patients offers an explanation for the results of earlier nucleic acid and proteins studies showing insignificant changes in the amount of IL-17 in IPF patients, which contrasted to the results of Nuovo et al. (2012), which showed high levels of expression of IL-17 in IPF specimens in replicating epithelial cells, a type of cell unassociated with IL-17 expression. This paradox can now be resolved in that previous microarray, protein array and ELISA results did not show evidence of any profound changes in human IL-17 whereas the Nuovo et al. (2012) results are a result of detection of viral IL-17 coded by Herpesvirus saimiri.

FIG. 4 shows comparisons of the human and viral sequences for IL-17 for both the protein (FIG. 4A) and nucleic acid (FIG. 4B) sequences. The protein sequence comparison (FIG. 4A) shows that there are a number of epitopes that appear in only the human version of IL-17 (SEQ ID NO:1). Accordingly, if previous antibody studies used a monoclonal antibody (as in ELISA and protein arrays) specific for one of these human epitopes, the viral form of IL-17 (SEQ ID NO:2) would not have been detected by the antibody. The same is true for the nucleic acid comparison, where there are numerous segments that, if used as microarray elements, would be complementary to only the human version of IL-17 (SEQ ID NO:3). With regard to this point, when microarrays are designed, the usual criteria for the choice of sequences for capture elements is a lack of identity with other similar sequences. Consequently, in the microarray studies of nucleic acids in IPF patients, measurements of human IL-17 nucleic acids would have been investigated, but no probes to the viral IL-17 nucleic acids were likely used in these studies. On the other hand, Nuovo used polyclonal antibodies, which likely recognized multiple epitopes in the viral IL-17 that are shared by both human and viral proteins, and therefore, would be recognized by the polyclonal antibodies. The presence of conserved segments that comprise identical sequences can be seen in the comparison of FIG. 4. As such, viral expression of IL-17 in the cells of IPF patient specimens was detected by Nuovo by use of the polyclonal antibodies.

Example 4: Immunohistochemistry of Viral Proteins in IPF and Non-IPF Lung Tissue As noted above for IL-17, one of the properties of the gammaherpesvirus family is the "adoption" or "pirating" of host genes into the viral genome. Consequently, given that Herpesvirus saimiri DNA was detected in IPF samples and that the results with an anti-IL-17 polyclonal antibody were interpreted as detection of virally encoded IL-17, other viral homologues coded by Herpesvirus saimiri should also be detectable in the IPF specimens. Accordingly, histochemical analysis was carried out as described in Nuovo et al. (2010) Methods 52:307-315 using polyclonal antibodies to dihydrofolate reductase (DHFR), thymidine synthase (TS) and cyclin D1. Relative amino acid identities with the human equivalents are respectively 83%, 66% and 25% (Reviewed in Fickenscher and Fleckenstein (2001) Phil Trans R Soc Lond B Biol Sci. 356(1408):545-67). The similarity between the viral and human genes should be sufficient for some shared epitopes in the viral proteins to be recognized by polyclonal antibodies against the human gene products.

In brief, the automated Benchmark LT immunohistochemistry system was used with primary antibodies from ABCAM. An equal number of controls were also tested for each of these proteins using immunohistochemistry. Tissue specimens from this study are shown in FIG. 5. FIG. 5A-5C show the histologic distribution of cyclin D1 in IPF as determined by immunohistochemistry (signal fast red with hematoxylin counterstain). FIG. 5A shows that protein was expressed in the majority of regenerating epithelial cells in the areas of active fibrosis (FIG. 5A, 100×) and, like the viral DNA, in rare alveolar lining cells in the histologically normal areas in the IPF lung (FIG. 5B, 400×). At higher magnification in the active fibrosis areas the strong signal for cyclin D1 was found exclusively in the regenerating epithelial cells (FIG. 5C, 400×). Another viral homologue, dihydrofolate reductase (FIG. 5D, 100×) shows the same topographic pattern as cyclin D1 and viral DNA and, similarly, shows rare positive alveolar lining cells in the adjacent histologically normal lung (FIG. 5E, 400×). FIG. 5F shows a strong signal for thymidylate synthase in a region with marked interstitial fibrosis in IPF (400×, DAB signal, hematoxylin counterstain). Both dihydrofolate reductase and cyclin D1 are commonly found in the malignant epithelia of lung cancer (FIGS. 5G and 5H, respectively, each at 200× with fast red signal and hematoxylin counterstain-large arrows). However, unlike the IPF samples, these proteins were not evident in the subjoining areas of the lung that showed active fibrosis and regenerating serpentine glands (small arrows).

Example 5: Histochemical Testing for Non-HVS Viruses

Immunohistochemical analyses were carried out by probing for the latent membrane protein (LMP) of EBV, the latent nuclear antigen (LNA-1) of KSHV, and CMV proteins 8B1.2, 1G5.2, and 2D4.2, respectively representing immediate early, early, and late antigens of CMV. No viruses were detected by these methods. (Data not shown)

Example 6: Co-Localization of HVS DNA and Protein Targets

To show that there is a direct connection between the presence of Herpesvirus saimiri DNA and expression of viral homologues coded by the virus, experiments were carried out that simultaneously detected the presence of DNA and protein targets in the same specimen. Methods for this simultaneous detection have been described in Nuovo et al. (2009) Nature Protocols 4:107-115. Briefly, computer-based analysis by the Nuance system (Caliper) separates each chromogenic spectral signal, converts it to a fluorescent signal, then mixes the two and indicates if cells contain the two targets of interest.

Results for this analysis are shown in FIG. 6 and indicate that expression of IL-17, cyclin D and thymidylate synthase are directly correlated with the presence of Herpesvirus saimiri in the cells. Note especially that FIG. 6E-6H show the same groups of cell in subjacent serial sections.

Example 7: Detection of HVS in Patients with Castleman's Disease

Thirteen HIV-1 negative patients suffering from idiopathic Castleman's disease and 13 control patients (which included tissues from benign lymph nodes, and four patients with various neoplastic diseases including Burkitt's lymphoma, oral hairy leukoplakia and other diseases) were tested for the presence of Herpesvirus saimiri. Of the Castleman's disease patients examined, 9 were men and 4 were women, and the mean age was 45.5 years. Lymphoproliferative Castleman's tumors ranged from 3.2 cm to 8.5 cm (mean 6.0 cm) and 12 of the tumors were mediastinal or retroperitoneal. Three cases were multicentric and 10 were unicentric.

All patients and control patients were tested for the presence of HVS DNA in formalin fixed paraffin embedded tissue samples using in situ hybridization with STP probes (SEQ ID NO: 5 and SEQ ID NO: 6 in Example 1). Five cases were tested with TER probes (SEQ ID NO: 7 and SEQ ID NO: 8 in Example 2), and all cases were tested with probes directed against two of the major Herpesvirus saimiri specific U rich noncoding region small RNA molecules (Cazalla et al. (2010) Science 328:1563-66) and having the sequences:

```
                                    (SEQ ID NO: 9)
Oligo #5    5'-TATTTACACCCAGTACCTACAAAAATT-3'

(SEQ ID NO: 10)
Oligo #6    5'-TAAATAAATATGTAGTGT-3'
```

These probes were also LNA modified and 5' tagged with digoxigenin.

Using in situ analysis, patient tissues were further characterized by screening for expression of cyclin D and IL-17.

As set forth in Table 1, below, all 13 of the Castleman's disease patients were positive for HVS DNA using the STP and U rich noncoding region small RNA probes, whereas normally, only 4-7% of adult humans are positive for HVS DNA. In addition, as set forth in Table 2, below, 0 of 13 control patients were positive for HVS DNA. Viral nucleic acids were localized in patients to the majority of B-cells in the expanded germinal centers/mantle zone that is typical of Castleman's disease, while the interfollicular zone ("T cell zone") was negative for virus. See FIG. 7A-7B, 7H. Identification of infected cells as B-cells was confirmed by the presence of CD20 on the cells. FIG. 7C. Viral infection was non-lytic based on the low percentage of HVS+ cells expressing viral IL-17. See FIG. 7D. T-cells were localized primarily to the zone between the expanded germinal centers/hyperplastic mantle zone and had high IL-6 expression induced by infected B-cells. See FIG. 7E-7F. Infected B-cells were found to be negative for both CD3 and IL-6, FIG. 7G. Most B-cells in tissues of Castleman's patients are positive for Herpesvirus saimiri U-rich noncoding RNA which is indicative of a latent infection. Thus, idiopathic Castleman's disease (unicentric and multicentric forms) is associated with a massive, non-lytic HVS infection of B-cells that induces IL-6 production in adjacent T-cells. HVS proteins were not abundant in the affected tissues of Castleman's disease patients.

TABLE 1

Presence of Herpesvirus saimiri in 13/13 Castleman's disease patients

| Case | Herpesvirus saimiri STP probe | Herpesvirus saimiri URNA | Cyclin D1 | IL-17 |
|---|---|---|---|---|
| Castleman 1 | Positive 3+ | Positive 3+ | 1+ | 1+ |
| Castleman 2 | Positive 3+ | | 1+ | 1+ |
| Castleman 3 | Positive 3+ | Positive 3+ | 1+ | |
| Castleman 4 | Positive 3+ | | 1+ | 1+ |
| Castleman 5 | Positive 3+ | Positive 3+ | 1+ | 1+ |
| Castleman 6 | Positive 3+ | | 1+ | 1+ |
| Castleman 7 | Positive 3+ | Positive 3+ | 1+ | 1+ |
| Castleman 8 | Positive 3+ | Positive 3+ | 1+ | 1+ |
| Castleman 9 | Positive 3+ | Positive 3+ | 1+ | 1+ |
| Castleman 10 | Positive 3+ | | 1+ | 1+ |
| Castleman 11 | Positive 3+ | | 1+ | 1+ |
| Castleman 12 | Positive 3+ | Positive 3+ | | 1+ |
| Castleman 13 | Positive 3+ | Positive 3+ | 1+ | |

TABLE 2

Control Subjects 0/13 for Herpesvirus saimiri

| Case | Herpesvirus saimiri STP probe | Herpesvirus saimiri URNA | Cyclin D1 | IL-17 |
|---|---|---|---|---|
| Burkitt's lymphoma | Negative | Negative | Endothelial | 0 |
| Oral hairy leukoplakia | Negative | | 0 | 0 |
| AIDS-related DLBCL | Negative | Negative | | |
| HHV8+ Castleman's | Negative | | 0 | 0 |
| Lymph node benign | Negative | Negative | Endothelial | 0 |
| Tonsil benign | Negative | Negative | 0 | 0 |
| Spleen benign | Negative | | Endothelial | 0 |
| Lymph node benign | Negative | Negative | Endothelial | 0 |
| Lymph node benign | Negative | Negative | 0 | 1+ |
| Lymph node benign | Negative | Negative | Endothelial | 0 |
| Lymph node benign | Negative | Negative | — | 1+ |
| Lymph node benign | Negative | Negative | Endothelial | 0 |
| Lymph node benign | Negative | Negative | Endothelial | 0 |

Example 8: Detection of HVS in Patients with Cancer

All testing described in this example was done using formalin fixed paraffin embedded tissue samples using in situ hybridization. Testing of 4 mediastinal, 2 retroperitoneal, 8 head/neck and 4 pericolic B-cell lymphoma tissues revealed that HVS DNA was present in 6 out of 12 mediastinal and retroperitoneal lymphoma samples, but was not present in any of the other 12 B-cell lymphomas (head/neck and pericolic). Forty-six thymomas were analyzed for HVS using STP and U-RNA probes. Twenty-three of 46 thymoma samples (50%) were positive for HVS DNA, while 0/19 samples of normal thymus tissues were positive for HVS DNA. Two thymoma samples from different patients that are HVS+ are shown in FIG. 8A-8B.

Analysis of other markers showed that 29/46 (63%) of thymoma samples were positive for CD20, 29/46 (63%) of thymoma samples were positive for IL-17 (FIG. 8B) (whereas 5/15 (33%) of normal thymus samples were positive for IL-17), 34/46 (73%) of thymoma samples were positive for cyclin D (FIG. 8C) (whereas 6/15 (40%) of normal thymus samples were positive for cyclin D), and 43/46 (93%) of thymoma samples were positive for keratin.

As shown in FIG. 8C-8D, relatively few thymoma cells tested positive for viral IL-17 or viral cyclin D1.

Two retroperitoneal liposarcomas were analyzed for HVS DNA using STP probes (SEQ ID NO: 5 and SEQ ID NO: 6 in Example 1) and TER probes (SEQ ID NO: 7 and SEQ ID NO: 8 in Example 2), and both were positive for the virus. (FIG. 9A-9B) As shown in FIG. 9A, in one sample, HVS+ cells had localization of signal in the nucleus, which is typical of herpesvirus infections in general. In addition, eighteen gastrointestinal stromal sarcoma samples were tested using STP probes (SEQ ID NO: 5 and SEQ ID NO: 6 in Example 1) and TER probes (SEQ ID NO: 7 and SEQ ID NO: 8 in Example 2) and 2 samples (not retroperitoneal) were positive for HVS DNA. (FIG. 9A-9B) Finally, 16 sarcomas that were not retroperitoneal or mediastinal (leiomyosarcoma, antiosarcoma, chondrosarcoma, and synovial sarcoma) were tested for the presence of HVS using STP probes (SEQ ID NO: 5 and SEQ ID NO: 6 in Example 1) and TER probes (SEQ ID NO: 7 and SEQ ID NO: 8 in Example 2), and were found to be HVS negative.

Example 9: Design and Synthesis of Biotinylated Probes for Herpesvirus Saimiri Viral DNA sequences were synthesized to make probes for hybridizing to IPF patient samples. The polymerase gene, terminal repeats, viral IL-17 gene and viral StpA gene of Herpesvirus saimiri were synthesized by Genscript, and inserted into the cloning vector pUC57 (http://www.genscript.com/vector/SD1176-pUC57_plasmid_DNA.html).

The polymerase probe (GenBank: AJ410493.1) has the sequence:

(SEQ ID NO: 11)
GAATTCCAAACAGACATAATACCTAATGGAACAGTGTTGA

AACTACTTGGAAGAACACTAGAGGGTGCGAGCGTATGTGTTAACG

TGTTTGGACAAAGAAATTACTTTTATGTTAAAGTTCCGGAAGGTG

GCAACATAACCTATCTTATGAAACAAGCTTTGAATGAAAAATTTA

GCCCATCTTGTGCATACCAAACTGAAGCAGTAAAAAAGAAGATAC

TATCTAGATATGATCCAAAAGAACATGATGTTTTTAAAGTGACAG

TGTCTTCTTCTCTTTCTGTTTATAAAATATCAGATTCTTTAGTGT

CTAATGGTTGTGAAGTTTTTGAAACAAATGTAGATGCTATAAGAA

GATTTGTAATTGATAACAACTTCTCTACATTTGGTTGGTACACAT

GTAAGTCTGCATGTCCTCGAATCACAAATAGAGACTCTCATACTG

ACATTGAGTTTGACTGCGGGTACTATGACTTGGAATTTCATGCAG

ATAGAACAGAATGGCCACCTTACAACATAATGTCTTTTGATATAG

AATGTATAGGAGAAAAAGGATTTCCGTGTGCAAAAAATGAAGAAG

ATTTAATAATTCAGATTTCATGTGTGTTTTGGCACGCTGGGACGC

TTGATGCAACTAGAAATATGCTATTATCTTTAGGGACGTGCTCAG

CTGTTGAAAATACTGAAGTTTATGAGTTTCCCAGTGAAATAGACA

TGCTGCATGGGTTTTTTTCATTAATTAGAGACTTTAATGTTGAAA

TAATTACTGGTTATAATATTTCTAACTTTGACTTACCCTATCTAA

TTGATAGAGCTACTCAAATTTATAATATAAAGCTATCTGATTATT

CAAGAGTTAAAACAGGGTCTATTTTTCAAGTTCATACGCCAAAAG

ATACAGGAAAGGGGTTCATGAGATCTGTCTCTAAAATAAAAATTT

CAGGAATTATAGCAATTGACATGTACATTGTGTGCAAAGACAAAC

TCAGTCTGTCTAATTACAAGCTTGATACTGTTGCTAATCACTGCA

TTAGTGCAAAAAAAGAAGATGTGTCTTACAAAGATATCATGCCTC

TTTTTATGTCTGGACCTGAAGGCAGAGCTAAGATAGGACTATACT

GTGTAATAGATTCTGTTCTTGTGATGAAACTTTTGAAATTTTTTA

TGATTCATGTTGAAATTTCTGAGATAGCGAAACTGGCTAAAATCC

CCACGAGAAGAGTTCTTACAGATGGGCAACAAATAAGAGTTTTTT

CTTGTCTGCTTGCAGCAGCTCGTGCAGAAAACTATATACTGCCTG

TGTCAAATGATGTCAATGCGGATGGGTTTCAGGGAGCTACCGTCA

TAAACCCAATTCCTGGATTTTATAACAATGCTGTATTAGTAGTAG

ACTTTGCTAGCCTGTATCCTAGTATCATACAAGCTCATAATCTAT

GCTACTCCACTCTTATACCCCACCATGCTTTACACAACTACCCTC

ACTTAAAATCTAGTGACTATGAGACTTTTATGCTCAGTTCTGGAC

CTATACACTTTGTGAAAAAACACATTCAGACATCTCTTCTATCTA

GGCTTTTAACTGTGTGGCTTTCTAAGCGAAAGGCTATTAGGCAAA

AGCTTGCTGAATGTGAAGACCTAGACACTAAAACTATTCTAGATA

AACAGCAACTCGCTATTAAGGTAACCTGTAATGCTGTGTATGGGT

TTACAGGAGTTGCGTCAGGCTTGCTGCCATGCATAAGCATTGCAG

AGACCGTTACTCTCCAAGGCCGGACGATGCTAGAAAAATCAAAAA

TATTTATAGAAGCAATGACACCTGATACACTTCAAGAGGATCC

The restriction enzyme sites for EcoRI and BamHI (underlined) were added to either end of the DNA sequence for easier manipulation.

The terminal repeat probe (GenBank: K03361.1) has the sequence:

(SEQ ID NO: 12)
GAATTCGGTCCGGAGCGGTCTCTACAGACGCCCCAGACTC

TCAGCTGTCCCCCGGTGCCGGCGCGGCGCCGCTGCCCCCCGCGGC

TGGGGAGCTAGGGCCGCTCAAAGCGGGTCCCCTCCCCCGGCCGCC

TGGGGATCTGCTAGGCAGCTGCTCTGCAGCCCAGCCTAGGGGCT

TCAGCGGGGCATAGCTCCACAGCGCAAGGGTCCCCGGGCTTCACA

CTCGGTGGGCAGGCAAGGGACCCTTCCCGCTGACGGCTGCAAACT

CTGGCTAGCCGGGGAACTCTGTGCTGGAGAGATAGGGGCGCGCA

AGCCCCCATCACAGGGCTCCGGCTGGCAGGGCTCGCCCTCAGGGC

TGCACAGCAGTCTAGCCTAGGGGCTTCAGCCAGGGCTAGCTCCA

AAACCCTCAGGTCCCCAGACTTCAAACTTGGTGGGCACGTAGAGG

ACCCTTCCCGCTGACTCTCCACGCCGCCTCAGAATTTTAGCACCC

GGCGCTGCGGAGCCGGGAGCCAGCAAGCCCCCCGCTGGGGTCTCG

GCTGCTGCTGCTCGGGGGCCTGGGGCTGGGGAGGCGGCTGCAGGG

GCTGCATGCACTGTGCTTCACGCAGAGGTCGGGGGGAGCCCAGC

```
TACGCGCCCCCCACGCTGCAGGGCGCTGCGCTGGGCTCTGGGGCT

GGGGGGGCTTGAACAGTTGTGGGACCCTTACTCTAGCAGCGCCTC

GGCCTAGCCAGGGCTCTGGGGACTGGCTCTAAGCACAGGGGCACA

GCGCCCCCGGGCCTGCGGTGGCCTGGGGACACAACAGGAGCTCTG

GAATCTCAGCCCAGAGGGGTGCGGGGCTGCTCAATCCCTTCCCCC

TCCCTCCGCAGCCGCTCGCTGCTCGCCCTGCCCCCCGAGCTCGCT

CTAGCCACGCCCAGGACATTTTTCCAGCTGCCCAGCGCCCACTGC

TTGGGGCCCCCCTTCCCCCTCTTTGCCTACCAAGTTATCCCCCGG

GGGGAAAATCAGTGGGGGCTGCATAGAGCTCTCCGCAGGCGGCCG

CTCGCTCCCCGGGCGTCCGCAGCCTCTCGGGGGGCCTCTGGGGCG

CCCGGCGGGAGCCCCCGTGCGGGGCTCCGGTCCCTCTAGTGCACA

AGCAGACTCTAGCCCCCTCCCCCAGTACACAGAGCCCAGCAGCCC

CCGGCCGCGGCGCCCGTGCAGCGCCCGGCAGCTTGCTTTCGGTTT

CTCGCCCCGAGACCCCGCTGGGCTGCTGGGGGCAGAGCCGCGGG

GCCGCAGGCGGGTGCCCTAGAGTCTCAAGCATCTTCTGACTCCGA

GTGGAGGGGATCTGTCCCGCTACGGGCTCGCCCTGGGCGGGGTC

TGCAGAGACCGCTCGCGGCGGCCATTTTGTGTGCCACGCATGGCG

GTACC
```

The restriction enzyme sites for EcoRI and KpnI (underlined) were added to either end of the sequence for easier manipulation.

The viral IL-17 probe (AJ410493.1) has the sequence:

```
                                      (SEQ ID NO: 13)
GGTACCAAACCAACAAGCCAGAACTTAGATTAAACTTTTT

TATTTAAAAGAAAAAGATAATCAAGTTTTTGGTTTTTAGCGAAAT

GTTACTTTTCAAAATTAAGATAGCTCTTAGTCTACATTGTGAACA

ATAGGAGTAACGCATGTGCAACCTACAGTCACTAGCATCTTCTCT

AGCCGAAATGAATTAGGGCAAGGGTTATGCCCTTTGCGCACTACT

AGAATCTCTTGTTGGATAGGGACTGAGTTCATGTGGTAGTCTACA

TTCCCATCAGCATTAACACATCCTAAGTAGCGACACTTTGCTTCC

CAAATCACAGAAGGATATCTATCTTGATCTTCATTGCGATAGAGA

GTCCAAGGAGACGTAGATCTATTGTAGTAGTCTGAAGCCCTTTA

GAACTAGTATTCCAGTTACGGATGCTCAAAGTAACCATCACAGAC

CGTGGGAAGCTATTGTTAGCAGCTAAGCATCTTGGGGTTTGTGCG

CTGGTTATTTCTGACTTTACTATACAATCTATGCTCAGCAGCAGA

AGTAACACAAGTGAAGTCTTTCTAAATGTCATAATTACTTCTTTA

AATTATCTATACATGTATAAACAGATAGGCTTGCTATGGTTTACA

CTAAATGAATGTTTGTTTATATACTTTAGAGTCTTTTATATTGAT

ACAAACTTCTTGCTGCCATATTTTGCTAGTAAAATACAGGGACAC

CAATACTATACAGAAACATTTTTATTTAAGATTTGCATTTCAGAC

ACTAAGTTATAGCAAACAAGTAATATTGCAATACACAAAGCATTT

ATTTTAGTATGATAAACACATTCCAACAGTAATTTATGGAGATGA

ACTAGTCTTTCTAGA
```

The restriction enzyme sites for KpnI and XbaI (underlined) were added to either end of the sequence for easier manipulation.

The viral StpA probe (GenBank: M28071.1) has the sequence:

```
                                      (SEQ ID NO: 14)
TCTAGAGGGCTTGAACAGTTGTGGGACCCTTACTCTAGCA

GCGCCTCGGCCTAGCCAGGGCTCTGGGGACTGGCTCTAAGCACAG

GGGCACAGCGCCCCCGGGCCTGCGGTGGCCTGGGGACACAACAGG

AGCTCTGGAATCTCAGCCCAGAGGGGTGCGGGGCGGTCGCGAGGG

TCTAGCGCCTCGAAACCGGCTCGGAGCACAAGCAGACTCTAGCCC

CCTCCCCTAGTACACAGAGCCCAGCAGGCAGCTACAGCCGCTCAA

CGCGAGTCCCTCCCCTTGCTCAAGCTCTTTAGTACACTTTTTGTC

TTTTATACAATAGTTTTATTACTGCATAGTATAAGACATTTACTG

CAGCACTATGTGATTCACTTTGATTCTTTTACATTTTTTTAAACA

TAATTACTAGCATTAAACCAATTATGATTAATAGCAAAACAATAA

TAACTAGCAGCAATAGGATAGTTACAGAACAGTCTGTGCATTTGT

CACCTTCTTGCTCGTGTTCACTGTGCAGGCTTCCGACTTCTGCGT

AGACATGTTCTTCACTTCCTGCTCCTCCGCAGCCACTGACACGTA

CTGCTGATAAGCCTACTGGGGTGCTTAAATGTGATGAGCTCCGTG

AGCCAGATGGTGTTGGTAAGCCTACTGCTCCCGATAGTGCTGTTG

GTCTTCCTGGGCATCCGCTTTCTTGCACTGGGTGGCCAAGCAAGC

AGTAGGGATTATAAGGCCCAAAGGGCCCTGCATTTAAAAGCGTTA

CAGGTAAGTATGGTGTAGGTCCATCATCTCCATCACTTCTTTCAT

CAGTATTGTGTGGAGGATCTCCGTTGCTTTCATCGTTTTCTTGTG

GGTCTCCTTCACCTAGACCTCTTGCCATTTTCTTACACGTCTAAG

CTTCAGTTTGTTTAGCTGATTCTTGTAGTGTTGTCTGTCTTGCTA

ATTCTTATATAGTAGCTTGTTACTTCTTGGAAAGTCCAGCAAGAT

GGTGTCCTGTTTAACAGCTTGACCACATGTTTTACAGGACTTAAA

AATTTAAATTTTAACCTTTTGACAAAGAGCAAAAATGAATAAAAA

GCTACAGCTGTATGACTCTTATCTTTTAACATAGTAGCAATGCAC

TTACGTGTTAACTTATTTTATTATAAGTTGATGCTTGCTATTGTA

GTGCTTATAGCAGCTTTTATATCAGCTTTTAGTAGTTATTGCTAG

CTTTATCTAGCTTTGCTCTCAATGAGCTGGATCC
```

The restriction enzyme sites for XbaI and BamHI (underlined) were added to either end of the sequence for easier manipulation.

The plasmids produced were used to transform *Escherichia coli* strain Top10, selecting for the ampicillin resistance gene from the pUC57 vector using 100 μg/ml ampicillin. The bacteria containing the plasmids were grown up to isolate plasmid, using the miniprep kit from Promega, following the manufactures instructions.

One μg of each of the plasmids was labeled using the ENZO BioProbe nick-translation kit with bio-16-dUTP in 50 μl, following the manufacturer's instructions. After labeling, the product was concentrated by the addition of 5 μl of 3 M sodium acetate, pH 7 and 130 μl of ethanol, followed by freezing for 2 hours at −80° C., then precipitating the nucleic acid by centrifugation at 16,100×g for 20 minutes. The supernatant was removed by aspiration, and the DNA pellet was washed using 70% ethanol. The dried pellet was then ready for resuspension and use.

Example 10: Detection of Herpesvirus Saimiri in Clinical Samples Using Biotinylated Probes The biotinylated probes described in Example 9 were tested in serial sections of lung tissue samples from IPF patients. When tested in serial sections, the probes for the IL-17 and DNA polymerase sequences (respectively, FIG. 10A, 10C), and the probes for STP and terminal repeat sequences (data not shown) yielded signal in the same regenerating epithelial cells in IPF as the LNA probes tested in Example 6 (FIG. 6A-6H). No signal was apparent in the negative controls. Co-expression analysis (FIG. 10B, 10D) showed that the same set of cells that expressed the viral DNA sequences also co-expressed cyclin D as determined by antibody staining. (Compare FIG. 10A with FIG. 10B, and FIG. 10C with FIG. 10D).

Example 11: Effects of Stringency on Hybridization and Detection of HVS Probes in IPF Clinical Specimens Hybridizations of serial sections of paraffin-embedded IPF samples was carried out as described previously using either the STP LNA probe as described in Example 1 or a pool of biotin-labeled large probes as described in Example 9. In the case of the LNA probes, washing was modified by the addition of a high stringency wash at 50° C. In the case of the biotin probes, various washing conditions were used as described in Table 3. For comparison purposes, scores were assigned for signals in the specimens for each washing condition as also described in Table 3. As controls, clinical specimens from Kaposi's sarcoma and Burkitts lymphoma were included as well as both HVS-infected and uninfected Jurkat cells. As evidenced in Table 3, all five IPF specimens scored positively with the Herpesvirus saimiri specific probes, although there were differences in the response to increasing stringency conditions used for washing the slides. Three of the specimens, 13743, 7480 and 71706, showed a difference in hybridization in only one level between the very low stringency and high stringency washes. This result is consistent with either perfect or a very high level of homology between probe and target. On the other hand, two of the specimens (994326 and 205601) showed a difference in two levels, with signal going from 3/0 to 1/0 with increasing stringency for 994326 and from 2/0 to 0/0 (undetectable) for 20560, indicating that although they did bind to the viral targets, the probes had mismatches with the viral sequences. It should also be understood that the results are essentially a qualitative difference and that there is leeway in the signal scores. Interestingly, neither the Kaposi (HHV8) or Burkitt (EBV) specimens scored positive for probe binding even under the non-stringent washing conditions. The control results indicate that the Herpesvirus saimiri virus specific probes do not bind indiscriminately to other herpesvirus sequences, but rather, that sequences having homology with Herpesvirus saimiri must be present for signal generation.

TABLE 3

Compilation of HVS Low vs High Stringency using Biotin or LNA Probe Data

| Case | LNA (high stringency) | Biotin (very low stringency*) | Biotin (low stringency) | Biotin (high stringency) |
|---|---|---|---|---|
| 137431 IPF | 3/0** | 2/0 | 2/0 | 3/0 |
| 99 4326 IPF | 3/1 | 3/0 | 3/0 | 1/0 |
| 205601 IPF | 3/1 | 2/0 | 1/0 | 0/0 |
| 7480 IPF | 3/0 | 3/0 | 3/0 | 2/0 |
| 71706 IPF | 2/0 | 2/0 | ND | 1/0 |
| A (hantavirus induced IP) | 0/0 | 0/0 | 0/0 | 0/0 |
| 8391 - mediastinal lymphoma*** | 3/1 | 1/0 | 2/0 | 0/0 |
| 3406 - mediastinal lymphoma | 3/0 | 2/0 | 1/0 | 1/0 |
| 4785 - mediastinal lymphoma | 0/0 | 0/0 | 0/0 | 0/0 |
| 22926 - mediastinal lymphoma | 0/0 | 0/0 | 0/0 | 0/0 |
| 6593 - mediastinal lymphoma | 0/0 | 0/0 | 0/0 | 0/0 |
| 60218 Castleman's disease*** | 3/1 | 2/0 | 2/0 | 0/0 |
| 32714 Castleman's disease | 3/0 | 2/0 | 3/0 | 0/0 |
| Castleman's disease GN | 3/0 | 3/0 | 3/0 | 0/0 |
| Kaposi's sarcoma (skin) | 0/0 | 0/0 | 0/0 | 0/0 |
| Burkitt's lymphoma | 0/0 | 0/0 | 0/0 | 0/0 |
| Jurkat cells NOT infected | 0/0 | 0/1 | 0/0 | 0/0 |
| Jurkat cells Infected | 3/0 | 2/1 | 2/0 | 2/0 |

*high stringency is 0.1XSSC and 2% bovine serum albumin (BSA) at 50 C. for 5 min, low stringency - 0.1XSSC and 2% bovine serum albumin (BSA) at 4 C. for 5 min, very low stringency = 1.0 XSSC and 2% bovine serum albumin (BSA) at 4 C. for 5 min
**scores reported as SIGNAL/BACKGROUND with scores of either 0, 1 (weak), 2+ (moderate) and 3+ (intense)
***For the Castleman/Kaposi's/Burkitts/mediastinal lymphoma only the Stp and IL-17 probes; for IPF DNA polymerase and Terminal repeat probes also used Example 12: Effects of Stringency on Hybridization and Detection of HVS Probes with Other Lung Disease Clinical Specimens Hybridizations and washing conditions as described in Example 11 were also applied to a series of clinical specimens from lymphomas and Castleman's disease, since these specimens have previously also been seen to have detectable virus sequences with Herpesvirus saimiri probes (Examples 7 and 8). The results set forth in Table 3 were mixed. Hybridization strength in the lymphoma specimens that were positive for viral sequences showed a difference of only one level between the high stringency and very low stringency conditions. On the other hand, in the Castleman's disease specimens, all three specimens produced very good signals (2/0, 3/0 and 3/0) under very low stringency and maintained their signals when stringency was increased to "low stringency". However, the signal was completely lost when high stringency conditions were applied using the biotin labeled STP and IL-17 probes described in Example 9. In contrast, the STP LNA probes continued to produce high signals in all three samples, even after high stringency washing. These results are consistent with the presence in these Castleman's disease specimens of a gammavirus that is homologous to Herpesvirus saimiri, but that has genomic mismatches.

7. ADDITIONAL EMBODIMENTS

This section includes additional embodiments.

1. A method of diagnosing or prognosticating a viral disease in a patient comprising a step of detecting the presence of a virus-specific element from a virus in a clinical sample from said patient.
2. The method of embodiment 1, wherein the virus-specific element is a nucleic acid.
3. The method of embodiment 2, wherein said nucleic acid is mRNA.
4. The method of embodiment 2, wherein said nucleic acid is DNA.
5. The method of embodiment 2, wherein said clinical sample is selected from whole blood, serum, tissue, lavage and combinations thereof.
6. The method of embodiment 5, wherein said tissue sample is a lung biopsy.
7. The method of embodiment 6, wherein said tissue sample comprises a paraffin embedded slide.
8. The method of embodiment 2, wherein said detecting step is carried out by hybridizing the nucleic acid sequence with a nucleic acid probe comprising a sequence that is complementary to a virus-specific nucleic acid.
9. The method of embodiment 8, where said nucleic acid probe comprises one or more modified nucleotides.
10. The method of embodiment 9, wherein said one or more modified nucleotides comprises a modified base, a modified sugar, a modified backbone or combinations thereof.
11. The method of embodiment 10, wherein the modified base is selected from 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.
12. The method of embodiment 10, wherein the modified sugar is selected from a 2'-O-alkyl-ribose sugar, a 2'-amino-deoxyribose sugar, a 2'-fluoro-deoxyribose sugar, a 2'-fluoro-arabinose sugar, a 2'-O-methoxyethyl-ribose sugar and an LNA sugar.
13. The method of embodiment 10, wherein the backbone modification is selected from a peptide nucleic acid, a phosphorothioate linkage, a methylphosphonate, an alkylphosphonate, a phosphate ester, an alkylphosphonothioate, a phosphoramidate, a carbamate, a carbonate, a phosphate triester, an acetamidate, a carboxymethyl ester, a methylphosphorothioate, a phosphorodithioate, a p-ethoxy linkage, and combinations thereof.
14. The method of embodiment 8, wherein said detecting step is carried out with a nucleic acid isolated from the clinical sample of said patient.
15. The method of embodiment 8, wherein said detecting step is carried out by fluorescence in-situ hybridization.
16. The method of embodiment 2, further comprising a step of amplifying said nucleic acid prior to said detecting step.
17. The method of embodiment 16, wherein said amplifying step is carried out by PCR or RT-PCR.
18. The method of embodiment 16, wherein said amplifying step is an isothermal process.
19. The method of embodiment 18, wherein said isothermal process is selected from the group consisting of an SDA reaction, a 3 SR reaction, a NASBA reaction, a TMA reaction, a LAMP reaction, an HAD reaction, a LAMP reaction, stem-loop amplification, a SMART reaction, an IMDA reaction, a SPIA reaction, and a cHDA reaction.
20. The method of embodiment 16, wherein said amplifying step is carried out with a nucleic acid isolated from the clinical sample of said patient.
21. The method of embodiment 16, wherein said detecting step is carried out in situ with a specimen from said patient.
22. The method of embodiment 2, wherein the virus is Herpesvirus saimiri or a related virus.
23. The method of embodiment 2, wherein the viral disease is idiopathic pulmonary fibrosis, a lymphoproliferative disease or cancer.
24. The method of embodiment 22, wherein the nucleic acid is selected from a major single-stranded DNA binding protein (mDNA-BP) gene, a DNA polymerase gene, a DNA packaging, a terminase gene, a helicase-primase complex gene, a uracil DNA glycosylase gene, a deoxyuridine triphosphatase (dUTPase) gene, a DNA polymerase processivity factor gene, a capsid assembly and DNA maturation protein gene, a TER gene, an STP gene, an IL-17 gene, a Cyclin D gene, a glycoprotein B gene, a Sag gene, a CD59 gene, a Bcl2 gene, a capsid protein gene, an envelope protein gene, a ribonucleotide reductase gene, a tegument protein gene, a FLICE interacting protein (FLIP) gene, an IL-8 receptor gene, a glycoprotein M gene, a FGARAT gene, a thymidine kinase gene, a phosphotransferase gene, a tyrosine kinase gene, a dihydrofolate reductase (DHFR) gene, and a thymidylate synthase (TS) gene, a fragment of any of the foregoing, and combinations thereof.
25. The method of embodiment 1, wherein the virus-specific element is a protein or peptide.
26. The method of embodiment 25, wherein said protein is an analog of a human protein, or said peptide is derived from an analog of a human protein.
27. The method of embodiment 25, wherein said clinical sample is selected from whole blood, serum, tissue, lavage and combinations thereof.
28. The method of embodiment 27, wherein said tissue sample is a lung biopsy.
29. The method of embodiment 28, wherein said tissue sample comprises a paraffin embedded slide.
30. The method of embodiment 25, wherein said detecting step is carried out using an antibody to said virus-specific protein or peptide.
31. The method of embodiment 30, wherein said antibody recognizes an epitope present in a human protein or peptide and in a homologous virus-specific protein or peptide.
32. The method of embodiment 30, wherein said antibody recognizes an epitope present in a virus-specific protein or peptide that is not present in a human protein or peptide.
33. The method of embodiment 30, wherein said detecting step is carried out using an enzyme-linked immuno sorbent assay.
34. The method of embodiment 25 wherein said virus-specific protein is an enzyme.
35. The method of embodiment 34 wherein said detecting step is carried out using an enzyme activity assay.

36. The method of embodiment 34, wherein said detecting step is carried out by detecting a metabolite of the enzyme.
37. The method of embodiment 25, wherein the protein or peptide is from Herpesvirus saimiri or a related virus.
38. The method of embodiment 25, wherein the viral disease is idiopathic pulmonary fibrosis.
39. The method of embodiment 37, wherein said protein is selected from IL-17, thymidylate synthase, dihydrofolate reductase, cyclin D, STP, Sag, CD59, Bcl2, FGARAT, FLIP, VP23, glycoprotein B, glycoprotein M, FGARAT, thymidine kinase, phosphotransferase, tyrosine kinase, uracil DNA glycosylase, deoxyuridine triphosphatase, major single-stranded DNA binding protein (mDNA-BP), DNA polymerase, DNA packaging terminase, helicase-primase complex, uracil DNA glycosylase, deoxyuridine triphosphatase (dUTPase), DNA polymerase processivity factor, capsid assembly and DNA maturation protein, a capsid protein, an envelope protein, ribonucleotide reductase, tegument protein, IL-8 receptor, or said peptide is derived from any of the foregoing.
40. The method of embodiment 25, which further comprises a step of detecting a pathogen other than a virus-specific pathogen that is associated with a viral disease.
41. A method of diagnosing or prognosticating a viral disease in a patient comprising a step of detecting the presence of a human antibody to a virus-specific element in a clinical sample from the patient.
42. The method of embodiment 41, wherein said clinical sample is selected from whole blood, serum, tissue, lavage and combinations thereof.
43. The method of embodiment 42, wherein said tissue sample is a lung biopsy.
44. The method of embodiment 43, wherein said tissue sample comprises a paraffin embedded slide.
45. The method of embodiment 41, wherein said detecting step is carried out using an enzyme-linked immune sorbent assay.
46. The method of embodiment 41, wherein said human antibody is to a virus-specific element selected from a capsid protein, an envelope protein, IL-17, thymidylate synthase, dihydrofolate reductase, cyclin D, STP, Sag, CD59, Bcl2, FGARAT, FLIP, VP23, glycoprotein B, glycoprotein M, FGARAT, thymidine kinase, phosphotransferase, tyrosine kinase, uracil DNA glycosylase, deoxyuridine triphosphatase, major single-stranded DNA binding protein (mDNA-BP), DNA polymerase, DNA packaging terminase, helicase-primase complex, uracil DNA glycosylase, deoxyuridine triphosphatase (dUTPase), DNA polymerase processivity factor, capsid assembly and DNA maturation protein, ribonucleotide reductase, tegument protein, IL-8 receptor and a peptide derived from any of the foregoing.
47. The method of embodiment 41, wherein said virus is Herpesvirus saimiri or a related virus.
48. The method of embodiment 41, wherein said disease is idiopathic pulmonary fibrosis, a lymphoproliferative disease or cancer.
49. The method of embodiment 1, wherein said virus-specific element is a viral particle.
50. The method of embodiment 49, wherein said clinical sample is selected from whole blood, serum, tissue, lavage and combinations thereof.
51. The method of embodiment 50, wherein said tissue sample is a lung biopsy.
52. The method of embodiment 51, wherein said tissue sample comprises a paraffin embedded slide.
53. The method of embodiment 49, wherein said detecting step is carried out using an antibody to an envelope protein or a capsid protein of the virus.
54. The method of embodiment 49, wherein the viral particle is detected by an enzyme-linked immune sorbent assay or flow cytometry.
55. A method of diagnosing or prognosticating a viral disease in a patient comprising a step of detecting the presence of a cell infected by the virus in a clinical sample from said patient.
56. The method of embodiment 55, wherein said clinical sample is selected from whole blood, serum, tissue, lavage and combinations thereof.
57. The method of embodiment 56, wherein said tissue sample is a lung biopsy.
58. The method of embodiment 57, wherein said tissue sample comprises a paraffin embedded slide.
59. The method of embodiment 49 or embodiment 55, wherein the virus is Herpesvirus saimiri or a related virus.
60. The method of embodiment 49 or 55, wherein the disease is idiopathic pulmonary fibrosis, a lymphoproliferative disease or cancer.
61. A method of diagnosing or prognosticating a viral disease in a patient comprising the steps of:
(a) measuring expression of a patient nucleic acid or protein in said patient; and
(b) measuring expression of said patient nucleic acid or protein in a healthy individual, wherein expression measured in step (a) that is at least two-fold higher than expression measured in step (b) is indicative of viral disease in said patient.
62. The method of embodiment 61, wherein said protein is a viral analog of a human protein.
63. The method of embodiment 62, wherein said protein is selected from IL-17, cyclin D1 thymidylate synthase, and dihydrofolate reductase.
64. The method of embodiment 61, wherein said nucleic acid is mRNA that encodes a protein that is a viral analog of a human protein.
65. The method of embodiment 64, wherein said nucleic acid encodes a protein selected from IL-17, cyclin D1 thymidylate synthase, and dihydrofolate reductase.
66. A method of monitoring progression of a viral disease in a patient comprising the steps of:
(a) measuring a first level of a virus-specific element in a first clinical sample from the patient;
(b) measuring a second level of said virus-specific element in a second clinical sample from the patient;
(c) comparing the first level measured in step (a) and the second level measured in step (b),
wherein the first level measured in step (a) that is less than the second level measured in step (b) is indicative of disease progression; and
wherein the first level measured in step (a) that is greater than or equal to the second level measured in step (b) is indicative of no disease progression or disease remission.
67. The method of embodiment 66, wherein step (b) is performed at least about 1 week after step (a).
68. The method of embodiment 66, wherein the virus-specific element is a virus-specific nucleic acid.
69. The method of embodiment 68, wherein said nucleic acid is DNA.

70. The method of embodiment 68, wherein said nucleic acid is mRNA.
71. The method of embodiment 66, wherein said clinical sample is selected from whole blood, serum, tissue, lavage and combinations thereof.
72. The method of embodiment 71, wherein said tissue sample is a lung biopsy.
73. The method of embodiment 72, wherein said tissue sample comprises a paraffin embedded slide.
74. The method of embodiment 66, wherein said virus-specific element is a nucleic acid sequence selected from a major single-stranded DNA binding protein (mDNA-BP) gene, a DNA polymerase gene, a DNA packaging, a terminase gene, a helicase-primase complex gene, a uracil DNA glycosylase gene, a deoxyuridine triphosphatase (dUTPase) gene, a DNA polymerase processivity factor gene, a capsid assembly and DNA maturation protein gene, a TER gene, an STP gene, a repetitive DNA sequence, an IL-17 gene, a Cyclin D gene, a glycoprotein B gene, a Sag gene, a CD59 gene, a Bcl2 gene, a capsid protein gene, an envelope protein gene, a ribonucleotide reductase gene, a tegument protein gene, a FLICE interacting protein (FLIP) gene, an IL-8 receptor gene, a glycoprotein M gene, a FGARAT gene, a thymidine kinase gene, a phosphotransferase gene, a tyrosine kinase gene, a dihydrofolate reductase (DHFR) gene, and a thymidylate synthase gene, a fragment of any of the foregoing, and combinations thereof.
75. The method of embodiment 66, wherein said virus is Herpesvirus saimiri or a related virus.
76. The method of embodiment 66, wherein the disease is idiopathic pulmonary fibrosis, a lymphoproliferative disease or cancer.
77. The method of embodiment 66, wherein said virus-specific element is a protein or peptide.
78. The method of embodiment 77, wherein said protein is an analog of a human protein, or said peptide is derived from an analog of a human protein.
79. The method of embodiment 77, wherein said clinical sample is selected from whole blood, serum, tissue, lavage and combinations thereof.
80. The method of embodiment 79, wherein said tissue sample is a lung biopsy.
81. The method of embodiment 80, wherein said tissue sample comprises a paraffin embedded slide.
82. The method of embodiment 77, wherein said detecting step is carried out using an antibody to said virus-specific protein or peptide.
83. The method of embodiment 82, wherein said antibody recognizes an epitope present in a human protein or peptide and in a homologous virus-specific protein or peptide.
84. The method of embodiment 82, wherein said antibody recognizes an epitope present in a virus-specific protein or peptide that is not present in a human protein or peptide.
85. The method of embodiment 82, wherein said detecting step is carried out using an enzyme-linked immuno sorbent assay.
86. The method of embodiment 77 wherein said virus-specific protein is an enzyme.
87. The method of embodiment 86 wherein said detecting step is carried out using an enzyme activity assay.
88. The method of embodiment 86, wherein said detecting step is carried out by detecting a metabolite of the enzyme.
89. The method of embodiment 77, wherein the virus is Herpesvirus saimiri or a related virus.
90. The method of embodiment 77, wherein the disease is idiopathic pulmonary fibrosis, a lymphoproliferative disease or cancer.
91. The method of embodiment 89, wherein said protein is selected from IL-17, thymidylate synthase, dihydrofolate reductase, cyclin D, STP, Sag, CD59, Bcl2, FGARAT, FLIP, VP23, glycoprotein B, glycoprotein M, FGARAT, thymidine kinase, phosphotransferase, tyrosine kinase, uracil DNA glycosylase, deoxyuridine triphosphatase, major single-stranded DNA binding protein (mDNA-BP), DNA polymerase, DNA packaging terminase, helicase-primase complex, uracil DNA glycosylase, deoxyuridine triphosphatase (dUTPase), DNA polymerase processivity factor, capsid assembly and DNA maturation protein, a capsid protein, an envelope protein, ribonucleotide reductase, tegument protein, IL-8 receptor, or said peptide is derived from any of the foregoing.
92. A method of monitoring progression of a viral disease in a patient comprising the steps of:
(a) measuring a first level of a patient antibody to a virus-specific element in a first clinical sample from the patient;
(b) measuring a second level of the patient antibody to a virus-specific element in a second clinical sample from the patient;
(c) comparing the first level measured in step (a) and the second level measured in step (b),
wherein the first level measured in step (a) that is less than the second level measured in step(b) is indicative of disease progression; and
wherein the first level measured in step (a) that is greater than or equal to the second level measured in step (b) is indicative of no disease progression or disease remission.
93. The method of embodiment 92, wherein step (b) is performed at least about 1 week after step (a).
94. The method of embodiment 92, wherein said clinical sample is selected from whole blood, serum, tissue, lavage and combinations thereof
95. The method of embodiment 94, wherein said tissue sample is a lung biopsy.
96. The method of embodiment 95, wherein said tissue sample comprises a paraffin embedded slide.
97. The method of embodiment 96, wherein said measuring steps are carried out using an enzyme-linked immune sorbent assay.
98. The method of embodiment 92, wherein said human antibody is to a virus-specific element selected from a capsid protein, an envelope protein, IL-17, thymidylate synthase, dihydrofolate reductase, cyclin D, STP, Sag, CD59, Bcl2, FGARAT, FLIP, VP23, glycoprotein B, glycoprotein M, FGARAT, thymidine kinase, phosphotransferase, tyrosine kinase, uracil DNA glycosylase, deoxyuridine triphosphatase, major single-stranded DNA binding protein (mDNA-BP), DNA polymerase, DNA packaging terminase, helicase-primase complex, uracil DNA glycosylase, deoxyuridine triphosphatase (dUTPase), DNA polymerase processivity factor, capsid assembly and DNA maturation protein, ribonucleotide reductase, tegument protein, IL-8 receptor and a peptide derived from any of the foregoing.
99. The method of embodiment 92, wherein said virus is Herpesvirus saimiri or a related virus.

100. The method of embodiment 92, wherein the disease is idiopathic pulmonary fibrosis, a lymphoproliferative disease or cancer.

101. A method of monitoring the efficacy of a therapy for treatment of a viral disease comprising the steps of:
(a) measuring a first level of a virus-specific element in a first clinical sample from an untreated patient;
(b) measuring a second level of said virus-specific element in a second clinical sample from said patient after treatment; and
(c) comparing the first level measured in step (a) and the second level measured in step (b),
wherein the first level measured in step (a) that is greater than or equal to the second level measured in step (b) is indicative of the efficacy of the therapy.

102. The method of embodiment 101, wherein step (b) is performed at least about 1 week after the therapy is administered.

103. The method of embodiment 101, wherein said clinical sample is selected from whole blood, serum, tissue, lavage and combinations thereof 104. The method of embodiment 103, wherein said tissue sample is a lung biopsy.

105. The method of embodiment 104, wherein said tissue sample comprises a paraffin embedded slide.

106. The method of embodiment 101, wherein said virus-specific element is a nucleic acid.

107. The method of embodiment 106, wherein said nucleic acid is mRNA.

108. The method of embodiment 106, wherein said nucleic acid is DNA.

109. The method of embodiment 106, wherein the nucleic acid is selected from a major single-stranded DNA binding protein (mDNA-BP) gene, a DNA polymerase gene, a DNA packaging, a terminase gene, a helicase-primase complex gene, a uracil DNA glycosylase gene, a deoxyuridine triphosphatase (dUTPase) gene, a DNA polymerase processivity factor gene, a capsid assembly and DNA maturation protein gene, a TER gene, an STP gene, an IL-17 gene, a Cyclin D gene, a glycoprotein B gene, a Sag gene, a CD59 gene, a Bcl2 gene, a capsid protein gene, an envelope protein gene, a ribonucleotide reductase gene, a tegument protein gene, a FLICE interacting protein (FLIP) gene, an IL-8 receptor gene, a glycoprotein M gene, a FGARAT gene, a thymidine kinase gene, a phosphotransferase gene, a tyrosine kinase gene, a dihydrofolate reductase (DHFR) gene, and a thymidylate synthase gene, a fragment of any of the foregoing, and combinations thereof.

110. The method of embodiment 101, wherein the virus-specific element is a protein or peptide.

111. The method of embodiment 110, wherein the protein is an enzyme.

112. The method of embodiment 110, wherein the protein is selected from a capsid protein, an envelope protein, IL-17, thymidylate synthase, dihydrofolate reductase, cyclin D, STP, Sag, CD59, Bcl2, FGARAT, FLIP, VP23, glycoprotein B, glycoprotein M, FGARAT, thymidine kinase, phosphotransferase, tyrosine kinase, uracil DNA glycosylase, deoxyuridine triphosphatase, major single-stranded DNA binding protein (mDNA-BP), DNA polymerase, DNA packaging terminase, helicase-primase complex, uracil DNA glycosylase, deoxyuridine triphosphatase (dUTPase), DNA polymerase processivity factor, capsid assembly and DNA maturation protein, ribonucleotide reductase, tegument protein, IL-8 receptor and a peptide derived from any of the foregoing.

113. The method of embodiment 111, wherein the protein is selected from thymidylate synthase, dihydrofolate reductase, thymidine kinase, phosphotransferase, tyrosine kinase, uracil DNA glycosylase, deoxyuridine triphosphatase, DNA polymerase, DNA packaging terminase, helicase-primase complex, uracil DNA glycosylase, deoxyuridine triphosphatase (dUTPase), DNA polymerase processivity factor, and ribonucleotide reductase.

114. The method of embodiment 111, wherein the virus-specific element is a virus-specific metabolite of said enzyme.

115. The method of embodiment 101, wherein said virus is Herpesvirus saimiri or a related virus.

116. The method of embodiment 101, wherein said viral disease is idiopathic pulmonary fibrosis, a lymphoproliferative disease or cancer.

117. A method of monitoring the efficacy of a therapy for treatment of a viral disease in a patient comprising the steps of:
(a) measuring a first level of a patient antibody to a virus-specific element in a first clinical sample from the patient;
(b) measuring a second level of the patient antibody to the virus-specific element in a second clinical sample from the patient;
(c) comparing the first level measured in step (a) and the second level measured in step (b),
wherein the first level measured in step (a) that is greater than or equal to the second level measured in step (b) is indicative of the efficacy of the therapy.

118. The method of embodiment 117, wherein step (b) is performed at least about 1 week after step (a).

119. The method of embodiment 117, wherein said clinical sample is selected from whole blood, serum, tissue, lavage and combinations thereof 120. The method of embodiment 119, wherein said tissue sample is a lung biopsy.

121. The method of embodiment 120, wherein said tissue sample comprises a paraffin embedded slide.

122. The method of embodiment 117, wherein said measuring steps are carried out using an enzyme-linked immune sorbent assay.

123. The method of embodiment 117, wherein said human antibody is to a virus-specific element selected from a capsid protein, an envelope protein, IL-17, thymidylate synthase, dihydrofolate reductase, cyclin D, STP, Sag, CD59, Bcl2, FGARAT, FLIP, VP23, glycoprotein B, glycoprotein M, FGARAT, thymidine kinase, phosphotransferase, tyrosine kinase, uracil DNA glycosylase, deoxyuridine triphosphatase, major single-stranded DNA binding protein (mDNA-BP), DNA polymerase, DNA packaging terminase, helicase-primase complex, uracil DNA glycosylase, deoxyuridine triphosphatase (dUTPase), DNA polymerase processivity factor, capsid assembly and DNA maturation protein, ribonucleotide reductase, tegument protein, IL-8 receptor and a peptide derived from any of the foregoing.

124. The method of embodiment 117, wherein said virus is Herpesvirus saimiri or a related virus.

125. The method of embodiment 117, wherein said disease is idiopathic pulmonary fibrosis, a lymphoproliferative disease or cancer.

126. A method of identifying in vitro a therapeutic agent for the treatment of a viral disease, comprising the steps of
(a) exposing a virus culture to said agent;
(b) measuring the replication of said virus culture; and
(c) comparing said replication measured in step (b) with the replication of a virus culture that has not been exposed to the agent,
wherein replication measured in step (b) that is lower than replication of a virus culture that has not been exposed to the agent identifies a therapeutic agent for the treatment of said viral disease.

127. The method of embodiment 126, wherein the virus is cultured in a permissive cell line.

128. The method of embodiment 126, wherein the virus is cultured in a semi-permissive cell line.

129. The method of embodiment 126, wherein the virus is cultured in vitro in human T-lymphocytes.

130. The method of embodiment 126, wherein viral replication is measured by measuring an amount of viral particles.

131. The method of embodiment 126, wherein viral replication is measured by measuring an amount of infected host cells.

132. The method of embodiment 126, wherein replication is measured by measurement of a virus-specific element.

133. The method of embodiment 132, wherein said virus-specific element is a nucleic acid.

134. The method of embodiment 133, which includes a step of amplifying said nucleic acid before said measuring step (b).

135. The method of embodiment 133 wherein the nucleic acid is DNA.

136. The method of embodiment 133, wherein the nucleic acid is mRNA.

137. The method of embodiment 132, wherein said virus-specific element is a protein or peptide.

138. The method of embodiment 137, wherein the protein is an enzyme.

139. The method of embodiment 138, wherein said virus-specific element is a metabolite of said enzyme.

140. The method of embodiment 137, wherein the protein is selected from IL-17, thymidylate synthase, dihydrofolate reductase, cyclin D, STP, Sag, CD59, Bcl2, FGARAT, FLIP, VP23, glycoprotein B, glycoprotein M, FGARAT, thymidine kinase, phosphotransferase, tyrosine kinase, uracil DNA glycosylase, deoxyuridine triphosphatase, major single-stranded DNA binding protein (mDNA-BP), DNA polymerase, DNA packaging terminase, helicase-primase complex, uracil DNA glycosylase, deoxyuridine triphosphatase (dUTPase), DNA polymerase processivity factor, capsid assembly and DNA maturation protein, a capsid protein, an envelope protein, ribonucleotide reductase, tegument protein, IL-8 receptor, or said peptide is derived from any of the foregoing.

141. The method of embodiment 138, wherein the enzyme is selected from thymidylate synthase, dihydrofolate reductase, thymidine kinase, phosphotransferase, tyrosine kinase, uracil DNA glycosylase, deoxyuridine triphosphatase, DNA polymerase, DNA packaging terminase, helicase-primase complex, uracil DNA glycosylase, deoxyuridine triphosphatase (dUTPase), DNA polymerase processivity factor, and ribonucleotide reductase.

142. The method of embodiment 126, wherein the virus is Herpesvirus saimiri or a related virus.

143. The method of embodiment 126, wherein the viral disease is idiopathic pulmonary fibrosis, a lymphoproliferative disease or cancer.

144. A method of identifying in vitro a therapeutic agent for the treatment of a viral disease, comprising the steps of
(a) exposing a virus culture to an agent;
(b) measuring the activity of a viral protein in said culture; and
(c) comparing said activity measured in step (b) with the activity of the viral protein in a virus culture that has not been exposed to the agent,
wherein activity of the viral protein measured in step (b) that is lower than the activity of the viral protein in the virus culture that has not been exposed to the agent identifies a therapeutic agent for the treatment of said viral disease.

145. The method of embodiment 144, wherein the viral protein is an enzyme.

146. The method of embodiment 145, wherein the activity of the enzyme is measured by measuring an amount of a metabolite of said enzyme.

147. The method of embodiment 145, wherein the viral protein is selected from thymidylate synthase, dihydrofolate reductase, thymidine kinase, phosphotransferase, tyrosine kinase, uracil DNA glycosylase, deoxyuridine triphosphatase, DNA polymerase, DNA packaging terminase, helicase-primase complex, uracil DNA glycosylase, deoxyuridine triphosphatase (dUTPase), DNA polymerase processivity factor, and ribonucleotide reductase.

148. The method of embodiment 144, wherein the viral protein is a cytokine.

149. The method of embodiment 148, wherein the activity of the protein is measured by measuring the activity of a reporter gene that is regulated by said cytokine.

150. A method of treating a patient suffering from a viral disease comprising administering to the patient an effective amount of an agent identified by the method of embodiment 124 or embodiment 142.

151. The method of embodiment 150, which further comprises administering an effective amount of an anti-viral agent.

152. The method of embodiment 151, wherein the anti-viral agent is selected from the group consisting of acyclovir, vidarabine, idoxuridine, brivudine, cytarabine, foscarnet, docosanol, formivirsen, tromantidine, imiquimod, podophyllotoxin, cidofovir, interferon alpha-2b, peginterferon alpha-2a, ribavirin, moroxydine, valacyclovir, trifluridine, bromovinyldeoxyuridine, and combinations thereof 153. The method of embodiment 150, which further comprises administering an effective amount of IL-10 or an agonist of IL-10.

154. The method of embodiment 153, wherein the agonist of IL-10 is selected from the group consisting of isoproterenol, IT 9302 and combinations thereof.

155. A method of treating a patient suffering from a viral disease comprising administering to the patient an effective amount of an agent that inhibits replication of a virus.

156. The method of embodiment 155, wherein said agent is selected from a nucleotide analog, a viral polymerase inhibitor, an inhibitor of a viral protein essential for viral DNA maturation, an inhibitor of episomal persistence of a genome of the virus, and combinations thereof.

157. A method of treating a patient suffering from a viral disease comprising administering to the patient an effective amount of an agent that down-regulates expression of a virus-specific protein.

158. The method of embodiment 157, wherein said agent is selected from antisense DNA, antisense mRNA, RNAi, a ribosome, and combinations thereof 159. A method of treating a patient suffering from a viral disease, comprising administering to said patient an effective amount of an antagonist of a viral protein or a neutralizing agent that blocks activity of a viral protein.

160. The method of embodiment 159, wherein the antagonist is an antibody to virus-specific IL-17.

161. The method of embodiment 160, wherein the antibody is a monoclonal antibody.

162. The method of embodiment 160, wherein the antibody is a polyclonal antibody.

163. The method of embodiment 160, wherein the antibody is a human antibody.

164. The method of embodiment 160, wherein the antibody is humanized.

165. The method of embodiment 160, wherein the antibody binds to virus-specific IL-17, but not to human IL-17.

166. The method of embodiment 165, wherein the antibody is specific for IL-17A.

167. The method of embodiment 159, wherein the neutralizing agent is an antibody to an IL-17 receptor (IL17R).

168. The method of embodiment 167, wherein the antibody is specific for one or more of IL17RA, IL17RB, and IL17RC.

169. The method of embodiment 167, wherein the antibody is a monoclonal antibody.

170. The method of embodiment 167, wherein the antibody is a polyclonal antibody.

171. The method of embodiment 167, wherein the antibody is a human antibody.

172. The method of embodiment 167, wherein the antibody is humanized.

173. The method of embodiment 160, which further comprises administering an effective amount of IL-10 or an agonist of IL-10.

174. The method of embodiment 173, wherein the agonist of IL-10 is selected from the group consisting of isoproterenol, IT 9302 and combinations thereof.

175. The method of embodiment 159, wherein the neutralizing agent is an antagonist of TGF-β.

176. The method of embodiment 173, wherein the antagonist is an antibody to TGF-β.

177. The method of embodiment 174, wherein the antibody is a monoclonal antibody.

178. The method of embodiment 174, wherein the antibody is a polyclonal antibody.

179. The method of embodiment 174, wherein the antibody is a human antibody.

180. The method of embodiment 174, wherein the antibody is humanized.

181. The method of embodiment 157, wherein the neutralizing agent is an antibody to a TGF-β receptor.

182. The method of embodiment 175, which further comprises administering an effective amount of IL-10 or an agonist of IL-10.

183. The method of embodiment 182, wherein the agonist of IL-10 is selected from the group consisting of isoproterenol, IT 9302 and combinations thereof.

184. The method of embodiment 159, wherein the neutralizing agent is an antagonist of human IL-23.

185. The method of embodiment 184, wherein the antagonist of IL-23 is an antibody.

186. The method of embodiment 185, wherein the antibody is a monoclonal antibody.

187. The method of embodiment 185, wherein the antibody is a polyclonal antibody.

188. The method of embodiment 185, wherein the antibody is a human antibody.

189. The method of embodiment 185, wherein the antibody is humanized.

190. The method of embodiment 185, wherein the neutralizing agent of human IL-23 is an antibody to an IL-23 receptor.

191. The method of embodiment 190, wherein the antibody is a monoclonal antibody.

192. The method of embodiment 190, wherein the antibody is a polyclonal antibody.

193. The method of embodiment 190, wherein the antibody is a human antibody.

194. The method of embodiment 190, wherein the antibody is humanized.

195. The method of embodiment 184, which further comprises administering an effective amount of IL-10 or an agonist of IL-10.

196. The method of embodiment 195, wherein the agonist of IL-10 is selected from the group consisting of isoproterenol, IT 9302 and combinations thereof.

197. The method of embodiment 159, wherein the neutralizing agent is an antagonist of IL-1β.

198. The method of embodiment 197, wherein the antagonist is an antibody to IL-1β.

199. The method of embodiment 198, wherein the antibody is a monoclonal antibody.

200. The method of embodiment 199, wherein the antibody is Canakinumab.

201. The method of embodiment 198, wherein the antibody is a polyclonal antibody.

202. The method of embodiment 198, wherein the antibody is a human antibody.

203. The method of embodiment 198, wherein the antibody is humanized.

204. The method of embodiment 159, wherein the neutralizing agent is a soluble IL-17R extra-cellular domain.

205. The method of embodiment 204, wherein the soluble IL-17R extra-cellular domain is an IL-17RA extra-cellular domain.

206. The method of embodiment 204, wherein the soluble IL-17R extra-cellular domain is an IL-17RB extra-cellular domain.

207. The method of embodiment 204, wherein the soluble IL-17R extra-cellular domain is an IL-17RC extra-cellular domain.

208. The method of embodiment 159, wherein the neutralizing agent is a soluble IL-R8 extra-cellular domain.

209. A method of treating a patient suffering from a viral disease, comprising administering to said patient an effective amount of an agent that inhibits virus entry into a host cell.

210. The method of embodiment 209, wherein said agent is selected from an small molecule or peptide that binds to a virus surface glycoprotein and blocks binding of the virus to a host cell receptor, a soluble extra-cellular domain of a virus-specific glycoprotein, an antibody that binds to a virus-specific glycoprotein and an antibody that binds to a host cell receptor.

211. A method of treating a patient suffering from a viral disease, comprising administering to said patient an effective amount of an agent that inhibits an enzyme of a virus.

212. The method of embodiment 211, wherein the agent is selected from a reversible enzyme inhibitor, an irreversible enzyme inhibitor, a competitive enzyme inhibitor, an uncompetitive enzyme inhibitor, a mixed inhibition enzyme inhibitor, and a non-competitive inhibitor.

213. A vaccine composition against a viral infection comprising an effective immunizing amount of an antigen selected from the group consisting a virus, a viral membrane associated antigen, a viral latency-associated nuclear antigen, a viral cytoplasmic late antigen, a viral nuclear early antigen, a viral antigenic protein or peptide, and combinations thereof, and a pharmaceutically acceptable excipient.

214. The vaccine of embodiment 213, wherein the virus is a live attenuated whole virus.

215. The vaccine of embodiment 213, wherein the virus is an inactivated virus.

216. The vaccine of embodiment 213, wherein the viral membrane associated antigen is in a plasma membrane vesicle.

217. The vaccine of embodiment 214, wherein the live attenuated whole virus comprises an inactivating mutation in the genome of said virus.

218. The vaccine of embodiment 217, wherein the inactivating mutation comprises a deletion, substitution or insertion in an endogenous promoter region of an intermediate-early gene.

219. The vaccine of embodiment 214, wherein said virus is incapable of establishing latent infection.

220. The vaccine of embodiment 213, wherein said pharmaceutically acceptable excipient is selected from the group consisting of an adjuvant, a preservative, a diluent, a stabilizer, a buffer, a solvent, an inactivating agent, a viral inactivator, an antimicrobial, a tonicity agent, a surfactant, a thickening agent and combinations thereof.

221. The vaccine of embodiment 213, wherein the antigenic protein or peptide is a capsid protein, an envelope protein, a peptide derived from either a capsid protein or an envelope protein, and combinations thereof 222. The vaccine of embodiment 220, wherein the adjuvant is selected from the group consisting of an aluminum salt, an organic adjuvant, an oil-in-water adjuvant, a virosome, and an immunological adjuvant.

223. The vaccine of embodiment 221, wherein the adjuvant is selected from the group consisting of aluminum phosphate, aluminum hydroxide, aluminum phosphate, squalene, an extract of Quillaja *saponaria*, MF59, QS21, Malp2, incomplete Freund's adjuvant, complete Freund's adjuvant, Alhydrogel®, 3 De-O-acylated monophosphoryl lipid A (3D-MPL), Matrix-M™ and combinations thereof.

224. The method of embodiment 213, wherein said virus is Herpesvirus saimiri and said viral infection is idiopathic pulmonary fibrosis, a lymphoproliferative disease or cancer.

225. A kit for diagnosing a viral disease in a patient comprising one or more probes complementary to a nucleic acid sequence of a virus.

226. The kit of embodiment 125, wherein said one or more probes comprises one or more affinity-enhancing nucleotides.

227. The kit of embodiment 225, wherein said one or more probes comprises a locked nucleic acid.

228. The kit of embodiment 225, wherein said one or more probes comprises a peptide nucleic acid.

229. The kit of embodiment 225, which further comprises a reagent for amplifying the viral nucleic acid.

230. A kit for diagnosing a viral disease in a patient comprising an immunological reagent for detection and/or quantification of a virus-specific protein, peptide or metabolite.

231. The kit of embodiment 230, wherein the immunological reagent is an antibody to a virus-specific protein, peptide or metabolite.

232. A kit for diagnosing a viral disease in a patient comprising an immunological reagent for detection and/or quantification of a human antibody to a virus-specific element.

233. The kit of embodiment 232, wherein the virus-specific element is a protein, peptide or metabolite.

234. The kit of embodiment 232, wherein the virus-specific element is a viral particle.

235. The kit of embodiment 232, wherein immunological reagent is an antibody to a virus capsid protein or a virus envelope protein.

236. The kit of embodiment 232, wherein the virus-specific element is a viral marker on the surface of an infected host cell.

237. The method of any one of embodiments 225, 230 and 232, which further comprises one or more of (i) a cell line for culturing a virus; (ii) a cell growth medium; and (iii) a buffer.

238. The method of embodiment 237, wherein the cell line is selected from a permissive cell line and a semi-permissive cell line.

239. A kit for diagnosing a viral disease in a patient comprising:

(a) a reagent for carrying out amplification of a nucleic acid sequence;

(b) a primer comprising a sequence complementary to a sequence in one strand of the viral genome; and (c) a primer comprising a sequence identical to a sequence in said strand of the viral genome, wherein said primers are capable of amplifying a nucleic acid of said virus when said nucleic acid is present.

240. The kit of embodiment 239, wherein said reagent is for carrying out PCR.

241. The kit of embodiment 240 wherein said reagent is for detection in real time.

242. The kit of 239, wherein said reagent is selected from a Taqman probe, a molecular beacon, a yin-yang probe set, an energy transfer labeled primer, an energy transfer labeled probe, an energy transfer labeled nucleotide, an intercalating dye and a combination thereof.

243. The kit of embodiment 239 wherein said reagent is for carrying out in situ PCR.

244. The kit of embodiment 237 wherein said reagent is appropriate for carrying out an isothermal amplification reaction.

245. The kit of embodiment 244, wherein said amplification reaction is selected from SDA reaction, a 3SR reaction, a NASBA reaction, a TMA reaction, a LAMP reaction, an HAD reaction, a LAMP reaction, stem-loop amplification, a SMART reaction, an IMDA reaction, a SPIA reaction, and a cHDA reaction.

246. The kit of any one of embodiments 225, 230 and 232 and 239, wherein the virus is Herpesvirus saimiri and the disease is idiopathic pulmonary fibrosis, a lymphoproliferative disease or cancer.

247. A method of diagnosing or prognosticating a viral disease in a patient comprising a step of detecting the presence of a virus-specific element from a virus in a clinical sample from said patient.

248. The method of embodiment 246, wherein the virus-specific element is a nucleic acid selected from mRNA and DNA.

249. The method of embodiment 248, wherein said clinical sample is selected from whole blood, serum, tissue, lavage and combinations thereof.

250. The method of embodiment 248, further comprising a step of amplifying said nucleic acid prior to said detecting step by PCR or RT-PCR.

251. The method of embodiment 248, wherein the virus is Herpesvirus saimiri or a related virus.

252. The method of embodiment 248, wherein the viral disease is idiopathic pulmonary fibrosis.

253. The method of embodiment 247, wherein the virus-specific element is a protein or peptide.

254. The method of embodiment 253, wherein said detecting step is carried out using an antibody to said virus-specific protein or peptide.

255. A method of identifying in vitro a therapeutic agent for the treatment of a viral disease, comprising the steps of
(a) exposing a virus culture to said agent;
(b) measuring the propagation of said virus culture; and
(c) comparing said propagation measured in step (b) with the propagation of a virus culture that has not been exposed to the agent,
wherein propagation measured in step (b) that is lower than propagation of a virus culture that has not been exposed to the agent identifies a therapeutic agent for the treatment of said viral disease.

256. The method of embodiment 255, wherein the virus is cultured in a permissive cell line, a semi-permissive cell line or human T-lymphocytes.

257. The method of embodiment 255, wherein viral propagation is measured by measuring an amount of viral particles.

258. The method of embodiment 255, wherein viral propagation is measured by measuring an amount of infected host cells.

259. A method of treating a patient suffering from a viral disease comprising administering to the patient an effective amount of an agent that inhibits replication of a virus, an effective amount of an agent that down-regulates expression of a virus-specific protein, an antagonist of a viral protein or a neutralizing agent that blocks activity of a viral protein.

260. The method of embodiment 259, wherein the antagonist is an antibody to virus-specific IL-17.

261. A kit for diagnosing a viral disease in a patient comprising:
(a) a reagent for carrying out amplification of a nucleic acid sequence;
(b) a primer comprising a sequence complementary to a sequence in one strand of the viral genome; and
(c) a primer comprising a sequence identical to a sequence in said strand of the viral genome,
wherein said primers are capable of amplifying a nucleic acid of said virus when said nucleic acid is present.

262. The kit of embodiment 261, wherein said reagent is for carrying out PCR.

263. The kit of embodiment 262 wherein said reagent is for detection in real time.

264. The kit of embodiment 262, wherein said reagent is selected from a Taqman probe, a molecular beacon, a yin-yang probe set, an energy transfer labeled primer, an energy transfer labeled probe, an energy transfer labeled nucleotide, an intercalating dye and a combination thereof.

265. The kit of embodiment 262, wherein the virus is Herpesvirus saimiri and the disease is idiopathic pulmonary fibrosis.

266. A method of detecting the presence of viral target sequences in a human clinical sample comprising the steps of:
a. providing
 i. a human clinical sample suspected of having a viral infection,
 ii. a labeled nucleic acid probe comprising one or more sequences derived from Herpesvirus saimiri,
b. contacting said clinical sample (i) with said labeled nucleic acid probe (ii),
c. allowing hybridization to take place between said labeled nucleic acid probe (ii) and nucleic acids with viral sequences in said clinical sample (i) if present, and
d. detecting hybridization of said nucleic acid probe (ii) to nucleic acids in said clinical sample (i).

267. The method of embodiment 266, wherein said viral target sequences comprises mRNA.

268. The method of embodiment 266, wherein said viral target sequences comprises DNA.

269. The method of embodiment 266, wherein said nucleic acid probe is labeled with a radioactive label, a fluorescent label, a chemiluminescent label, a hapten label, an enzymatic label, a labeled binding partner label, a chromogenic label, or an energy transfer pair.

270. The method of embodiment 269, wherein said labeled binding partner is biotin, avidin or streptavidin.

271. The method of embodiment 266, wherein said human clinical sample is selected from blood, tissue, lavage, and combinations thereof.

272. The method of embodiment 271, wherein said tissue sample is a lung biopsy.

273. The method of embodiment 271, wherein said clinical sample comprises a paraffin embedded slide.

274. The method of embodiment 266, wherein said method of detection comprises in situ hybridization or flow cytometry.

275. The method of embodiment 266, wherein said providing step comprises isolation of nucleic acids from said clinical sample.

276. The method of embodiment 275, further comprising a nucleic acid amplification step before or concurrently with step b.

277. The method of embodiment 276, wherein said amplification step is carried out by an Eberwine amplification, a polymerase chain reaction (PCR) amplification, an AmpiProbe® amplification, a real time polymerase chain reaction (RT-PCR) amplification, a degenerate oligonucleotide primer PCR (DOP-PCR) amplification, a multiple displacement amplification, a self-sustained sequence reaction (3SR) amplification, a nucleic acid based transcription assay (NASBA) amplification, a transcription mediated amplification (TMA), a strand displacement amplification (SDA), a helicase-dependent amplification (HDA), a loop-mediated isothermal amplification (LAMP), a stem-loop amplification, a signal mediated amplification of RNA technology (SMART), an isothermal multiple displacement amplification (IMDA), a single primer isothermal amplification (SPIA), or a circular helicase-dependent amplification (cHDA).
278. The method of embodiment 276 or embodiment 277, wherein said detection is carried out in a dot blot format, a slot blot format, a microarray format, a sandwich assay format, a primer extension format, or fluorescence resonance energy transfer (FRET).
279. The method of embodiment 266, wherein said hybridization is carried out under conditions where said labeled probe hybridizes with a viral sequence that is at least 50% homologous with said labeled nucleic acid probe sequence.
280. The method of embodiment 279, wherein said hybridization is carried out under conditions where said labeled probe hybridizes with a viral sequence that is at least 75% homologous with said labeled nucleic acid probe sequence.
281. The method of embodiment 280, wherein said hybridization is carried out under conditions where said labeled probe hybridizes with a viral sequence that is at least 90% homologous with said labeled nucleic acid probe sequence.
282. The method of embodiment 266, wherein said labeled nucleic acid probe comprises one or more sequences derived from Herpesvirus saimiri A, Herpesvirus saimiri B or Herpesvirus saimiri C.
283. A method of detecting the presence of viral target sequences in a human clinical sample comprising the steps of:
 a. providing
  i. a human clinical sample suspected of containing nucleic acids comprising viral target sequences,
  ii. a labeled nucleic acid probe comprising one or more sequences derived from a virus related to Herpesvirus saimiri, wherein said related virus has at least 50% nucleic acid sequence homology with Herpesvirus saimiri,
 b. contacting said clinical sample (i) with said labeled nucleic acid probe (ii),
 c. allowing hybridization to take place between said labeled nucleic acid probe (ii) and nucleic acids with viral sequences in said clinical sample (i) if said viral target sequence nucleic acids are present, and
 d. detecting hybridization of said nucleic acid probe (ii) to nucleic acids in said clinical sample (i).
284. The method of embodiment 283, wherein said hybridization is carried out under conditions where said labeled probe hybridizes with a viral sequence that is at least 75% homologous with said labeled nucleic acid probe sequence.
285. The method of embodiment 284, wherein said hybridization is carried out under conditions where said labeled probe hybridizes with a viral sequence that is at least 90% homologous with said labeled nucleic acid probe sequence.
286. The method of embodiment 283, wherein said viral target sequence comprises mRNA.
287. The method of embodiment 283, wherein said viral target sequence comprises DNA.
288. The method of embodiment 283, wherein said nucleic acid probe is labeled with a is a radioactive label, a fluorescent label, a chemiluminescent label, a hapten label, an enzymatic label, a labeled binding partner label, a chromogenic label, or an energy transfer pair.
289. The method of embodiment 288, wherein said labeled binding partner is biotin, avidin or streptavidin.
290. The method of embodiment 283, wherein said nucleic acid probe comprises a nucleotide analogue.
291. The method of embodiment 283, wherein said human clinical sample is selected from blood, tissue, lavage, and combinations thereof.
292. The method of embodiment 291, wherein said tissue sample is a lung biopsy.
293. The method of embodiment 291, wherein said clinical sample comprises a paraffin embedded slide.
294. The method of embodiment 283, wherein said method of detection comprises in situ hybridization or flow cytometry.
295. The method of embodiment 283, wherein said providing step comprises isolation of nucleic acids from said clinical sample.
296. The method of embodiment 295, further comprising a nucleic acid amplification step.
297. The method of embodiment 296, wherein said amplification step is carried out by an Eberwine amplification, a polymerase chain reaction (PCR) amplification, an AmpiProbe® amplification, a real time polymerase chain reaction (RT-PCR) amplification, a degenerate oligonucletotide primer PCR (DOP-PCR) amplification, a multiple displacement amplification, a self-sustained sequence reaction (3SR) amplification, a nucleic acid based transcription assay (NASBA) amplification, a transcription mediated amplification (TMA), a strand displacement amplification (SDA), a helicase-dependent amplification (HDA), a loop-mediated isothermal amplification (LAMP), a stem-loop amplification, a signal mediated amplification of RNA technology (SMART), an isothermal multiple displacement amplification (IMDA), a single primer isothermal amplification (SPIA), or a circular helicase-dependent amplification (cHDA).
298. The method of embodiment 296 or embodiment 297, wherein said detection is carried out by gel electrophoresis, in a dot blot format, a slot blot format, a microarray format, a sandwich assay format, a primer extension format, fluorescence resonance energy transfer (FRET) or by fluorescence derived from intercalation of a dye.
299. The method of embodiment 283, wherein said labeled nucleic acid probe comprises one or more sequences derived from Herpesvirus saimiri A, Herpesvirus saimiri B or Herpesvirus saimiri C.
300. A method of diagnosing idiopathic pulmonary fibrosis in a human patient comprising the steps of:
 a. providing
  i. a human clinical sample suspected of having idiopathic pulmonary fibrosis,
  ii. a labeled nucleic acid probe comprising one or more sequences derived from Herpesvirus saimiri or a virus related to Herpesvirus saimiri, wherein said related virus has at least 50% nucleic acid sequence homology with Herpesvirus saimiri,
 b. contacting said clinical sample (i) with said labeled nucleic acid probe (ii),
 c. allowing hybridization to take place between said labeled nucleic acid probe (ii) and viral sequences in said clinical sample (i) if present, and d. detecting hybridization of said nucleic acid probe (ii) to said viral sequences in the clinical sample (i), and thereby diagnosing said patient as having idiopathic pulmonary fibrosis.

301. The method of embodiment 300, wherein said viral sequences comprise mRNA.
302. The method of embodiment 300, wherein said viral sequences comprise DNA.
303. The method of embodiment 300, wherein said nucleic acid probe is labeled with a radioactive label, a fluorescent label, a chemiluminescent label, a hapten label, an enzymatic label, a labeled binding partner label, a chromogenic label, or an energy transfer pair.
304. The method of embodiment 303, wherein said labeled binding partner is biotin, avidin or streptavidin.
305. The method of embodiment 303, wherein said nucleic acid probe comprises a nucleotide analogue.
306. The method of embodiment 300, wherein said human clinical sample is selected from blood, tissue, lavage, and combinations thereof.
307. The method of embodiment 306, wherein said tissue sample is a lung biopsy.
308. The method of embodiment 307, wherein said clinical sample comprises a paraffin embedded slide.
309. The method of embodiment 300, wherein said method of detection comprises in situ hybridization or flow cytometry.
310. The method of embodiment 300, wherein said providing step comprises isolation of nucleic acids from said clinical sample.
311. The method of embodiment 310, further comprising a nucleic acid amplification step.
312. The method of embodiment 310, wherein said amplification step is carried out by an Eberwine amplification, a polymerase chain reaction (PCR) amplification, an AmpiProbe® amplification, a real time polymerase chain reaction (RT-PCR) amplification, a degenerate oligonucletotide primer PCR (DOP-PCR) amplification, a multiple displacement amplification, a self-sustained sequence reaction (3SR) amplification, a nucleic acid based transcription assay (NASBA) amplification, a transcription mediated amplification (TMA), a strand displacement amplification (SDA), a helicase-dependent amplification (HDA), a loop-mediated isothermal amplification (LAMP), a stem-loop amplification, a signal mediated amplification of RNA technology (SMART), an isothermal multiple displacement amplification (IMDA), a single primer isothermal amplification (SPIA), or a circular helicase-dependent amplification (cHDA).
313. The method of embodiment 311 or embodiment 312, wherein said detection is carried out in a dot blot format, a slot blot format, a microarray format, a sandwich assay format, a primer extension format, or fluorescence resonance energy transfer (FRET).
314. The method of embodiment 300, wherein said hybridization is carried out under conditions where said labeled probe hybridizes with a viral sequence that is at least 75% homologous with said labeled nucleic acid probe sequence.
315. The method of embodiment 314, wherein said hybridization is carried out under conditions where said labeled probe hybridizes with a viral sequence that is at least 90% homologous with said labeled nucleic acid probe sequence.
316. The method of embodiment 300, wherein said labeled nucleic acid probe comprises one or more sequences derived from Herpesvirus saimiri A, Herpesvirus saimiri B or Herpesvirus saimiri C.
317. A method of diagnosing idiopathic pulmonary fibrosis in a human patient comprising the steps of:
a. providing
i. a human clinical sample suspected of having a viral infection,
ii. antibodies to at least two protein targets selected from DHFR, cyclin D, IL-17 and thymidylate synthase;
b. contacting said clinical sample (i) with said antibodies (ii),
c. allowing binding to take place between said antibodies (ii) and proteins in said clinical sample (i) if present, and
d. detecting binding of said antibodies (ii) and proteins in said clinical sample, if present, (i), and
thereby diagnosing said patient as having idiopathic pulmonary fibrosis.
318. The method of embodiment 317, wherein said antibodies (ii) are labeled.
319. The method of embodiment 317, wherein said antibodies (ii) are detected by binding labeled secondary antibodies to said antibodies (ii).
320. The method of embodiment 318 or embodiment 319, wherein said label is a radioactive label, a fluorescent label, a chemiluminescent label, a hapten label, an enzymatic label, a labeled binding partner label, a chromogenic label, or an energy transfer pair.
321. The method of embodiment 317, wherein said antibodies are monoclonal antibodies, polyclonal antibodies or combinations thereof.
322. The method of embodiment 321, wherein said antibodies are polyclonal antibodies.
323. The method of embodiment 317, wherein said antibodies are human antibodies, humanized antibodies or combinations thereof.
324. A method of diagnosing idiopathic pulmonary fibrosis in a human subject comprising the steps of
a. providing
i. a clinical sample from a subject who may have idiopathic pulmonary fibrosis,
ii. one or more antibodies to viral proteins expressed by Herpesvirus saimiri or a virus related to Herpesvirus saimiri, wherein said related virus has as at least 50% nucleic acid homology with Herpesvirus saimiri
b. contacting said clinical sample (i) with said one or more antibodies (ii),
c. allowing binding to take place between said one or more antibodies (ii) and said clinical sample (i), and
d. detecting the binding of said one or more antibodies (ii) to said viral proteins in said clinical sample (i) and thereby diagnosing said subject as having idiopathic pulmonary fibrosis.
325. The method of embodiment 324 wherein one of said viral proteins is IL-17.
326. The method of embodiment 324 wherein one of said viral proteins is DHFR.
327. The method of embodiment 324 wherein one of said viral proteins is cyclin D.
328. The method of embodiment 324 wherein one of said viral proteins is thymidylate synthase.
329. The method of embodiment 324 wherein one of said viral proteins is a viral capsid protein.
330. A method of treating idiopathic pulmonary fibrosis in a subject comprising administering to said subject, one or more antibodies to one or more viral proteins expressed by Herpesvirus saimiri or a virus related to Herpesvirus saimiri wherein said related virus has at least 50% nucleic acid homology with Herpesvirus saimiri.

331. The method of embodiment 330 wherein one of said viral proteins is IL-17.
332. The method of embodiment 300 wherein one of said viral proteins is DHFR.
333. The method of embodiment 300 wherein one of said viral proteins is cyclin D.
334. The method of embodiment 330 wherein one of said viral proteins is thymidylate synthase.
335. The method of embodiment 300 wherein one of said viral proteins is a viral capsid protein.
336. A method of preventing idiopathic pulmonary fibrosis in a subject comprising administering to said subject one or more antibodies to one or more proteins expressed by Herpesvirus saimiri or a virus related to Herpesvirus saimiri wherein said related virus has as at least 50% nucleic acid homology with Herpesvirus saimiri.
337. The method of embodiment 336 wherein one of said viral proteins is IL-17.

338. The method of embodiment 336 wherein one of said viral proteins is DHFR.

339. The method of embodiment 336 wherein one of said viral proteins is cyclin D.

340. The method of embodiment 336 wherein one of said viral proteins is thymidylate synthase.

341. The method of embodiment 336 wherein one of said viral proteins is a viral capsid protein.

342. A kit for detection of viral target sequences in a human clinical sample comprising:

a. a labeled nucleic acid probe selected from (i) a probe comprising one or more sequences derived from Herpesvirus saimiri, (ii) a probe derived from a virus related to Herpesvirus saimiri, wherein said related virus has at least 50% nucleic acid sequence homology with Herpesvirus saimiri, or a combination of (i) and (ii); and b. reagents for carrying out hybridization of said probe to nucleic acids in the clinical sample.

343. The kit of embodiment 342, further comprising reagents for isolating said viral target sequences.

344. The kit of embodiment 342 or embodiment 343, further comprising a. a primer comprising a sequence complementary to a sequence in one strand of the viral target sequence;

b. a primer comprising a sequence identical to a sequence in said strand of the viral target sequence; and c. a reagent for carrying out amplification of said viral target sequence.

345. The kit of embodiment 342, further comprising a nucleic acid probe that is complementary to a viral target sequence.

346. The kit of embodiment 342, further comprising an intercalator that increases fluorescence after binding to double-stranded DNA.

347. The kit of embodiment 345 or embodiment 346, wherein at least one primer or probe is labeled.

348. A method of detecting the presence of viral target sequences in a human clinical sample comprising the steps of a. providing a human clinical sample that may contain virally infected cells, b. means for isolating nucleic acids from said clinical sample, c. means for amplification of nucleic acids in said sample, wherein said means are capable of amplifying nucleic acids of Herpesvirus saimiri or a virus related to Herpesvirus saimiri wherein said related virus has at least 50% nucleic acid homology with Herpesvirus saimiri when said sample comprises nucleic acids of Herpesvirus saimiri or said related virus, d. isolating nucleic acids from said clinical sample by said means (ii), e. combining said isolated nucleic acids with said amplification means (iii), f. amplifying said nucleic acids from Herpesvirus saimiri or said related virus, and g. detecting the amplification of said nucleic acids of Herpesvirus saimiri or said related virus, thereby detecting the presence of said viral target sequences.

349. The embodiment of claim 348, wherein said means for amplification includes reagents for performing an Eberwine amplification, a polymerase chain reaction (PCR) amplification, an AmpiProbe® amplification, a real time polymerase chain reaction (RT-PCR) amplification, a degenerate oligonucleotide primer PCR (DOP-PCR) amplification, a multiple displacement amplification, a self-sustained sequence reaction (3SR) amplification, a nucleic acid based transcription assay (NASBA) amplification, a transcription mediated amplification (TMA), a strand displacement amplification (SDA), a helicase-dependent amplification (HDA), a loop-mediated isothermal amplification (LAMP), a stem-loop amplification, a signal mediated amplification of RNA technology (SMART), an isothermal multiple displacement amplification (IMDA), a single primer isothermal amplification (SPIA), or a circular helicase-dependent amplification (cHDA).The method of claim 348, wherein said detecting step (vii) is carried out using labeled nucleotides, a labeled primer, a labeled probe, an intercalating dye or a combination thereof.

350. The method of embodiment 348, wherein said detecting step (g) is carried out using one or more labeled nucleotides, one or more labeled primers, one or more labeled probes, one or more intercalating dyes or a combination thereof.

351. A kit for detecting at least two protein targets selected from DHFR, cyclin D, IL-17 and thymidylate synthase in a human clinical sample comprising:

a. an antibody to any two of DHFR, cyclin D, IL-17 and thymidilyate synthase; and b. reagents for the binding of said antibodies to proteins in said sample.

352. The kit of embodiment 351, wherein said antibodies are monoclonal antibodies, polyclonal antibodies, or combinations thereof.

353. The kit of embodiment 351, wherein said antibody is labeled.

354. The kit of embodiment 351, further comprising a secondary antibody.

355. The kit of embodiment 354, wherein the secondary antibody is labeled.

356. The kit of embodiment 351, wherein the secondary antibody is conjugated to an enzyme.

357. The kit of claim 356, further comprising reagents for signal amplification, wherein said signal amplification.

358. A composition comprising a viral target sequence hybridized to (i) a non-radioactively labeled nucleic acid comprising one or more sequences derived from Herpesvirus saimiri, (ii) a non-radioactively labeled nucleic acid comprising one or more sequences derived from a virus related to Herpesvirus saimiri, wherein said related virus has at least 50% nucleic acid sequence homology with Herpesvirus saimiri, or a combination thereof, wherein said hybridization product is in a human cell of a clinical sample.

359. A method of diagnosing idiopathic pulmonary fibrosis in a human patient comprising the steps of:

a. providing
 i. a human clinical sample suspected of having a viral infection,
 ii. an antibody to viral IL-17,
b. contacting said clinical sample (i) with said antibody (ii),
c. allowing binding to take place between said antibody (ii) and proteins in said clinical sample (i) if present, and
d. detecting binding of said antibody (ii) to said viral IL-17 in said clinical sample (i), and thereby diagnosing said patient as having idiopathic pulmonary fibrosis.

360. A method of diagnosing Castleman's disease, a lymphoma, a thymoma and a sarcoma in a human patient comprising the steps of:

a. providing
 i. a human clinical sample suspected of having Castleman's disease, a lymphoma, a thymoma and a sarcoma,
 ii. a labeled nucleic acid probe comprising one or more sequences derived from Herpesvirus saimiri,
b. contacting said clinical sample (i) with said labeled nucleic acid probe (ii),
c. allowing hybridization to take place between said labeled nucleic acid probe (ii) and viral sequences in said clinical sample (i) if present, and
d. detecting hybridization of said nucleic acid probe (ii) to said viral sequences in said clinical sample (i), and thereby diagnosing said patient as Castleman's disease, a lymphoma, a thymoma or a sarcoma.

361. The method of embodiment 360, wherein said viral sequences comprise mRNA.

362. The method of embodiment 360, wherein said viral sequences comprise DNA.

363. The method of embodiment 360, wherein said viral sequences comprise U rich non-coding RNA.

364. The method of embodiment 360, wherein said nucleic acid probe is labeled with a radioactive label, a fluorescent label, a chemiluminescent label, a hapten label, an enzymatic label, a labeled binding partner label, a chromogenic label, or an energy transfer pair.

365. The method of embodiment 364, wherein said labeled binding partner is biotin, avidin or streptavidin.

366. The method of embodiment 360, wherein said nucleic acid probe comprises a nucleotide analogue.

367. The method of embodiment 360, wherein said human clinical sample is selected from blood, tissue, and combinations thereof 368. The method of embodiment 367, wherein said clinical sample comprises a paraffin embedded slide.

369. The method of embodiment 360, wherein said method of detection comprises in situ hybridization or flow cytometry.

370. The method of embodiment 360, wherein said providing step comprises isolation of nucleic acids from said clinical sample.

371. The method of embodiment 360, further comprising a nucleic acid amplification step.

372. The method of embodiment 360, wherein said amplification step is carried out by an Eberwine amplification, a polymerase chain reaction (PCR) amplification, an AmpiProbe® amplification, a real time polymerase chain reaction (RT-PCR) amplification, a degenerate oligonucletotide primer PCR (DOP-PCR) amplification, a multiple displacement amplification, a self-sustained sequence reaction (3SR) amplification, a nucleic acid based transcription assay (NASBA) amplification, a transcription mediated amplification (TMA), a strand displacement amplification (SDA), a helicase-dependent amplification (HDA), a loop-mediated isothermal amplification (LAMP), a stem-loop amplification, a signal mediated amplification of RNA technology (SMART), an isothermal multiple displacement amplification (IMDA), a single primer isothermal amplification (SPIA), or a circular helicase-dependent amplification (cHDA).

373. The method of embodiment 371 or embodiment 372, wherein said detection is carried out in a dot blot format, a slot blot format, a microarray format, a sandwich assay format, a primer extension format, or fluorescence resonance energy transfer (FRET).

374. The method of embodiment 360, wherein said hybridization is carried out under conditions where said labeled probe hybridizes with a viral sequence that is at least 75% homologous with said labeled nucleic acid probe sequence.

375. The method of embodiment 374, wherein said hybridization is carried out under conditions where said labeled probe hybridizes with a viral sequence that is at least 90% homologous with said labeled nucleic acid probe sequence.

376. The method of embodiment 360, wherein said labeled nucleic acid probe comprises one or more sequences derived from Herpesvirus saimiri A, Herpesvirus saimiri B or Herpesvirus saimiri C.

377. A method of diagnosing Castleman's disease, a lymphoma, a thyoma and a sarcoma in a human patient comprising the steps of:

a. providing
 i. a human clinical sample suspected of having Castleman's disease, a lymphoma, a thyoma and a sarcoma,
 ii. a labeled nucleic acid probe comprising one or more sequences derived from a virus related to Herpesvirus saimiri, wherein said related virus has at least 50% nucleic acid sequence homology with Herpesvirus saimiri,
b. contacting said clinical sample (i) with said labeled nucleic acid probe (ii),
c. allowing hybridization to take place between said labeled nucleic acid probe (ii) and viral sequences in said clinical sample (i) if present, and
d. detecting hybridization of said nucleic acid probe (ii) to said viral sequences in said clinical sample (i), and thereby diagnosing said patient as Castleman's disease, a lymphoma, a thymoma or a sarcoma.

378. The method of embodiment 377, wherein said hybridization is carried out under conditions where said labeled probe hybridizes with a viral sequence that is at least 75% homologous with said labeled nucleic acid probe sequence.
379. The method of embodiment 378, wherein said hybridization is carried out under conditions where said labeled probe hybridizes with a viral sequence that is at least 90% homologous with said labeled nucleic acid probe sequence.
380. The method of embodiment 377, wherein said viral sequences comprise mRNA.
381. The method of embodiment 377, wherein said viral sequences comprise DNA.
382. The method of embodiment 377, wherein said viral sequences comprise U rich non-coding RNA.
383. The method of embodiment 377, wherein said nucleic acid probe is labeled with a radioactive label, a fluorescent label, a chemiluminescent label, a hapten label, an enzymatic label, a labeled binding partner label, a chromogenic label, or an energy transfer pair.
384. The method of embodiment 383, wherein said labeled binding partner is biotin, avidin or streptavidin.
385. The method of embodiment 377, wherein said nucleic acid probe comprises a nucleotide analogue.
386. The method of embodiment 377, wherein said human clinical sample is selected from blood, tissue, and combinations thereof.
387. The method of embodiment 386, wherein said clinical sample comprises a paraffin embedded slide.
388. The method of embodiment 377, wherein said method of detection comprises in situ hybridization or flow cytometry.
389. The method of embodiment 377, wherein said providing step comprises isolation of nucleic acids from said clinical sample.
390. The method of embodiment 389, further comprising a nucleic acid amplification step.
391. The method of embodiment 390, wherein said amplification step comprises an Eberwine amplification, a polymerase chain reaction (PCR) amplification, an AmpiProbe® amplification, a real time polymerase chain reaction (RT-PCR) amplification, a degenerate oligonucletotide primer PCR (DOP-PCR) amplification, a multiple displacement amplification, a self-sustained sequence reaction (3SR) amplification, a nucleic acid based transcription assay (NASBA) amplification, a transcription mediated amplification (TMA), a strand displacement amplification (SDA), a helicase-dependent amplification (HDA), a loop-mediated isothermal amplification (LAMP), a stem-loop amplification, a signal mediated amplification of RNA technology (SMART), an isothermal multiple displacement amplification (IMDA), a single primer isothermal amplification (SPIA), or a circular helicase-dependent amplification (cHDA).
392. The method of embodiment 390 or embodiment 391, wherein said detection is carried out in a dot blot format, a slot blot format, a microarray format, a sandwich assay format, a primer extension format, or fluorescence resonance energy transfer (FRET).
393. A kit for detection of viral target sequences in a human clinical sample comprising:
a. a labeled nucleic acid probe selected from (i) a non-radioactively labeled probe comprising one or more sequences derived from Herpesvirus saimiri, (ii) a probe derived from a virus related to Herpesvirus saimiri, wherein said related virus has at least 50% nucleic acid sequence homology with Herpesvirus saimiri, or a combination of (i) and (ii); and
b. reagents for carrying out hybridization of said probe to a clinical sample.
394. The kit of embodiment 393, further comprising reagents for isolating said viral target sequences.
395. A kit comprising:
a. a labeled nucleic acid probe selected from (i) a non-radioactively labeled probe comprising one or more sequences derived from Herpesvirus saimiri, (ii) a probe derived from a virus related to Herpesvirus saimiri, wherein said related virus has at least 50% nucleic acid sequence homology with Herpesvirus saimiri, or a combination of (i) and (ii);
b. reagents for carrying out hybridization of said probe to a clinical sample,
c. a primer comprising a sequence complementary to a sequence in one strand of the viral target sequence;
d. a primer comprising a sequence identical to a sequence in said strand of the viral target sequence; and
e. a reagent for carrying out amplification of said viral target sequence.
396. A method of diagnosing Castleman's disease, a lymphoma, a thymoma and a sarcoma in a human patient in a human patient comprising the steps of:
a. providing
 i. a human clinical sample suspected of having a viral infection,
 ii. antibodies to at least two protein targets selected from DHFR, cyclin D, IL-17 and thymidylate synthase;
b. contacting said clinical sample (i) with said antibodies (ii),
c. allowing binding to take place between said antibodies (ii) and proteins in said clinical sample (i) if present, and
d. detecting binding of said antibodies (ii) to said proteins in said clinical sample (i), and
thereby diagnosing said patient as having idiopathic pulmonary fibrosis.
397. The method of embodiment 396, wherein said antibodies (ii) are labeled.
398. The method of embodiment 396, wherein said antibodies (ii) are detected by binding labeled secondary antibodies to said antibodies (ii).
399. The method of embodiment 397 or embodiment 398, wherein said label is a radioactive label, a fluorescent label, a chemiluminescent label, a hapten label, an enzymatic label, a labeled binding partner label, a chromogenic label, or an energy transfer pair.
400. The method of embodiment 396, wherein said antibodies are monoclonal antibodies, polyclonal antibodies or combinations thereof.
401. The method of embodiment 400, wherein said antibodies are polyclonal antibodies.
402. The method of embodiment 400, wherein said antibodies are human antibodies, humanized antibodies or combinations thereof.
403. A method of isolating a clone comprising a gamma Herpesvirus sequence comprising the steps of
a. providing
 i. a biological sample from a subject who has idiopathic pulmonary fibrosis, idiopathic Castleman's disease, a retroperitoneal liposarcoma, a thymoma or a mediastinal lymphoma,
 ii. reagents for isolating gamma Herpesvirus nucleic acids from said biological sample, iii. reagents for creating a clone library of said isolated nucleic acids,
iv. a nucleic acid probe or probes comprising one or more gamma Herpesvirus sequences,
b. isolating gamma Herpesvirus nucleic acids from said biological sample;
c. creating a clone library of nucleic acid constructs from said isolated gamma Herpesvirus nucleic acids,
d. hybridizing said nucleic acid probe or probes (iv),
e. screening said clone library (c) to identify a clone that comprises nucleic acids having homology with said nucleic acid probe or probes (c1), and
f. isolating said clone identified in step e.

404. The method of embodiment 403, wherein said nucleic acids from said biological sample are DNA.

405. The method of embodiment 403, wherein said nucleic acids from said biological sample are RNA.

406. The method of embodiment 403 wherein said probe or probes comprises a Herpesvirus saimiri STP sequence, a Herpesvirus saimiri Terminal Repeat sequence, a Herpesvirus saimiri IL-17 sequence, a Herpesvirus saimiri DNA polymerase sequence, Herpesvirus saimiri cyclin D sequence, a Herpesvirus saimiri IL-17 sequence, a Herpesvirus saimiri glycoprotein B sequence, a Herpesvirus saimiri terminase sequence, or any combination thereof.

407. The method of embodiment 403, further comprising a step of carrying out subtractive hybridization step prior to step c.

408. The method of embodiment 403, further comprising a step of carrying out positive selection step prior to step c.

409. The method of embodiment 403, further comprising a step of enriching episomal DNA apart from chromosomal DNA prior to step c.

410. The method of embodiment 403, further comprising after step e. the steps of f. obtaining the nucleic acid sequence of said gamma Herpesvirus clone; and g. comparing the sequence of said clone to the sequence of Herpesvirus saimiri.

411. The method of embodiment 410, further comprising after step g. a step of h. synthesizing nucleic acids using said gamma Herpesvirus DNA sequence.

412. The method of embodiment 411, further comprising after step h. a step of i. labeling said synthesized nucleic acids.

413. The method of embodiment 403, further comprising after step e. the steps of f. isolating said nucleic acid construct from said clone and g. labeling the nucleic acids of said construct.

414. The method of embodiment 412 or embodiment 413, wherein said nucleic acid construct has a phage promoter, and said method further comprises a step of isolating said nucleic acid construct from said clone, and a step of carrying out an RNA transcription step with said construct as a template.

415. The method of embodiment 414, wherein said transcripts are labeled during said transcription step.

416. The method of embodiment 413 or embodiment 415, wherein said label is a non-radioactive label selected from a fluorescent label, a chemiluminescent label, a hapten label, a chromogenic label, or an energy transfer pair.

417. A method of isolating a nucleic acid comprising a gamma Herpesvirus sequence comprising the steps of:
a. providing
i. biological sample from a subject who has idiopathic pulmonary fibrosis, idiopathic Castleman's disease, a retroperitoneal liposarcoma, a thymoma or a mediastinal lymphoma,
ii. a reagent for isolating nucleic acids from said biological sample,
iii. nucleic acid primers that are capable of amplifying multiple gamma Herpesvirus species in a PCR reaction, and
iv. reagents for carrying out a PCR reaction,
b. isolating nucleic acids from said biological sample,
c. mixing said nucleic acid primers, and said PCR reagent with said biological sample,
d. carrying out a PCR reaction,
e. analyzing said PCR reaction, and
f. identifying the presence of an amplification product.

418. The method of embodiment 417, wherein said nucleic acids from said biological sample are DNA.

419. The method of embodiment 417, wherein said nucleic acids from said biological sample are RNA.

420. The method of embodiment 417, wherein said nucleic acid primers amplify a gamma Herpesvirus DNA polymerase gene, a gamma Herpesvirus glycoprotein B gene, a gamma Herpesvirus terminase gene or a combination thereof.

421. The method of embodiment 417, further comprising a step of carrying out subtractive hybridization step prior to step c.

422. The method of embodiment 417, further comprising a step of carrying out positive selection prior to step c.

423. The method of embodiment 417, further comprising a step of enriching episomal DNA apart from chromosomal DNA prior to step c.

424. The method of embodiment 417, further comprising the steps g. of obtaining the nucleic acid sequence of said nucleic acid comprising a gamma Herpesvirus sequence, and h. comparing the sequence of said clone to the sequence of Herpesvirus saimiri after step f.

425. The method of embodiment 424 further comprising a step of i. synthesizing nucleic acids using the DNA sequence of said gamma Herpesvirus clone.

426. The method of embodiment 425, further comprising the steps of j. generating a nucleic acid construct using the DNA sequence of said gamma Herpesvirus clone; and k. transfecting cells to obtain a clone of said gamma Herpesvirus DNA sequence.

427. The method of embodiment 417, further comprising the steps of generating of a nucleic acid construct from said PCR products and transfecting cells to obtain a clone of said PCR product after step f.

428. The method of embodiment 425, wherein the synthesized nucleic acid comprises at least one non-radioactive label selected from a fluorescent label, a chemiluminescent label, a hapten label, a chromogenic label, or an energy transfer pair.

429. The method of embodiment 426, further comprising the steps isolating said construct from said clone and labeling the nucleic acids of said construct.

430. The method of embodiment 427, further comprising the steps isolating said construct from said clone and labeling the nucleic acids of said construct.

431. The method of embodiment 426 or embodiment 427, wherein said construct has a phage promoter, and said method further comprises the steps of isolating said construct from said clone and carrying out an RNA transcription step with said clone as a template.

432. The method of embodiment 431 where said transcripts are labeled during said transcription step.
433. A clone comprising DNA sequences from a gamma Herpesvirus DNA produced by the method of embodiment 403.
434. A clone comprising DNA sequences from a gamma Herpesvirus produced by the method of embodiment 427.
435. A clone comprising DNA sequences from a gamma Herpesvirus produced by the method of embodiment 428.
436. A method for diagnosing idiopathic pulmonary fibrosis, idiopathic Castleman's disease, a retroperitoneal liposarcoma, a thymoma or a mediastinal lymphoma in a subject comprising
a. providing
  i. a human clinical sample suspected of having idiopathic pulmonary fibrosis, Castleman's disease, a lymphoma, a thymoma and a sarcoma,
  ii. a labeled nucleic acid probe of embodiment 412, 413, 433, 434 or 435,
b. contacting said clinical sample (i) with said labeled nucleic acid probe (ii),
c. allowing hybridization to take place between said labeled nucleic acid probe (ii) and viral sequences in said clinical sample (i) if present, and
d. detecting hybridization of said nucleic acid probe (ii) to said viral sequences in said clinical sample (i), and
thereby diagnosing said patient as having idiopathic pulmonary fibrosis, Castleman's disease, a lymphoma, a thymoma or a sarcoma.
437. A method of diagnosing idiopathic pulmonary fibrosis, idiopathic Castleman's disease, a retroperitoneal liposarcoma, a thymoma or a mediastinal lymphoma in a subject comprising
a. providing
  i. a human clinical sample suspected of having idiopathic pulmonary fibrosis, Castleman's disease, a lymphoma, a thymoma and a sarcoma, and
  ii. reagents for amplification of viral nucleic acids in said sample of embodiment 410, 412 or 424,
b. contacting said clinical sample (i) with said reagents for amplification (ii),
c. amplifying nucleic acids in said clinical sample (i),
d. allowing hybridization to take place between the viral nucleic acids amplified in step c and a labeled nucleic acid probe of embodiment 412, 413, 433, 434 or 435,
e. detecting hybridization of said nucleic acid probe of embodiment 412, 413, 433, 434 or 435 to said amplified nucleic acids produced in step c, thereby diagnosing said patient as having idiopathic pulmonary fibrosis, Castleman's disease, a lymphoma, a thymoma or a sarcoma.
438. A method of diagnosing Castleman's disease, a lymphoma, a thymoma or a sarcoma in a human patient comprising the steps of:
a. providing
  i. a human clinical sample suspected of having Castleman's disease, a lymphoma, a thymoma or a sarcoma,
  ii. reagents for isolation of nucleic acids from said clinical sample,
  iii. reagents for carrying out nucleic acid amplification,
  iv. primers that are capable of amplifying nucleic acid sequences of gamma Herpesvirus targets that have at least 50% homology with Herpesvirus saimiri
b. isolating nucleic from said sample (i) with said reagents (ii)
c. mixing said isolated nucleic acids from step (b) with said amplification reagents (ii) and said primers (iii),
d. carrying out nucleic acid amplification if said gamma Herpesvirus targets are present in said clinical sample (i),
e. detecting the presence of amplified products form step (d).
439. A method of treating a human patient suffering from a disease associated with a gamma Herpesvirus infection wherein said disease is selected from idiopathic pulmonary fibrosis, Castleman's disease, a lymphoma, a thymoma or a sarcoma comprising the step of administering a therapeutically effective amount of an agent selected from an agent that inhibits propagation of the virus, an agent that inhibits replication of the virus, an agent that down-regulates expression of a virus-specific protein, an antibody neutralizes a viral protein, an agent that blocks virus entry into host cells, and an agent that inhibits a viral enzyme.
440. The method of embodiment 439, wherein said agent is an antibody that binds to viral IL-17.
441. The composition of embodiment 358, wherein said labeled nucleic acid is partially hybridized to said one or more sequences derived from Herpesvirus saimiri.
442. The composition of embodiment 358, wherein said labeled nucleic acid has more than 50% homology to said one or more sequences derived from Herpesvirus saimiri.
443. The composition of embodiment 358, wherein said labeled nucleic acid comprises one or more nucleotide analogues.
444. The composition of embodiment 443, wherein said one or more nucleotide analogues confers a property to said labeled nucleic acid selected from differential melting, a detectable signal, and maintenance of stable hybridization with a nucleic acid that is not completely complementary to said labeled nucleic acid.
445. A method of identifying a compound for the treatment of idiopathic pulmonary fibrosis comprising the steps of
(a) administering a compound to a severe combined immunodifficient ("SCID") mouse having fibroblast cells from a patient suffering from idiopathic pulmonary fibrosis,
(b) measuring in a sample from said mouse a level of one or more proteins selected from IL-17, cyclin D, DHFR, thymidylate synthase, and combinations thereof, and
(c) comparing said level of one or more proteins in step (b) with a level of said one or more proteins measured in a sample from a SCID mouse having fibroblast cells from a patient suffering from idiopathic pulmonary fibrosis that has not been exposed to the compound, wherein a level of said one or more proteins measured in step (b) that is lower than a level of said one or more proteins measured in step (c) identifies a compound for treating idiopathic pulmonary fibrosis.
446. The method of embodiment 445, further comprising before step (a) the steps of isolating fibroblast cells from a patient suffering from idiopathic pulmonary fibrosis, and passaging said cells.
447. The method of embodiment 445, wherein said sample is selected from blood cells, lung cells, lung tissue or lungs.
448. The method of embodiment 445, wherein said measuring step (b) is carried out by immunohistochemistry.

449. The method of embodiment 445, wherein said measuring step (b) is carried out by an immunoassay.
450. The method of embodiment 449, wherein said immunoassay is selected from a competitive homogeneous immunoassay, a competitive heterogeneous immunoassay, a one-site noncompetitive homogenous assay and a two-site noncompetitive homogenous assay.
451. The method of embodiment 450, wherein said immunoassay is selected from a radioimmunoassay, a Luminex® assay, a microarray assay, a fluorescence polarization immunoassay, an immunoassay comprising a Förster resonance energy transfer (FRET) signaling system and an enzyme immunoassay.
452. The method of embodiment 445, wherein said measuring step (b) is carried out by measuring an amount of mRNA molecules coding for said one or more proteins in said sample.
453. The method of embodiment 452, wherein said amount of mRNA is measured using a microarray.
454. The method of embodiment 100, wherein said compound for the treatment of idiopathic pulmonary fibrosis is an antibody.
455. The method of embodiment 454, wherein said antibody has selective affinity for IL-17, cyclin D, DHFR, or thymidylate synthase.
456. The method of embodiment 454, wherein said antibody has selective affinity for TGF-β, TGF-β receptor, IL-23, IL-23 receptor, or IL-113.
457. The method of embodiment 445 wherein said compound is a small molecule.
458. The method of embodiment 457, wherein said small molecule is selected from an anti-viral agent, an inhibitor of viral replication, an inhibitor of viral entry into a host cell, and a viral enzyme inhibitor.
459. A method of identifying a compound for the treatment of idiopathic pulmonary fibrosis, comprising the steps of
(a) administering a compound to a severe combined immunodifficient ("SCID") mouse having fibroblast cells from a patient suffering from idiopathic pulmonary fibrosis,
(b) measuring in a sample from said mouse a level of one or more viral markers selected from a Herpesvirus-specific nucleic acid, a Herpesvirus-specific protein and a combination thereof, and
(c) comparing said level of one or more viral markers in step (b) with a level of said one or more viral markers measured in a sample from a SCID mouse having fibroblast cells from a patient suffering from idiopathic pulmonary fibrosis that has not been exposed to the compound,
wherein a level of said one or more viral markers measured in step (b) that is lower than a level of said one or more viral markers measured in step (c) identifies a compound for treating idiopathic pulmonary fibrosis.
460. The method of embodiment 459, further comprising before step (a) the steps of isolating fibroblast cells from a patient suffering from idiopathic pulmonary fibrosis, and passaging said cells.
461. The method of embodiment 459, wherein said sample is selected from blood cells, lung cells, lung tissue or lungs.
462. The method of embodiment 459, wherein said viral marker is a protein and said measuring step (b) is carried out by immunohistochemistry.
463. The method of embodiment 459, wherein said viral marker is a protein and said measuring step (b) is carried out by an immunoassay.
464. The method of embodiment 463, wherein said immunoassay is selected from a competitive homogeneous immunoassay, a competitive heterogeneous immunoassay, a one-site noncompetitive homogenous assay and a two-site noncompetitive homogenous assay.
465. The method of embodiment 464, wherein said immunoassay is selected from a radioimmunoassay, a Luminex® assay, a microarray assay, a fluorescence polarization immunoassay, an immunoassay comprising a Förster resonance energy transfer (FRET) signaling system and an enzyme immunoassay.
466. The method of embodiment 459, wherein said viral marker is a nucleic acid.
467. The method of embodiment 466, wherein said nucleic acid is viral DNA or viral RNA.
468. The method of embodiment 467, wherein said nucleic acid comprises a sequence that codes for a protein selected from IL-17, cyclin D1 thymidylate synthase, and dihydrofolate reductase.
469. The method of embodiment 467, wherein the nucleic acid is mRNA.
470. The method of embodiment 469, wherein said mRNA is measured using a microarray.
471. The method of embodiment 459, wherein said compound for the treatment of idiopathic pulmonary fibrosis is an antibody.
472. The method of embodiment 471, wherein said antibody has selective affinity for IL-17, cyclin D, DHFR, or thymidylate synthase.
473. The method of embodiment 471, wherein said antibody has selective affinity for TGF-β, TGF-β receptor, IL-23, IL-23 receptor, or IL-113.
474. The method of embodiment 459 wherein said compound is a small molecule.
475. The method of embodiment 474, wherein said small molecule is selected from an anti-viral agent, an inhibitor of viral replication, an inhibitor of viral entry into a host cell, and a viral enzyme inhibitor.
476. A method of isolating a viral nucleic acid sequence from a subject suffering from idiopathic pulmonary fibrosis, comprising the steps of
(a) administering fibroblast cells from a subject suffering from idiopathic pulmonary fibrosis to a severe combined immunodifficient ("SCID") mouse;
(b) isolating cells, tissues or organs of said SCID mouse;
(c) isolating nucleic acids from said cells, tissues or organs of step (b); and
(d) amplifying one or more nucleic acids of step (c),
wherein the product of step (d) is enriched for viral nucleic acid sequences.
477. The method of embodiment 476, further comprising before step (a) the steps of isolating fibroblast cells from a patient suffering from idiopathic pulmonary fibrosis, and passaging said cells.
478. The method of embodiment 476, wherein said cells are blood cells.
479. The method of embodiment 476, wherein said cells, tissues or organs are selected from blood cells, lung cells, lung tissue or lungs.
480. The method of embodiment 479, wherein fibrotic material is collected from said lung tissue or lungs.
481. The method of embodiment 476, wherein said amplification step (d) is carried out with primers complementary to a Herpesvirus saimiri nucleic acid.

482. The method of embodiment 476, wherein said amplification step (d) is carried out with primers generic for gammaherpesviruses.
483. The method of embodiment 476, wherein said amplification is carried out by PCR.
484. The method of embodiment 476, wherein said amplification is carried out by RT-PCR.
485. The method of embodiment 476, further comprising after step (d) the steps of:
(e) inserting said amplified nucleic acids of step (c) into a recombinant DNA vector to create a recombinant DNA library;
(f) introducing said recombinant DNA library of step (e) into host cells;
(g) selecting for clones of host cells of step (f) comprising recombinant DNA vectors; and
(h) screening said clones for the presence of viral sequences.
486. A method of isolating a viral nucleic acid sequence from a subject suffering from idiopathic pulmonary fibrosis comprising the steps of
(a) administering fibroblast cells from a subject suffering from idiopathic pulmonary fibrosis to a severe combined immunodeficient ("SCID") mouse;
(b) isolating cells, tissues or organs of said SCID mouse; and
(c) isolating nucleic acids from said cells, tissues or organs of step (b); and
(d) binding nucleic acids comprising viral sequences in said isolated nucleic acids of step (c) to complementary strands of viral DNA,
thereby obtaining nucleic acids that are enriched for viral nucleic acid sequences.
487. The method of embodiment 486, further comprising before step (a) the steps of isolating fibroblast cells from a patient suffering from idiopathic pulmonary fibrosis, and passaging said cells.
488. The method of embodiment 486, wherein said cells are blood cells.
489. The method of embodiment 486, wherein said cells, tissues or organs are selected from blood cells, lung cells, lung tissue or lungs.
490. The method of embodiment 486, wherein fibrotic material is collected from said lung tissue or lungs.
491. The method of embodiment 486, further comprising after step (d) a step of (e) amplifying said isolated nucleic acids of step (d).
492. The method of embodiment 491, wherein said amplification step (e) is carried out with primers complementary to a Herpesvirus saimiri nucleic acid.
493. The method of embodiment 491, wherein said amplification step (e) is carried out with primers generic for gammaherpesviruses.
494. The method of embodiment 491, wherein said amplification is carried out by PCR.
495. The method of embodiment 491, wherein said amplification is carried out by RT-PCR.
496. The method of embodiment 491, further comprising after said amplifying step (e) the steps of:
(f) inserting said amplified nucleic acids of step (e) into a recombinant DNA vector to create a recombinant DNA library;
(g) introducing said recombinant DNA library of step (f) into host cells;
(h) selecting for clones of host cells of step (g) comprising recombinant DNA vectors; and
(i) screening said clones for the presence of viral sequences.
497. A method of isolating a viral nucleic acid sequence from a subject suffering from idiopathic pulmonary fibrosis, comprising the steps of:
(a) administering fibroblast cells from a subject suffering from idiopathic pulmonary fibrosis to a severe combined immunodifficient ("SCID") mouse;
(b) isolating cells, tissues or organs of said SCID mouse;
(c) isolating nucleic acids from said cells, tissues or organs of step (b);
(d) Inserting said isolated nucleic acids of step (c) into a recombinant DNA vector and thereby forming a library of recombinant DNA;
(e) introducing said library of step (d) into host cells;
(f) selecting for clones comprising recombinant DNA vectors in said host cells of step (e); and
(g) screening said clones of step (f) for the presence of viral sequences.
498. The method of embodiment 497, further comprising before step (a) the steps of isolating fibroblast cells from a patient suffering from idiopathic pulmonary fibrosis, and passaging said cells All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A nucleic acid hybridization probe composition comprising at least one of
 a locked nucleic acid (LNA) oligonucleotide having the sequence of SEQ ID NO:5, and
 a locked nucleic acid (LNA) oligonucleotide having the sequence of SEQ ID NO:6.

2. The nucleic acid hybridization probe composition of claim 1, wherein the at least one LNA oligonucleotide is labeled.

3. The nucleic acid hybridization probe composition of claim 1, comprising both the locked nucleic acid (LNA) oligonucleotide having the sequence of SEQ ID NO:5 and the locked nucleic acid (LNA) oligonucleotide having the sequence of SEQ ID NO:6.

4. The nucleic acid hybridization probe composition of claim 3, wherein both of said LNA oligonucleotides are labeled.

5. The nucleic acid hybridization probe composition of claim 3, consisting essentially of both the locked nucleic acid (LNA) oligonucleotide having the sequence of SEQ ID NO:5 and the locked nucleic acid (LNA) oligonucleotide having the sequence of SEQ ID NO:6.

6. The nucleic acid hybridization probe composition of claim 5, wherein both of said LNA oligonucleotides are labeled.

7. A nucleic acid hybridization probe composition comprising at least one of
 a locked nucleic acid (LNA) oligonucleotide having the sequence of SEQ ID NO:7, and
 a locked nucleic acid (LNA) oligonucleotide having the sequence of SEQ ID NO:8.

8. The nucleic acid hybridization probe composition of claim 7, wherein the at least one LNA oligonucleotide is labeled.

9. The nucleic acid hybridization probe composition of claim 7, comprising both the locked nucleic acid (LNA) oligonucleotide having the sequence of SEQ ID NO:7 and the locked nucleic acid (LNA) oligonucleotide having the sequence of SEQ ID NO:8.

10. The nucleic acid hybridization probe composition of claim 9, wherein both of said LNA oligonucleotides are labeled.

11. The nucleic acid hybridization probe composition of claim 9, consisting essentially of both the locked nucleic acid (LNA) oligonucleotide having the sequence of SEQ ID NO:7 and the locked nucleic acid (LNA) oligonucleotide having the sequence of SEQ ID NO:8.

12. The nucleic acid hybridization probe composition of claim 11, wherein both of said LNA oligonucleotides are labeled.

* * * * *